(12) United States Patent
Guba et al.

(10) Patent No.: US 9,605,006 B2
(45) Date of Patent: Mar. 28, 2017

(54) 5-ARYL-1-IMINO-1-OXO-[1,2,4]THIADIAZINES

(71) Applicant: Hoffmann-La Roche Inc., Nutley, NJ (US)

(72) Inventors: Wolfgang Guba, Muellheim (DE); Wolfgang Haap, Loerrach (DE); Andreas Kuglstatter, Loerrach (DE); Jens-Uwe Peters, Grenzach-Wyhlen (DE); Ulrike Obst Sander, Reinach (CH); Christian Schnider, Basel (CH); Roger Wermuth, Sissach (CH); Thomas Woltering, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 15/105,725

(22) PCT Filed: Dec. 17, 2014

(86) PCT No.: PCT/EP2014/078133
§ 371 (c)(1),
(2) Date: Jun. 17, 2016

(87) PCT Pub. No.: WO2015/091595
PCT Pub. Date: Jun. 25, 2015

(65) Prior Publication Data
US 2016/0318952 A1 Nov. 3, 2016

(30) Foreign Application Priority Data

Dec. 20, 2013 (EP) .................................... 13198700

(51) Int. Cl.
*C07D 513/04* (2006.01)

(52) U.S. Cl.
CPC .................................. *C07D 513/04* (2013.01)

(58) Field of Classification Search
CPC ...................................................... C07D 513/04
See application file for complete search history.

(56) References Cited

FOREIGN PATENT DOCUMENTS

JP         EP 2634188 A1 *   9/2013   ........... C07D 487/04

* cited by examiner

*Primary Examiner* — Kahsay Habte

(57) ABSTRACT

The present invention provides a compound of formula I' having BACE1 inhibitory activity, their manufacture, pharmaceutical compositions containing them and their use as therapeutically active substances. The active compounds of the present invention are useful in the therapeutic and/or prophylactic treatment of e.g. Alzheimer's disease.

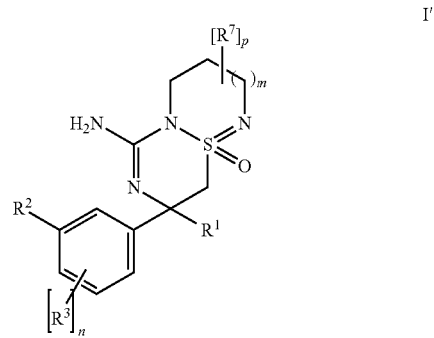

15 Claims, No Drawings

5-ARYL-1-IMINO-1-OXO-[1,2,4]THIADIAZINES

CROSS-REFERENCE TO RELATED APPLICATIONS

This application is a National Stage Application of PCT/EP2014/078133 filed Dec. 17, 2014, which claims priority from European Patent Application No. 13198700.0, filed on Dec. 20, 2013. The priority of both said PCT and European Patent Application are claimed. Each of prior mentioned applications is hereby incorporated by reference herein in its entirety.

BACKGROUND ART

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science*. 2002 July 19; 297(5580):353-6, Selkoe, Cell biology of the amyloid beta-protein precursor and the mechanism of Alzheimer's disease, *Annu Rev Cell Biol*. 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science*. 1999 October 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat Neurosci*. 2001 March; 4(3):231-2, Roberds et al., BACE knock-out mice are healthy despite lacking the primary beta-secretase activity in brain: implications for Alzheimer's disease therapeutics, *Hum Mol Genet*. 2001 June 1; 10(12): 1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol Chem*. 2007 September 7; 282(36):26326). It is thus presumed that inhibitors of BACE1 activity can be useful agents for therapeutic intervention in Alzheimer's disease (AD).

Furthermore, the formation, or formation and deposition, of β-amyloid peptides in, on or around neurological tissue (e.g., the brain) are inhibited by the present compounds, i.e. inhibition of the Aβ-production from APP or an APP fragment.

Inhibitors of BACE1 can in addition be used to treat the following diseases: IBM (inclusion body myositis) (Vattemi G. et al., Lancet. 2001 December 8; 358(9297):1962-4), Down's Syndrome (Barbiero L. et al, Exp Neurol. 2003 August; 182(2):335-45), Wilson's Disease (Sugimoto I. et al., J Biol Chem. 2007 November 30; 282(48):34896-903), Whipple's disease (Desnues B. et al., Clin Vaccine Immunol. 2006 February; 13(2):170-8), SpinoCerebellar Ataxia 1 and SpinoCerebellar Ataxia 7 (Gatchel J. R. et al., *Proc Natl Acad Sci USA* 2008 January 29; 105(4):1291-6), Dermatomyositis (Greenberg S. A. et al., Ann Neurol. 2005 May; 57(5):664-78 and Greenberg S. A. et al., Neurol 2005 May; 57(5):664-78), Kaposi Sarcoma (Lagos D. et al, Blood, 2007 February 15; 109(4):1550-8), Glioblastoma multiforme (E-MEXP-2576, http://www.ebi.ac.uk/microarray-as/aer/result?queryFor=PhysicalArrayDesign&aAccession=A-MEXP-258), Rheumatoid arthritis (Ungetheum U. et al, GSE2053), Amyotrophic lateral sclerosis (Koistinen H. et al., Muscle Nerve. 2006 October; 34(4):444-50 and Li Q. X. et al, Aging Cell. 2006 April; 5(2):153-65), Huntington's Disease (Kim Y. J. et al., Neurobiol Dis. 2006 May; 22(2): 346-56. Epub 2006 January 19 and Hodges A. et al., *Hum Mol Genet*. 2006 March 15; 15(6):965-77. Epub 2006 February 8), Multiple Mieloma (Kihara Y. et al, Proc Natl Acad Sci USA. 2009 December 22; 106(51):21807-12), Malignant melanoma (Talantov D. et al, Clin Cancer Res. 2005 October 15; 11(20):7234-42), Sjogren syndrome (Basset C. et al., Scand J Immunol. 2000 March; 51(3):307-11), Lupus erythematosus (Grewal P. K. et al, Mol Cell Biol. 2006, July; 26(13):4970-81), Macrophagic myofasciitis, juvenile idiopathic arthritis, granulomatous arthritis, Breast cancer (Hedlund M. et al, Cancer Res. 2008 January 15; 68(2):388-94 and Kondoh K. et al., Breast Cancer Res Treat. 2003 March; 78(1):37-44), Gastrointestinal diseases (Hoffmeister A. et al, JOP. 2009 September 4; 10(5):501-6), Autoimmune/inflammatory diseases (Woodard-Grice A. V. et al., *J Biol Chem.* 2008 September 26; 283(39):26364-73. Epub 2008 July 23), Rheumatoid Arthritis (Toegel S. et al, Osteoarthritis Cartilage. 2010 February; 18(2):240-8. Epub 2009 September 22), Inflammatory reactions (Lichtenthaler S. F. et al., *J Biol Chem.* 2003 December 5; 278(49):48713-9. Epub 2003 September 24), Arterial Thrombosis (Merten M. et al., Z Kardiol. 2004 November; 93(11):855-63), Cardiovascular diseases such as Myocardial infarction and stroke (Maugeri N. et al., Srp Arh Celok Lek. 2010 January; 138 Suppl 1:50-2) and Graves disease (Kiljański J. et al, Thyroid. 2005 July; 15(7):645-52).

The present invention provides novel compounds of formula I', their manufacture, medicaments based on a compound in accordance with the invention and their production as well as the use of compounds of formula I' in the control or prevention of illnesses such as Alzheimer's disease. Furthermore the use of compounds of formula I' in the treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease and Wilson's Disease. The novel compounds of formula I' have improved pharmacological properties.

FIELD OF THE INVENTION

The present invention provides 5-aryl-1-imino-1-oxo-[1, 2,4]thiadiazines having BACE1 inhibitory properties, their manufacture, pharmaceutical compositions containing them and their use as therapeutically active substances.

SUMMARY OF THE INVENTION

The present invention provides a compound of formula I',

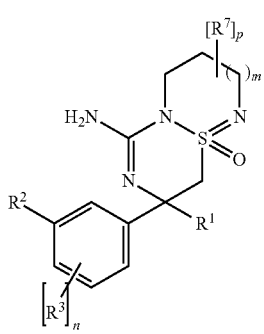

wherein the substituents and variables are as described below and in the claims, or a pharmaceutically acceptable salt thereof.

The present compounds have Asp2 (β-secretase, BACE1 or Memapsin-2) inhibitory activity and may therefore be used in the therapeutic and/or prophylactic treatment of diseases and disorders characterized by elevated β-amyloid levels and/or β-amyloid oligomers and/or β-amyloid plaques and further deposits, particularly Alzheimer's disease.

DETAILED DESCRIPTION OF THE INVENTION

The present invention provides a compound of formula I' and their pharmaceutically acceptable salts thereof, the preparation of the above mentioned compounds, medicaments containing them and their manufacture as well as the use of the above mentioned compounds in the therapeutic and/or prophylactic treatment of diseases and disorders which are associated with inhibition of BACE1, such as Alzheimer's disease. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl (2-methyl-propyl), 1,2-dimethyl-propyl and the like. Particular "$C_{1-6}$-alkyl" are "$C_{1-3}$-alkyl". Specific groups are methyl and ethyl. Most specific is methyl.

The term "halogen-$C_{1-6}$-alkyl", alone or in combination with other groups, refers to $C_{1-6}$-alkyl as defined herein, which is substituted by one or multiple halogen, particularly 1-5 halogen, more particularly 1-3 halogen. Particular halogen is fluoro. Particular "halogen-$C_{1-6}$-alkyl" is fluoro-$C_{1-6}$-alkyl and a particular "halogen-$C_{1-3}$-alkyl" is fluoro-$C_{1-3}$-alkyl. Examples are trifluoromethyl, difluoromethyl, fluoromethyl and the like. Examples are $CHF_2$, $CF_3$ and the like.

The term "cyano", alone or in combination with other groups, refers to $N\equiv C-(NC-)$.

The term "halogen", alone or in combination with other groups, denotes chloro (Cl), iodo (I), fluoro (F) and bromo (Br). Particular "halogen" are Cl, I and F. A specific group is F.

The term "heteroaryl", alone or in combination with other groups, refers to an aromatic carbocyclic group of having a single 4 to 8 membered ring, in particular 5 to 8, or multiple condensed rings comprising 6 to 14, in particular 6 to 10 ring atoms and containing 1, 2 or 3 heteroatoms individually selected from N, O and S, in particular 1N or 2N, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl (pyrimidyl), pyrrolyl, quinolinyl, tetrazolyl, thiazolyl, thienyl, triazolyl, 6,7-dihydro-5H-[1]pyrindinyl and the like. Particular "heteroaryl" are pyridinyl, pyrimidyl, isoxazolyl, 1,2,3-triazolyl and 1H-pyrazolyl. Specific "heteroaryl" are pyridin-2-yl, pyrimidin-5-yl, isoxazol-5-yl, 1,2,3-triazol-4-yl and 1H-pyrazole-3-yl.

The term "cyano-heteroaryl", alone or in combination with other groups, refers to a "heteroaryl" group as defined herein, which is substituted by one or multiple cyano groups, in particular 1 cyano group.

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" groups have 1 to 4 carbon atoms ("$C_{1-4}$-alkoxy"). A specific group is OMe.

The term "halogen-$C_{1-6}$-alkoxy", alone or in combination with other groups, stands for an —O—$C_{1-6}$-alkyl as described herein that is substituted by one or more halogen. Particular "halogen-$C_{1-6}$-alkoxy" is "fluoro-$C_{1-6}$-alkoxy". Examples are —O—$CH_2$—$CHF_2$, —O—$CH_2$—$CF_3$, —O—$CF_3$ and the like.

The term "$C_{2-6}$-alkynyl", alone or in combination with other groups, refers to a linear monovalent hydrocarbon radical of two to six carbon atoms or a branched monovalent hydrocarbon radical of three to six carbon atoms, containing at least one triple bond, e.g., ethynyl, propynyl, and the like.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid. Specific acids are hydrochloric acid, trifluoroacetic acid and fumaric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values ($-\log IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values ($-\log Ki$), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

All separate embodiments may be combined.

One embodiment of the invention provides a compound of formula I',

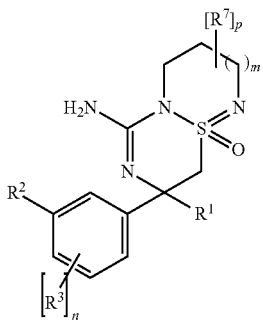

wherein
R¹ is selected from the group consisting of
  i) $C_{1-6}$-alkyl, and
  ii) halogen-$C_{1-6}$-alkyl;
R² is selected from the group consisting of
  i) hydrogen,
  ii) halogen;
  iii) NH—C(=O)—R⁴,
  iv) aryl,
  v) aryl, substituted by 1-3 substituents individually selected from cyano, $C_{1-6}$-alkyl, halogen-$C_{1-6}$-alkyl and halogen
  vi) heteroaryl,
  vii) heteroaryl, substituted by 1-3 substituents individually selected from R⁶, and
  viii) —C≡C—R⁵;
R³ is halogen;
R⁴ is selected from the group consisting of
  i) heteroaryl, and
  ii) heteroaryl, optionally substituted by 1-3 substituents individually selected from R⁶,
R⁵ is selected from the group consisting of
  i) aryl,
  ii) aryl, optionally substituted by 1-3 substituents individually selected from cyano, $C_{1-6}$-alkyl, halogen-$C_{1-6}$-alkyl and halogen
  iii) heteroaryl, and
  iv) heteroaryl, optionally substituted by 1-3 substituents individually selected from cyano, $C_{1-6}$-alkyl, halogen-$C_{1-6}$-alkyl and halogen;
R⁶ is selected from the group consisting of
  i) cyano,
  ii) halogen;
  iii) $C_{1-6}$-alkyl,
  iv) halogen-$C_{1-6}$-alkyl,
  v) $C_{2-6}$-alkynyl-O—,
  vi) heteroaryl, and
  vii) heteroaryl, optionally substituted by 1-3 substituents individually selected from cyano, $C_{1-6}$-alkyl, $C_{1-6}$-alkoxy, halogen-$C_{1-6}$-alkyl, halogen-$C_{1-6}$-alkoxy and halogen;
R⁷ is selected from the group consisting of
  i) halogen, and
  ii) halogen-$C_{1-6}$-alkyl;
m is 1 or 2;
n is 0 or 1; and
p is 0, 1 or 2;
or pharmaceutically acceptable salts thereof.

A certain embodiment of the invention provides a compound of formula I', wherein p is 0.

A certain embodiment of the invention provides a compound of formula I', wherein R⁷ is fluoro and p is 2.

A certain embodiment of the invention provides a compound of formula I', wherein R⁷ is CF₃ and p is 1.

A certain embodiment of the invention provides a compound of formula I' that is of formula I,

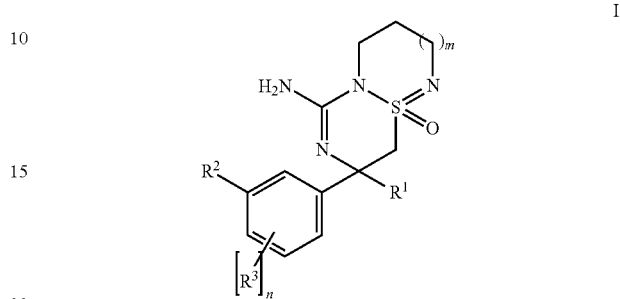

wherein
R¹ is selected from the group consisting of
  i) $C_{1-6}$-alkyl, and
  ii) halogen-$C_{1-6}$-alkyl;
R² is selected from the group consisting of
  i) hydrogen,
  ii) halogen;
  iii) NH—C(=O)—R⁴,
  iv) aryl,
  v) aryl, substituted by 1-3 substituents individually selected from cyano, $C_{1-6}$-alkyl, halogen-$C_{1-6}$-alkyl and halogen
  vi) heteroaryl,
  vii) heteroaryl, substituted by 1-3 substituents individually selected from R⁶, and
  viii) —C≡C—R⁵;
R³ is halogen;
R⁴ is selected from the group consisting of
  i) heteroaryl, and
  ii) heteroaryl, optionally substituted by 1-3 substituents individually selected from cyano, $C_{1-6}$-alkyl, halogen-$C_{1-6}$-alkyl and halogen,
R⁵ is selected from the group consisting of
  i) aryl,
  ii) aryl, optionally substituted by 1-3 substituents individually selected from cyano, $C_{1-6}$-alkyl, halogen-$C_{1-6}$-alkyl and halogen
  iii) heteroaryl, and
  iv) heteroaryl, optionally substituted by 1-3 substituents individually selected from cyano, $C_{1-6}$-alkyl, halogen-$C_{1-6}$-alkyl and halogen;
R⁶ is selected from the group consisting of
  i) cyano,
  ii) halogen;
  iii) $C_{1-6}$-alkyl,
  iv) halogen-$C_{1-6}$-alkyl,
  v) heteroaryl, and
  vi) heteroaryl, optionally substituted by 1-3 substituents individually selected from cyano, $C_{1-6}$-alkyl, $C_{1-6}$-alkoxy, halogen-$C_{1-6}$-alkyl, halogen-$C_{1-6}$-alkoxy and halogen;
m is 1 or 2; and
n is 0 or 1;
or pharmaceutically acceptable salts thereof.

A certain embodiment of the invention provides a compound of formula I' as described herein, wherein $R^1$ is selected from the group consisting of
i) $C_{1-6}$-alkyl, and
ii) halogen-$C_{1-6}$-alkyl;
$R^2$ is selected from the group consisting of
i) hydrogen,
ii) halogen;
iii) NH—C(=O)—$R^4$,
iv) aryl,
v) aryl, substituted by 1-3 substituents individually selected from cyano, $C_{1-6}$-alkyl, halogen-$C_{1-6}$-alkyl and halogen
vi) heteroaryl,
vii) heteroaryl, substituted by 1-3 substituents individually selected from cyano, $C_{1-6}$-alkyl, halogen-$C_{1-6}$-alkyl and halogen, and
viii) —C≡C—$R^5$;
$R^3$ is halogen;
$R^4$ is selected from the group consisting of
i) heteroaryl, and
ii) heteroaryl, optionally substituted by 1-3 substituents individually selected from cyano, $C_{1-6}$-alkyl, halogen-$C_{1-6}$-alkyl and halogen;
$R^5$ is selected from the group consisting of
i) heteroaryl, and
ii) heteroaryl, optionally substituted by 1-3 substituents individually selected from cyano, $C_{1-6}$-alkyl, halogen-$C_{1-6}$-alkyl and halogen;
m is 0, 1, 2 or 3; and
n is 0 or 1;
or pharmaceutically acceptable salts thereof.

A certain embodiment of the invention provides a compound of formula I' as described herein, wherein m is 2, n is 1, $R^1$ is $C_{1-6}$-alkyl, $R^2$ is H, halogen, NH—C(=O)—$R^4$, —C≡C—$R^5$, cyano-heteroaryl or heteroaryl, $R^3$ is halogen, $R^4$ is cyano-heteroaryl and $R^5$ is heteroaryl substituted by halogen and halogen-$C_{1-6}$-alkyl.

A certain embodiment of the invention provides a compound of formula I' as described herein, wherein m is 2, n is 1, $R^1$ is methyl, $R^2$ is H, I, NH—C(=O)—$R^4$, —C≡C—$R^5$, cyano-pyridyl or pyrimidyl, $R^3$ is F, $R^4$ is cyano-pyridyl and $R^5$ is chloro-difluoromethyl-1H-pyrazolyl.

A certain embodiment of the invention provides a compound of formula I' as described herein, which is of formula Ia, wherein $R^1$, $R^2$ and m are as described in claim 1

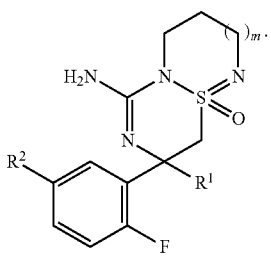

Ia

A certain embodiment of the invention provides a compound of formula I' as described herein, wherein m is 2.

A certain embodiment of the invention provides a compound of formula I' as described herein, wherein $R^1$ is $C_{1-6}$-alkyl.

A certain embodiment of the invention provides a compound of formula I' as described herein, wherein $R^1$ is methyl.

A certain embodiment of the invention provides a compound of formula I' as described herein, wherein $R^2$ is NH—C(=O)—$R^4$.

A certain embodiment of the invention provides a compound of formula I' as described herein, wherein $R^4$ is heteroaryl, optionally substituted by cyano.

A certain embodiment of the invention provides a compound of formula I' as described herein, wherein $R^4$ is cyano-heteroaryl.

A certain embodiment of the invention provides a compound of formula I' as described herein, wherein $R^4$ is cyano-pyridyl.

A certain embodiment of the invention provides a compound of formula I' as described herein, wherein $R^2$ is heteroaryl, optionally substituted by cyano.

A certain embodiment of the invention provides a compound of formula I' as described herein, wherein $R^2$ is cyano-heteroaryl or heteroaryl.

A certain embodiment of the invention provides a compound of formula I' as described herein, wherein $R^2$ is 5-cyano-pyridinyl or pyrimidyl.

A certain embodiment of the invention provides a compound of formula I' as described herein, wherein $R^2$ is —C≡C—$R^5$.

A certain embodiment of the invention provides a compound of formula I' as described herein, wherein $R^5$ is heteroaryl, optionally substituted by halogen and halogen-$C_{1-6}$-alkyl.

A certain embodiment of the invention provides a compound of formula I' as described herein, wherein $R^5$ is heteroaryl substituted by halogen and halogen-$C_{1-6}$-alkyl.

A certain embodiment of the invention provides a compound of formula I' as described herein, wherein $R^5$ is chloro-difluoromethyl-1H-pyrazolyl.

A certain embodiment of the invention provides a compound of formula I' as described herein, wherein $R^2$ is H.

A certain embodiment of the invention provides a compound of formula I' as described herein, wherein $R^2$ is halogen.

A certain embodiment of the invention provides a compound of formula I' as described herein, wherein $R^2$ is I.

A certain embodiment of the invention provides a compound of formula I' as described herein that is selected from the group consisting of
(3RS,4aRS)-3-(2-fluoro-phenyl)-3-methyl-4a-oxo-3,4,6,7,8,9-hexahydro-4a$\lambda^6$-thia-2,5,9a-triaza-benzocyclohepten-1-ylamine,
(3RS,4aSR)-3-(2-fluoro-phenyl)-3-methyl-4a-oxo-3,4,6,7,8,9-hexahydro-4a$\lambda^6$-thia-2,5,9a-triaza-benzocyclohepten-1-ylamine,
(3R,4aR)-3-(2-fluoro-phenyl)-3-methyl-4a-oxo-3,4,6,7,8,9-hexahydro-4a$\lambda^6$-thia-2,5,9a-triaza-benzocyclohepten-1-ylamine,
(3R,4aS)-3-(2-fluoro-phenyl)-3-methyl-4a-oxo-3,4,6,7,8,9-hexahydro-4a$\lambda^6$-thia-2,5,9a-triaza-benzocyclohepten-1-ylamine,
(3R,4aR)-3-(2-Fluoro-5-iodo-phenyl)-3-methyl-4a-oxo-3,4,6,7,8,9-hexahydro-4a$\lambda^6$-thia-2,5,9a-triaza-benzocyclohepten-1-ylamine,
(3R,4aS)-3-(2-Fluoro-5-iodo-phenyl)-3-methyl-4a-oxo-3,4,6,7,8,9-hexahydro-4a$\lambda^6$-thia-2,5,9a-triaza-benzocyclohepten-1-ylamine,
5-cyano-pyridine-2-carboxylic acid [3-((3RS,4aRS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide, 5-cyano-pyridine-2-carboxylic acid [3-((3RS,4aSR)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide, 5-cyano-pyridine-2-carboxylic acid [3-((3R,4aR)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide, 5-cyano-pyridine-2-carboxylic acid [3-((3R,4aS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide, 5-[3-((3R,4aR)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-nicotinonitrile, (3R,4aR)-3-(2-Fluoro-5-pyrimidin-5-yl-phenyl)-3-methyl-4a-oxo-3,4,6,7,8,9hexahydro-4a$\lambda^6$-thia-2,5,9a-triaza-benzocyclohepten-1-ylamine, 5-Chloro-pyridine-2-carboxylic acid [3-((3R,4aR)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide, 5-[3-((3R,4aS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-nicotinonitrile, (3R,4aS)-3-(2-Fluoro-5-pyrimidin-5-yl-phenyl)-3-methyl-4a-oxo-3,4,6,7,8,9hexahydro-4a$\lambda^6$-thia-2,5,9a-triaza-benzocyclohepten-1-ylamine, 5-Cyano-3-methyl-pyridine-2-carboxylic acid [3-((3R,4aR)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide, 5-Chloro-pyridine-2-carboxylic acid [3-((3R,4aS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide, 5-Cyano-3-methyl-pyridine-2-carboxylic acid [3-((3R,4aS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide, (9R,11R)-7-amino-9-(5-(3-(5-chloropyrimidin-2-yl)isoxazol-5-yl)-2-fluorophenyl)-9-methyl-2,3,4,5,9,10-hexahydro-[1,2,4]thiadiazino[1,2-a][1,2,7]thiadiazepine 11-oxide 2,2,2-trifluoroacetate, (9R,11S)-7-amino-9-(5-(3-(5-chloropyrimidin-2-yl)isoxazol-5-yl)-2-fluorophenyl)-9-methyl-2,3,4,5,9,10-hexahydro-[1,2,4]thiadiazino[1,2-a][1,2,7]thiadiazepine 11-oxide 2,2,2-trifluoroacetate, 6-(4-(3-((9R,11S)-7-amino-9-methyl-11-oxido-2,3,4,5,9,10-hexahydro-[1,2,4]thiadiazino[1,2-a][1,2,7]thiadiazepin-9-yl)-4-fluorophenyl)-1H-1,2,3-triazol-1-yl)nicotinonitrile 2,2,2-trifluoroacetate, 4-((3-((9R,11R)-7-amino-9-methyl-11-oxido-2,3,4,5,9,10-hexahydro-[1,2,4]thiadiazino[1,2-a][1,2,7]thiadiazepin-9-yl)-4-fluorophenyl)ethynyl)benzonitrile 2,2,2-trifluoroacetate, (9R,11R)-7-amino-9-(2-fluoro-5-(3-(5-methoxypyrazin-2-yl)isoxazol-5-yl)phenyl)-9-methyl-2,3,4,5,9,10-hexahydro-[1,2,4]thiadiazino[1,2-a][1,2,7]thiadiazepine 11-oxide 2,2,2-trifluoroacetate, (9R,11S)-7-amino-9-(2-fluoro-5-(3-(5-methoxypyrazin-2-yl)isoxazol-5-yl)phenyl)-9-methyl-2,3,4,5,9,10-hexahydro-[1,2,4]thiadiazino[1,2-a][1,2,7]thiadiazepine 11-oxide 2,2,2-trifluoroacetate, (9R,11R)-7-amino-9-(5-(3-(5-(2,2-difluoroethoxy)pyrazin-2-yl)isoxazol-5-yl)-2-fluorophenyl)-9-methyl-2,3,4,5,9,10-hexahydro-[1,2,4]thiadiazino[1,2-a][1,2,7]thiadiazepine 11-oxide 2,2,2-trifluoroacetate, 3-Chloro-5-cyano-pyridine-2-carboxylic acid [3-((3R,4aS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide, 5-(2,2,2-Trifluoro-ethoxy)-pyridine-2-carboxylic acid [3-((3R,4aS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide, 5-But-2-ynyloxy-pyrazine-2-carboxylic acid [3-((3R,4aS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide, 5-Fluoro-3-methyl-pyridine-2-carboxylic acid [3-((3R,4aS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide, N-(3-((2S,9R)-7-amino-9-methyl-11-oxido-2-(trifluoromethyl)-2,3,4,5,9,10-hexahydro-[1,2,4]thiadiazino[1,2-a][1,2,7]thiadiazepin-9-yl)-4-fluorophenyl)-5-cyano-3-methylpicolinamide, and N-(3-((8R)-6-amino-3,3-difluoro-8-methyl-10-oxido-3,4,8,9-tetrahydro-2H-[1,2,6]thiadiazino[1,2-a][1,2,4]thiadiazin-8-yl)-4-fluorophenyl)-5-cyano-3-methylpicolinamide, or pharmaceutically acceptable salts thereof.

A certain embodiment of the invention provides a compound of formula I as described herein that is selected from the group consisting of (3R,4aR)-3-(2-Fluoro-5-iodo-phenyl)-3-methyl-4a-oxo-3,4,6,7,8,9-hexahydro-4a$\lambda^6$-thia-2,5,9a-triaza-benzocyclohepten-1-ylamine, (3R,4aR)-3-(2-Fluoro-5-pyrimidin-5-yl-phenyl)-3-methyl-4a-oxo-3,4,6,7,8,9hexahydro-4a$\lambda^6$-thia-2,5,9a-triaza-benzocyclohepten-1-ylamine, (3R,4aR)-3-(2-fluoro-phenyl)-3-methyl-4a-oxo-3,4,6,7,8,9-hexahydro-4a$\lambda^6$-thia-2,5,9a-triaza-benzocyclohepten-1-ylamine, (3R,4aR)-3-[5-(4-Chloro-1-difluoromethyl-1H-pyrazol-3-ylethynyl)-2-fluoro-phenyl]-3-methyl-4a-oxo-3,4,6,7,8,9-hexahydro-4a$\lambda^6$-thia-2,5,9a-triaza-benzocyclohepten-1-ylamine, (3R,4aS)-3-(2-Fluoro-5-iodo-phenyl)-3-methyl-4a-oxo-3,4,6,7,8,9-hexahydro-4a$\lambda^6$-thia-2,5,9a-triaza-benzocyclohepten-1-ylamine, (3R,4aS)-3-(2-Fluoro-5-pyrimidin-5-yl-phenyl)-3-methyl-4a-oxo-3,4,6,7,8,9hexahydro-4a$\lambda^6$-thia-2,5,9a-triaza-benzocyclohepten-1-ylamine, (3R,4aS)-3-(2-fluoro-phenyl)-3-methyl-4a-oxo-3,4,6,7,8,9-hexahydro-4a$\lambda^6$-thia-2,5,9a-triaza-benzocyclohepten-1-ylamine, (3R,4aS)-3-[5-(4-Chloro-1-difluoromethyl-1H-pyrazol-3-ylethynyl)-2-fluoro-phenyl]-3-methyl-4a-oxo-3,4,6,7,8,9-hexahydro-4a$\lambda^6$-thia-2,5,9a-triaza-benzocyclohepten-1-ylamine, (3RS,4aRS)-3-(2-fluoro-phenyl)-3-methyl-4a-oxo-3,4,6,7,8,9-hexahydro-4a$\lambda^6$-thia-2,5,9a-triaza-benzocyclohepten-1-ylamine, (3RS,4aSR)-3-(2-fluoro-phenyl)-3-methyl-4a-oxo-3,4,6,7,8,9-hexahydro-4a$\lambda^6$-thia-2,5,9a-triaza-benzocyclohepten-1-ylamine, 5-[3-((3R,4aR)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-nicotinonitrile, 5-[3-((3R,4aS)-1-amino-3-methyl-4a-oxo-3,4,6,7,8,9-hexahydro-4a$\lambda^6$thia-2,5,9a-triaza-benzocyclohepten-3-yl)-4-fluoro-phenyl]-nicotinonitrile, 5-cyano-pyridine-2-carboxylic acid [3-((3R,4aR)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide, 5-cyano-pyridine-2-carboxylic acid [3-((3R,4aS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide, 5-cyano-pyridine-2-carboxylic acid [3-((3RS,4aRS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide, and 5-cyano-pyridine-2-carboxylic acid [3-((3RS,4aSR)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide.

A certain embodiment of the invention provides a compound of formula I' as described herein whenever prepared by a process as described herein.

A certain embodiment of the invention provides a compound of formula I' as described herein for use as therapeutically active substance.

A certain embodiment of the invention provides a compound of formula I' as described herein for the use as inhibitor of BACE1 activity.

A certain embodiment of the invention provides a compound of formula I' as described herein for the use as therapeutically active substance for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I' as described herein for the use as therapeutically active substance for the therapeutic and/or prophylactic treatment of Alzheimer's disease.

A certain embodiment of the invention provides a compound of formula I' as described herein for the use as therapeutically active substance for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a pharmaceutical composition comprising a compound of formula I' as described herein and a pharmaceutically acceptable carrier and/or a pharmaceutically acceptable auxiliary substance.

A certain embodiment of the invention provides the use of a compound of formula I' as described herein for the manufacture of a medicament for the use in inhibition of BACE1 activity.

A certain embodiment of the invention provides the use of a compound of formula I' as described herein for the manufacture of a medicament for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides the use of a compound of formula I' as described herein for the manufacture of a medicament for the therapeutic and/or prophylactic treatment of Alzheimer's disease.

A certain embodiment of the invention provides the use of a compound of formula I' as described herein for the manufacture of a medicament for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides the use of a compound of formula I' as described herein for the manufacture of a medicament for the therapeutic and/or prophylactic treatment of Alzheimer's disease.

A certain embodiment of the invention provides a compound of formula I' as described herein for the use in inhibition of BACE1 activity.

A certain embodiment of the invention provides a compound of formula I' as described herein for the use in the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I' as described herein for the use in the therapeutic and/or prophylactic treatment of Alzheimer's disease.

A certain embodiment of the invention provides a compound of formula I' as described herein for the use in the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a method for the use in inhibition of BACE1 activity, particularly for the therapeutic and/or prophylactic treatment of diseases and disorders characterized by elevated β-amyloid levels and/or β-amyloid oligomers and/or f3-amyloid plaques and further deposits or Alzheimer's disease, which method comprises administering compound of formula I' as described herein to a human being or animal.

A certain embodiment of the invention provides a method for the use in the therapeutic and/or prophylactic treatment of Alzheimer's disease, which method comprises administering a compound of formula I' as described herein to a human being or animal.

A certain embodiment of the invention provides a method for the use in the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease, which method comprises administering a compound of formula I' as described herein to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I'.

The compounds of formula I' may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

The compounds of formula I' may be prepared in accordance with the following schemes.

The starting material is commercially available or may be prepared in accordance with known methods. Any previously defined residues and variables will continue to have the previously defined meaning unless otherwise indicated.

The compounds of formula I' can be prepared through a number of synthetic routes for example as illustrated in schemes 1-5. The preparation of compounds of formula I' of the present invention may be carried out in sequential or convergent synthetic routes. Syntheses of the compounds of the invention are shown in the following schemes 1-4. The skills required for carrying out the reaction and purification of the resulting products are known to those skilled in the art. The substituents and indices used in the following description of the processes have the significance given herein before unless indicated to the contrary.

In more detail, the compounds of formula I' can be manufactured by the methods given below, by the methods given in the examples or by analogous methods. Appropriate reaction conditions for the individual reaction steps are known to a person skilled in the art. The reaction sequence is not limited to the one displayed in schemes described below, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The compounds of formula I' described in the schemes 1-5 can be isolated and purified by methods known to those skilled in the art, such as but not limited to ion exchange chromatography, solid phase extraction, liquid-liquid extraction, silica chromatography, crystallization and preparative HPLC.

In more detail, compounds of formula I according to the present invention can be prepared by the methods and procedures given below. Some typical procedures for the preparation of compounds of formula I are illustrated in Schemes 1-5.

Scheme 1: Synthesis of intermediates A14

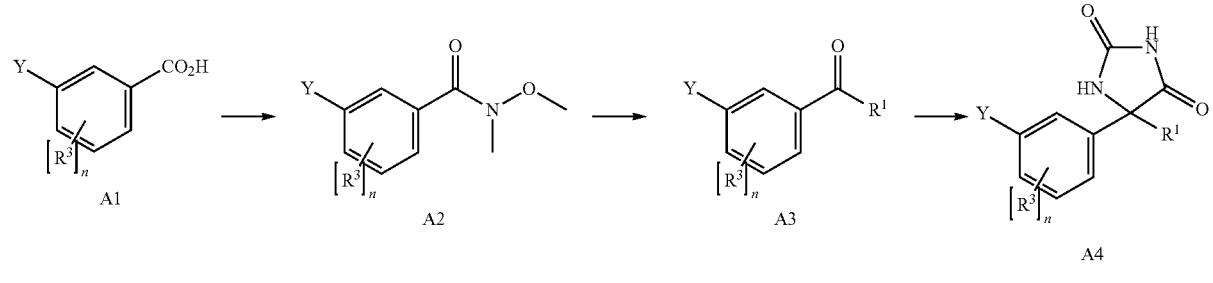

-continued

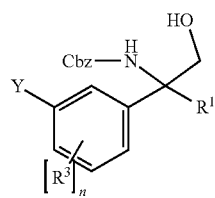 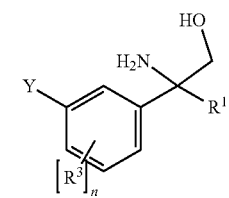 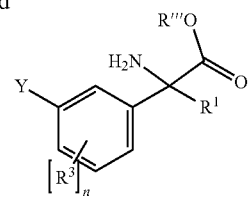 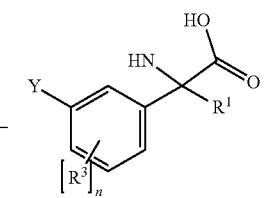

A8     A7     A6     A5

R''' = alkyl

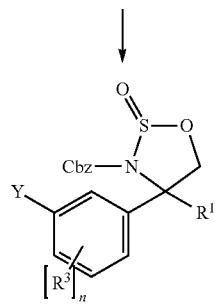 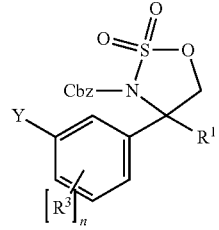 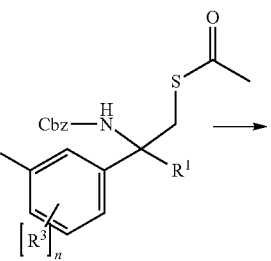 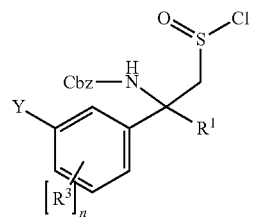

A9     A10     A11     A12

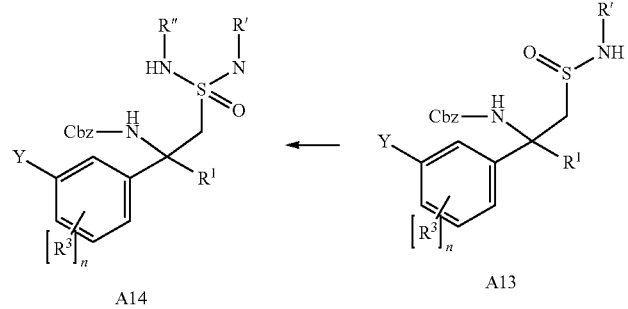

A14     A13

Non commercial ketones of general formula A3 can be synthesized by routes such as depicted in scheme 1 or by other routes known to those skilled in the art. Weinreb amides of formula A2 can be obtained by standard condensation reactions of the acids of formula A1 with N,O-dimethylhydroxylamine or by the intermediate formation of the acyl chloride of acids of formula A1 using an agent such as oxalyl chloride or thionyl chloride using standard conditions such as triethylamine/dichloromethane. The amides of formula A2 can be reacted with organometallics such as methylmagnesium bromide (for $R^1$=Me) in inert aprotic solvents such as tetrahydrofuran or diethyl ether to yield the desired ketones of formula A3.

According to scheme 1, ketones of general formula A3 (wherein Y has the meaning of either hydrogen or a leaving group like halogen, e.g. bromide) can be reacted with cyanides, like potassium cyanide, together with ammonium carbonate in polar solvents such as alcohols, e.g. ethanol, water or tetrahydrofuran and mixtures thereof, to form hydantoins of formula A4. The hydantoin can then be treated with water along with a base such as sodium hydroxide or a strong acid such as sulfuric acid at temperatures ranging from ambient temperature to reflux to yield the amino acid of formula A5. The amino alcohol of formula A7 is obtained by esterification of the acid of formula A5 with a lower alcohol, such as methanol or ethanol, followed by reduction of the resulting amino ester of formula A6 with lithium aluminum hydride or other suitable reagents both steps performed under conditions known to those skilled in the art.

The amino alcohol of formula A7 can be selectively N-protetected to the N-benzyloxycarbonylated amino alcohol of formula A8 with benzyl chloroformate, using a biphasic mixture of aqueous sodium bicarbonate solution and an organic solvent such as tetrahydrofuran or dichloromethane at 0° C. to 23° C., preferably 23° C.

The N-benzyloxycarbonylated amino alcohol of formula A8 can be reacted with thionyl chloride to the cyclic sulfamidite of formula A9 in the presence of an amine base, in particular pyridine, in a solvent such as acetonitrile or dichloromethane, starting at low temperature such as −78° C. or −40° C. and warming up to 0° C. or ambient temperature.

The cyclic sulfamidite of formula A9 can be oxidized to the cyclic sulfamidate of formula A10 by an alkali periodate, such as sodium or potassium periodate, in the presence of a ruthenium salt, such as ruthenium(III) chloride, in solvent mixtures consisting of water, acetonitrile and ethyl acetate or tetrachloromethane at temperatures between 0° C. and 50° C., preferably at 23° C.

The cyclic sulfamidate of formula A10 can be regioselectively opened with a sulfur nucleophile, such as potassium thioacetate, and subsequently hydrolyzed under acidic conditions to the N-benzyloxycarbonylated amino thioacetate of formula A11. The ring opening proceeds in a polar aprotic solvent, such as N,N-dimethylformamide, at temperatures between 0° C. and 60° C., preferably at 23° C. After removal of all volatiles from the ring opening step under vacuum by evaporation the crude reaction mixture is subjected to acidic hydrolysis in a mixture of a mineral acid, in particular 20% aqueous sulfuric acid, and a solvent such as diethyl ether or dichloromethane at temperatures between 0° C. and 50° C., preferably at 23° C.

The N-benzyloxycarbonylated amino thioacetate of formula A11 is transformed into the N-benzyloxycarbonylated amino sulfinyl chloride of formula A12 by treatment with sulfuryl chloride and acetic anhydride in a chlorinated solvent such as dichloromethane at temperatures between 30° C. and 0° C. The crude sulfinyl chlorides of formula A12 can be used directly in the next step to produce the N-benzyloxycarbonylated amino sulfinamides of formula A13 which is achieved by simple reaction with an excess of an amine R'—NH₂ or mixtures of an amine R'—NH₂ with an amine base, such as triethylamine or N-ethyl-N,N-diisopropylamine, in a solvent such as dichlormethane or tetrahydrofuran, at temperatures starting as low as −78° C. and warming up to 0° C. or 23° C.

The N-benzyloxycarbonylated amino sulfonimidamides of formula A14 can be prepared from the N-benzyloxycarbonylated amino sulfinamides of formula Aβ by reaction with a chlorinating reagent such as N-chlorosuccinamide or tert-butyl hypochlorite, preferably tert-butyl hypochlorite, in an inert solvent such as acetonitrile, tetrahydrofuran or dichloromethane, preferably dichloromethane, at temperatures starting as low as −78° C. and warming up to 0° C., followed by reaction with an excess of an amine R"—NH₂ or mixtures of an amine R"—NH₂ with an amine base, such as triethylamine or N-ethyl-N,N-diisopropylamine at temperatures starting as low as −78° C. and warming up to 0° C. or 23° C.

Scheme 2: Synthesis of intermediate A20

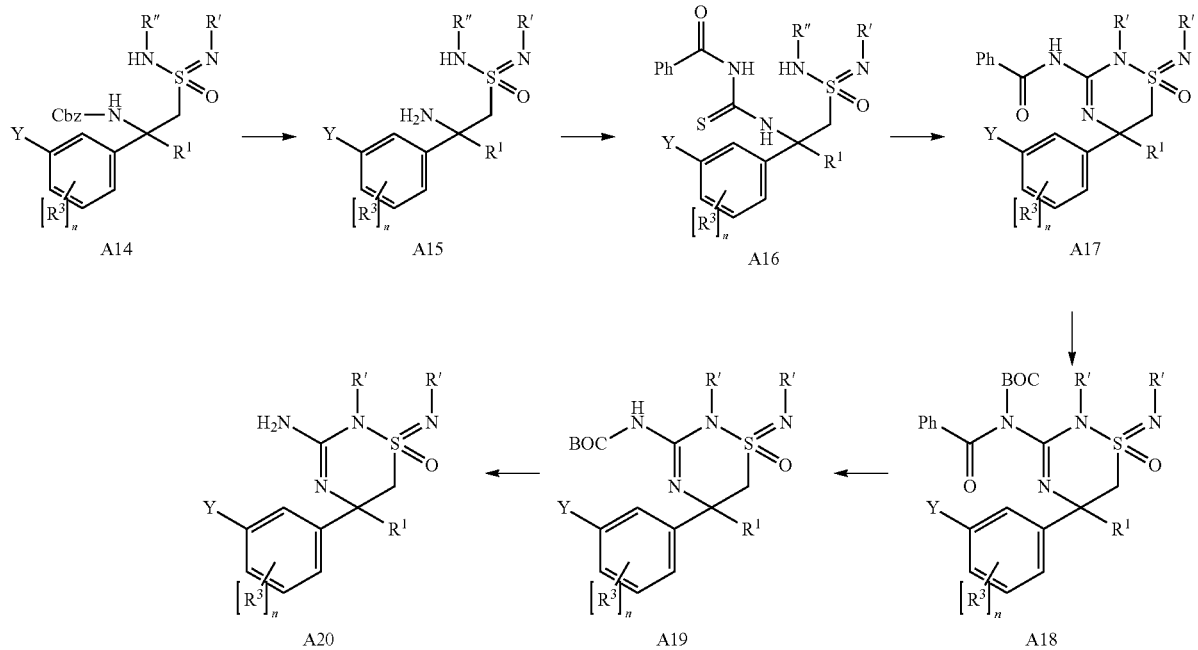

The amino sulfonimidamides of formula A15 are made by deprotection of the N-benzyloxycarbonylated amino sulfonimidamides of formula A14 by various methods known to someone skilled in the art as e.g. described in Greene's Protective Groups in Organic Synthesis 4$^{th}$ edition, Peter G. M. Wuts, Theodora W. Greene, Wiley-Interscience, 2007, p. 750 ff. One of the most common methods uses catalytic hydrogenation, i.e. reaction with hydrogen gas in the presence of a catalyst such as palladium on carbon in a solvent such as ethyl acetate, ethanol or methanol at temperatures between 23° C. and 80° C., preferably at 23° C.

Reaction of the amino sulfonimidamides of formula A15 with an isothiocyanate such as benzoylisothiocyanate in solvents such as ethyl acetate, tetrahydrofuran or acetonitrile at temperatures between 0° C. and 80° C., preferably 23° C., affords the thiourea sulfonimidamides of formula A16.

The thiourea sulfonimidamides of formula A16 can be cyclized to the N-benzoylated amidine sulfonimidamides of formula A17 by dehydration through reaction with a carbodiimide, like e.g. dicyclohexylcarbodiimide, diisopropylcarbodiimide or N-(3-dimethylaminopropyl)-N'-ethylcarbodiimide hydrochloride (EDC HCl), preferably EDC. HCl, in solvents such as ethyl acetate, tetrahydrofuran or acetonitrile, preferably acetonitrile, at temperatures between 23° C. and 100° C., preferably 80° C.

The switch of protecting groups from the N-benzoylated amidine sulfonimidamides of formula A17 to the N-tert-butoxycarbonylated amidine sulfonimidamides of formula A19 can be achieved in a two step procedure by first reaction with di-tert-butyldicarbonate (Boc₂O) in the presence of an amine base such as triethylamine or N-ethyl-N,N-diisopropylamine, in a solvent such as dichlormethane, tetrahydrofuran or acetonitrile, at temperatures between 0° C. and 40°

C., preferably 23° C., to give the doubly acylated amidine sulfonimidamides of formula A18, and second selective removal of the benzoyl group by reaction of the doubly acylated amidine sulfonimidamides of formula A18 with an amine nucleophile, like e.g. diethylamine, dimethylamine or ammonia, preferably ammonia, in a solvent such as dichloromethane or tetrahydrofuran, preferably tetrahydrofuran, at temperatures between 0° C. and 40° C., preferably 23° C.

The amidine sulfonimidamides of formula A20 can be made by deprotection of the N-tert-butoxycarbonylated amidine sulfonimidamides of formula A19 by various methods known to someone skilled in the art as e.g. described in Greene's Protective Groups in Organic Synthesis 4$^{th}$ edition, Peter G. M. Wuts, Theodora W. Greene, Wiley-Interscience, 2007, p. 727 ff. One of the most common methods uses treatment with a strong acid, like e.g. hydrochloric acid or trifluoroacetic acid (TFA), in a solvent such as dioxane or dichloromethane, at temperatures between 0° C. and 23° C., preferably at 23° C.

Alternatively the amidine sulfonimidamides of formula A20 can be made by using the following sequence: treatment of amino sulfonimidamides of formula A15 with O-benzyl carbonisothiocyanatidate (CbzNCS; CAS-no. 63220-36-0) in analogy to the above described reaction with benzoylisothiocyanate (A15 to A16), cyclization with a carbodiimide in analogy to the above described transformation of A16 to A17, followed by cleavage of the benzyloxycarbonyl group yielding directly the amidine sulfonimidamides of formula A20 by various methods known to someone skilled in the art as e.g. described in Greene's Protective Groups in Organic Synthesis 4$^{th}$ edition, Peter G. M. Wuts, Theodora W. Greene, Wiley-Interscience, 2007, p. 750 ff. One of the most common methods uses catalytic hydrogenation, i.e. reaction with hydrogen gas in the presence of a catalyst such as palladium on carbon in a solvent such as ethyl acetate, ethanol or methanol at temperatures between 23° C. and 80° C., preferably at 23° C.

Scheme 3: Synthesis of compounds of formula I'-c

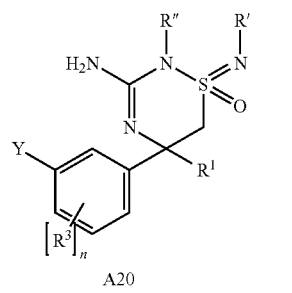

A20
Y = H

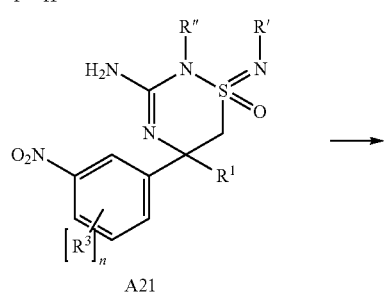

A21

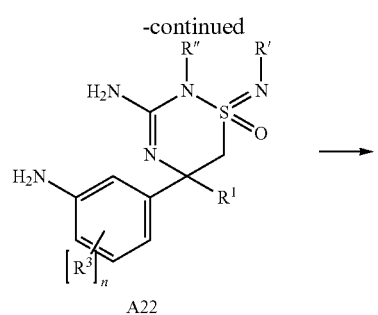

A22

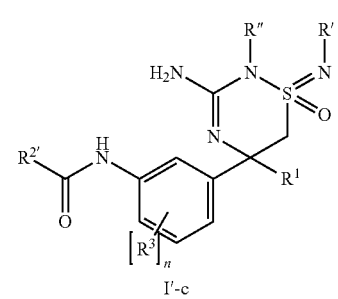

I'-c

If the amidine sulfonimidamides of formula A20 contain Y=Br reduction to Y=H can be accomplished by hydrogenation using a catalyst such as Pd/C in protic solvents, such as alcohols, in particular ethanol or methanol, preferably in the presence of ammonium hydroxide, preferably at ambient temperature.

The nitration of the amidine sulfonimidamides of formula A20 with Y=H to give the nitro amidine sulfonimidamides of formula A21 follows a standard procedure involving neat sulfuric acid and fuming nitric acid without using a solvent at temperatures between 0° C. and 23° C.

The reduction of the nitro group in the nitro amidine sulfonimidamides of formula A21 to give the aniline of formula A22 can be accomplished by hydrogenation using a catalyst such as Pd/C in protic solvents, such as alcohols, in particular ethanol or methanol, at ambient temperature.

Selective amide coupling of the aniline of formula A22 and a carboxylic acid to give the amide of formula I can be effected with 4-(4,6-dimethoxy[1.3.5]triazin-2-yl)-4-methylmorpholinium chloride (DMTMM) hydrate in a solvent such as an alcohol, in particular methanol, at ambient temperature.

Scheme 3: Synthesis of compounds of formula I'-d

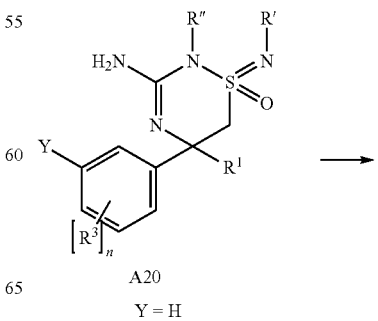

A20
Y = H

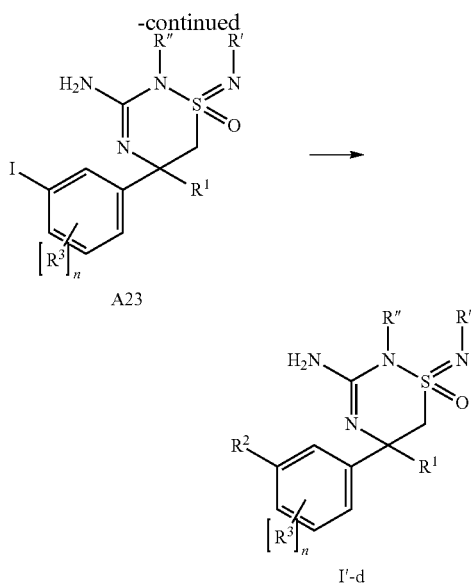

A23

I'-d

The amidine sulfonimidamides of formula A20 can be iodinated to the amidine sulfonimidamides of formula A23 by reaction with an iodinating reagent such as iodine monochloride or N-iodosuccinimide, preferably N-iodosuccinimide, in a solvent such as dichloromethane in the presence of a strong organic acid such as methansulfonic acid or trifluoromethanesulfonic acid, preferably trifluoromethanesulfonic acid, at temperatures between 10° C. and 40° C., preferably 23° C.

Compounds of formula I wherein $R^2$ is either an aryl- or heteroaryl group can be prepared from the amidine sulfonimidamides of formula A20 where Y=Br or the amidine sulfonimidamides of formula A23 by methods known to someone skilled in the art using the Suzuki-Miyaura coupling, i.e. palladium-catalyzed (e.g. tetrakis(triphenylphosphine)palladium or 1,1'-bis(diphenylphosphino)ferrocenepalladium(II)dichloride dichloromethane complex) cross coupling between organoboronic acids or esters thereof and compounds of formula A20 (Y=Br) or A23 in the presence of an aqueous carbonate or hydrogen carbonate base, like e.g. sodium carbonate, potassium carbonate, cesium carbonate or sodium or potassium hydrogen carbonate, in solvents such as tetrahydrofuran, 1,2-dimethoxyethane, 1,4-dioxane, at temperatures between 23° C. and 100° C., to give compounds of formula I.

Compounds of formula I wherein $R^2$ is connected to the phenyl group via a triple bond can be prepared from the amidine sulfonimidamides of formula A20 where Y=Br or the amidine sulfonimidamides of formula A23 by methods known to someone skilled in the art using the Sonogashira coupling, i.e. reaction of terminal alkynes with aryl iodides (A23) or bromides (A20, Y=Br) with a palladium catalyst, e.g. bis(triphenyphosphine)palladium(II) chloride, a copper (I) co-catalyst, e.g. copper(I) iodide, and an amine base, e.g. triethylamine, in solvents such as tetrahydrofuran or N,N-dimethylformamide at temperatures between 23° C. and 90° C.

If the amidine sulfonimidamides of formula A20 contain Y=Br or the amidine sulfonimidamides of formula A23 are taken as starting materials they can be reacted with ammonia equivalents, such as benzophenone imine, in the presence of a suitable transition metal catalyst, such as bis(dibenzylideneacetone)palladium (0) ((dba)$_2$Pd) or tris(dibenzylideneacetone)dipalladium (0) ((dba)$_3$Pd$_2$)), and a suitable ligand, such as rac-2,2'-bis(diphenylphosphino)-1,1'-binaphthyl (rac-BINAP), 2-dicyclohexylphosphino-2',4',6'-triisopropylbiphenyl (X-PHOS) or 2-di-tert-butylphosphino-2',4',6'-triisopropylbiphenyl (t-Bu X-PHOS), in the presence of a base, such as sodium tert-butoxide, potassium phosphate or cesium carbonate, in a suitable solvent, such as toluene or 1,4-dioxane, under an inert atmosphere, such as nitrogen or argon, at temperatures between 80 and 110° C., to produce after following reaction with aqueous mineral acid such as hydrochloric or sulfuric acid in an organic solvent such as tetrahydrofuran or 1,4-dioxane at temperatures between 0° C. and 50° C., preferably 23° C., compounds of formula A22.

Scheme 4: Alternative synthesis of intermediate amino alcohols of formual A7.

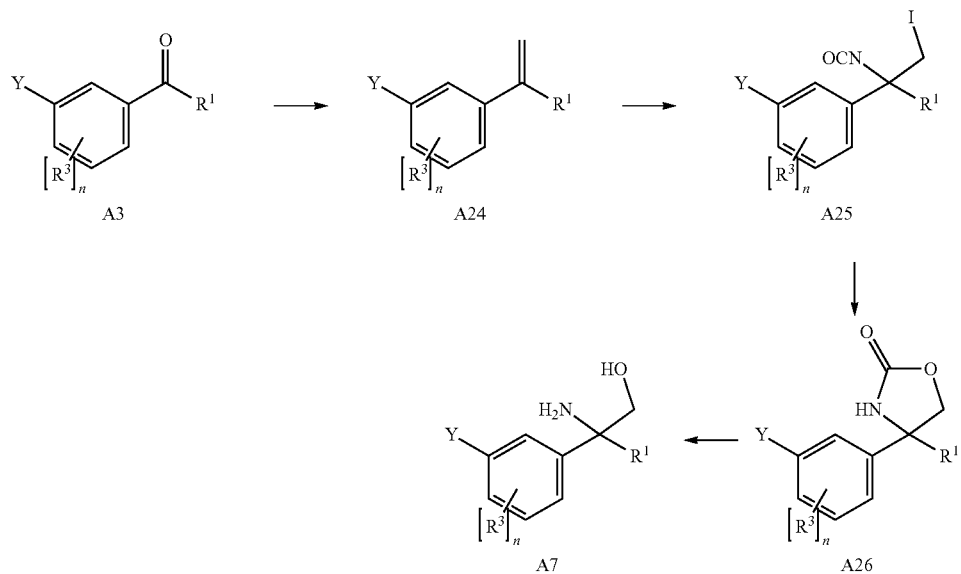

Alternatively, intermediate amino alcohols of formula A7 can be obtained as follows: According to scheme 4, the formation of a methyltriphenyl-phosphonium ylide produced by strong base such as butyllithium in solvents such as tetrahydrofuran or toluene at temperatures between −78° C. and 0° C. followed by addition of the ketone of formula A3 yields the desired alkenes of formula A24. The alkenes can then be reacted with a mixture of silver cyanate and iodine in solvents such as diethyl ether or mixtures of ethyl acetate and acetonitrile. The resultant iodoisocyanates of formula A25 can then be heated with alcohols like tert-butanol and a base like triethylamine or Huenig's base to yield the oxazolidinones of formula A26. Hydrolysis of the resultant oxazolidinone of formula A26 with aqueous base like lithium hydroxide yields the amino alcohol of formula A7.

chiral directing group as described by Tang & Ellman or by A. Avenoza, J. H. Busto, F. Corzana, J. M. *Peregrina*, D. Sucunza, M. M. Zurbano in Synthesis 2005, (4), 575-578. The sulfinyl imine of formula A27 can be treated with an mixed alkyl alkoxide aluminum cyanide reagent, e.g. ethylaluminium cyanoisopropoxide [EtAl(O-i-Pr)CN], in a solvent such as an ether, e.g. diethyl ether or more preferably tetrahydrofuran, at temperatures starting from 78° C. and eventually raising to 10° C., to generate the nitriles of formula A28 as described e.g. by A. Avenoza, J. H. Busto, F. Corzana, J. M. *Peregrina*, D. Sucunza, M. M. Zurbano in Synthesis 2005, (4), 575-578.

Hydrolysis of the chiral directing group in the nitriles of formula A28 to give first the chiral amino amide of formula A29 can be accomplished with a mineral acid, e.g. sulfuric acid or preferably hydrochloric acid in a solvent such as an Scheme 5: Enantioselective synthesis of intermediate amino alchols of formula A7.

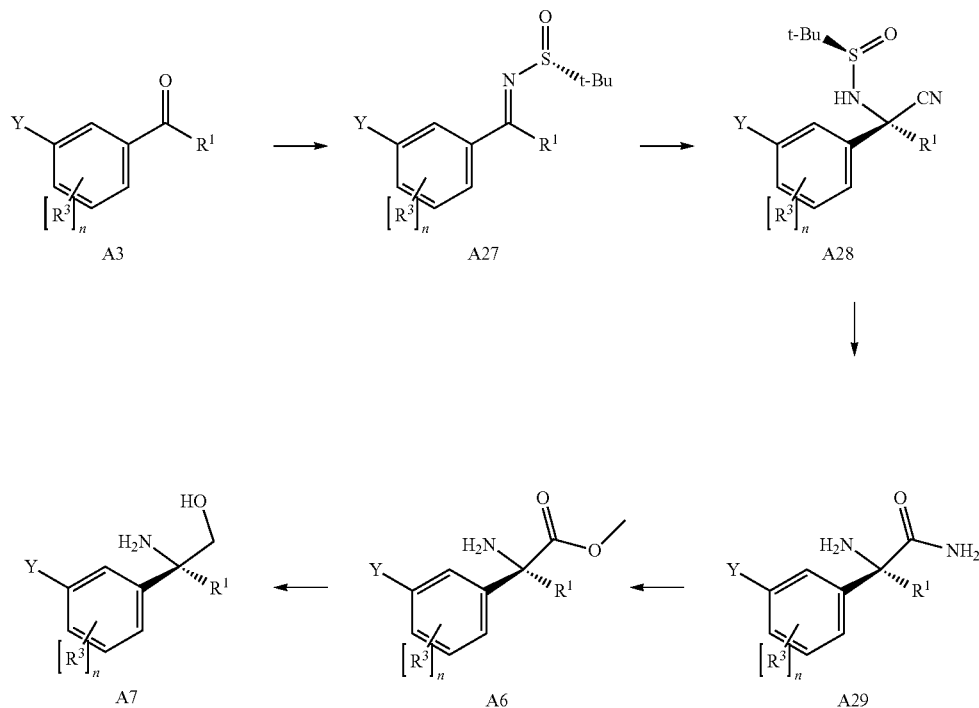

Intermediate amino alcohols of formula A7 can be prepared in an enantioselective manner as follows: aromatic ketones of formula A3 can be converted into the sulfinyl imine of general formula A27 in analogy to T. P. Tang & J. A. Ellman, J. Org. Chem. 1999, 64, 12, by condensation of the aryl ketone group and a sulfinamide, e.g. an alkyl sulfinamide, in this case most preferably (R)-(+)-tert-butylsulfinamide in the presence of a Lewis acid such as e.g. a titanium(IV)alkoxide, more preferably titanium(IV)ethoxide in a solvent such as an ether, e.g. diethyl ether or more preferably tetrahydrofuran, at temperatures between 23° C. and 70° C.

The conversion of the sulfinyl imine of formula A27 to the nitrile of formula A28 proceeds stereoselectively by the ether, e.g. diethyl ether, tetrahydrofuran or more preferably 1,4-dioxane, which is followed by another acidic reaction with a mineral acid, e.g. anhydrous hydrochloric acid or preferably sulfuric acid in a solvent such as an aliphatic alcohol, e.g. ethanol or more preferably methanol, at temperatures from 23° C. to 80° C., to give the chiral amino esters of formula A6.

Also chiral amino esters of formula A6 can be reduced to the chiral amino alcohols of formula A7 by reaction with a reducing agent such as e.g. lithium borohydride or more preferably lithium aluminum hydride in an ether solvent, like e.g. diethyl ether or more preferably tetrahydrofuran, at temperatures between 0° C. and 50° C., preferably at 23° C.

Scheme 6: Synthesis of compounds of forumula I¢ in which R2 is substituted isoxazol-5-yl or substituted 1,2,3-triazole-4-yl

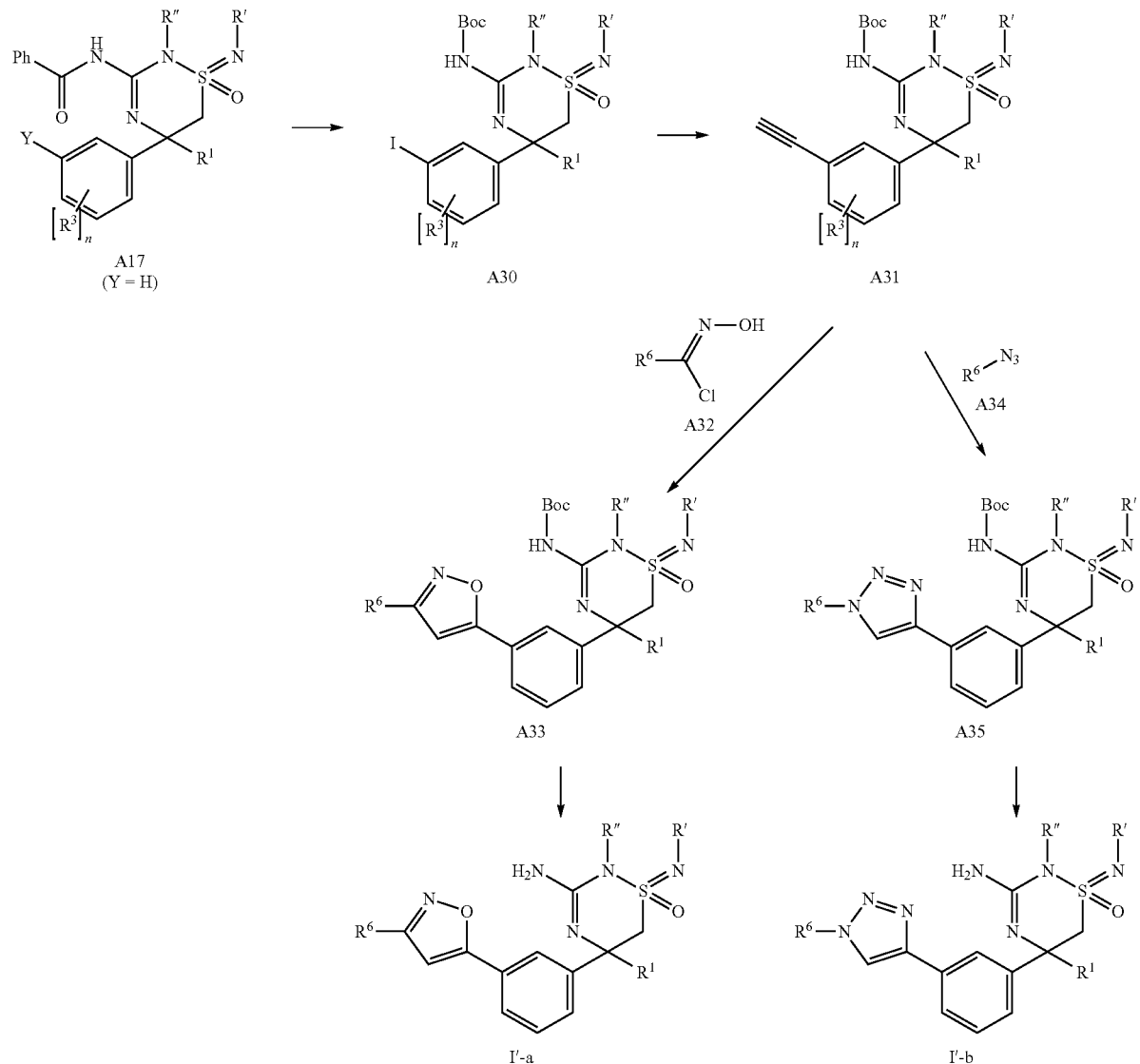

Benzoylated amidine sulfonimidamides of formula A17 in which Y=H can be iodinated by reaction with an iodinating reagent such as iodine monochloride or N-iodosuccinimide, preferably N-iodosuccinimide, in a solvent such as dichloromethane in the presence of a strong organic acid such as methansulfonic acid or trifluoromethanesulfonic acid, preferably trifluoromethanesulfonic acid, at temperatures between −10° C. and 40° C., preferably 23° C. The mono- and diiodinated products of this reaction can be treated with di-tert-butyldicarbonate (Boc$_2$O) in the presence of an amine base such as triethylamine or N-ethyl-N,N-diisopropylamine, in a solvent such as dichlormethane, tetrahydrofuran or acetonitrile, at temperatures between 0° C. and 40° C., preferably 23° C., to give the doubly acylated amidine sulfonimidamides. Selective removal of the benzoyl or iodobenzoyl group can be achieved by reaction with an amine nucleophile, like e.g. diethylamine, dimethylamine or ammonia, preferably ammonia, in a solvent such as dichloromethane or tetrahydrofuran, preferably tetrahydrofuran, at temperatures between 0° C. and 40° C., preferably 23° C. to give compounds of formula A30.

Sonogashira coupling of iodides A30 with an acetylene derivative protected on one end such as trimethylsilylacetylene can be achieved with a palladium catalyst, e.g. bis(triphenyphosphine)palladium(II) chloride, a copper(I) co-catalyst, e.g. copper(I) iodide, and an amine base, e.g. triethylamine under conditions known to those skilled in the art. Removal of the protecting group (e.g. R$_3$Si such as Me$_3$Si) to give terminal acetylenes of formula A31 can be achieved by methods well known in the art, e.g. by treatment with fluoride containing reagents such as tetrabutylammonium fluoride in a solvent such as dichloromethane or THF at a temperature between 0° C. and ambient temperature or by treatment with potassium carbonate in a solvent such as ethanol or methanol at ambient temperature.

Conversion of acetylenes A31 into isoxazoles A33 can be achieved by a 1,3-dipolar cycloaddition with a reagent system consisting of a heteroaryl-carboximidoyl chloride A32 and a base such as sodium bicarbonate or triethylamine in a solvent such as THF or isopropanol at temperatures between 0° C. and reflux temperature of the solvent.

Conversion of acetylenes A31 into 1,2,3-triazoles A35 can be achieved by a copper(I)-catalyzed cycloaddition with heteroaryl azides A34 using either a copper(I) reagent such as CuI or copper(I) trifluoromethanesulfonate benzene complex or a copper(II) reagent such as $CuSO_4$ in the presence of a reducing agent such as sodium ascorbate and a base such as $NaHCO_3$ in a solvent or solvent mixtures such as toluene, THF or DMF at a temperature from ambient temperature to reflux of the solvent.

Removal of the amine-protecting group BOC in compounds A33 and A35 to give compounds of formula I' can be achieved by methods well known in the art, e.g. by treatment with strong carbonic acids, e.g. trifluoroacetic acid, in a halogenated solvent, e.g. dichloromethane, at temperatures between 0° C. and 23° C.

The corresponding pharmaceutically acceptable salts with acids can be obtained by standard methods known to the person skilled in the art, e.g. by dissolving the compound of formula I' in a suitable solvent such as e.g. dioxane or tetrahydrofuran and adding an appropriate amount of the corresponding acid. The products can usually be isolated by filtration or by chromatography. The conversion of a compound of formula I' into a pharmaceutically acceptable salt with a base can be carried out by treatment of such a compound with such a base. One possible method to form such a salt is e.g. by addition of 1/n equivalents of a basic salt such as e.g. $M(OH)_1$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate. Specific is hydrochloride.

Insofar as their preparation is not described in the examples, the compounds of formula I' as well as all intermediate products can be prepared according to analogous methods or according to the methods set forth herein.

Starting materials are commercially available, known in the art or can be prepared by methods known in the art or in analogy thereto.

It will be appreciated that the compounds of general formula I' in this invention may be derivatised at functional groups to provide derivatives which are capable of conversion back to the parent compound in vivo.

Pharmacological Tests

The compounds of formula I' and their pharmaceutically acceptable salts possess valuable pharmacological properties. It has been found that the compounds of the present invention are associated with inhibition of BACE1 activity. The compounds were investigated in accordance with the test given hereinafter.

Cellular Aβ-Lowering Assay:

The Abeta 40 AlphaLISA Assay can be used. The HEK293 APP cells were seeded in 96 well Microtiter plates in cell culture medium (Iscove's, plus 10% (v/v) fetal bovine serum, penicillin/streptomycin) to about 80% confluency and the compounds were added at a 3× concentration in ⅓ volume of culture medium (final DMSO concentration was kept at 1% v/v). After 18-20 hrs incubation at 37° C. and 5% $CO_2$ in a humidified incubator, the culture supernatants were harvested for the determination of Aβ40 concentrations using Perkin-Elmer Human Amyloid beta 1-40 (high specificity) Kit (Cat# AL275C).

In a Perkin-Elmer White Optiplate-384 (Cat#6007290), 2 ul culture supernatants were combined with 2µl of a 10× AlphaLISA Anti-hAβAcceptor beads+Biotinylated Antibody Anti-Aβ1-40 Mix (50 µg/mL/5 nM). After 1 hour room temperature incubation, 16 µl of a 1.25× preparation of Streptavidin (SA) Donor beads (25 µg/mL) were added and incubated for 30 minutes in the Dark. Light Emission at 615 nm was then recorded using EnVision-Alpha Reader. Levels of Aβ40 in the culture supernatants were calculated as percentage of maximum signal (cells treated with 1% DMSO without inhibitor). The $IC_{50}$ values were calculated using the Excel XLfit software.

TABLE 1

| | $IC_{50}$ values | |
|---|---|---|
| Exam. | Structure | BACE1 $IC_{50}$ [µM] |
| A20a1 | | |
| A20a2 | | 1.04 |

TABLE 1-continued

| Exam. | Structure | BACE1 IC$_{50}$ [μM] |
|---|---|---|
| A20b1 | (Chiral structure) | |
| A20b2 | (Chiral structure) | |
| A23a1 | (Chiral structure) | |
| A23a2 | (Chiral structure) | |
| 1 | (structure) | 0.045 |

TABLE 1-continued

| | | IC50 values | |
|---|---|---|---|
| Exam. | Structure | | BACE1 IC50 [μM] |
| 2 | | | 0.002 |
| 3 | Chiral | | |
| 4 | Chiral | | |
| 5 | Chiral | | |
| 6 | Chiral | | |

TABLE 1-continued

| | | IC₅₀ values | |
|---|---|---|---|
| Exam. | Structure | | BACE1 IC$_{50}$ [μM] |
| 7 | *(Chiral structure: 5-chloropyridine-2-carboxamide linked to fluorophenyl bearing thiadiazepine-sulfoxide with guanidine)* | | |
| 8 | *(Chiral structure: 5-cyanopyridin-3-yl linked to fluorophenyl bearing thiadiazepine-sulfoxide with guanidine)* | | |
| 9 | *(Chiral structure: pyrimidin-5-yl linked to fluorophenyl bearing thiadiazepine-sulfoxide with guanidine)* | | |
| 10 | *(Chiral structure: 5-cyano-3-methylpyridine-2-carboxamide linked to fluorophenyl bearing thiadiazepine-sulfoxide with guanidine)* | | |

TABLE 1-continued

IC₅₀ values

| Exam. | Structure | BACE1 IC₅₀ [μM] |
|---|---|---|
| 11 | 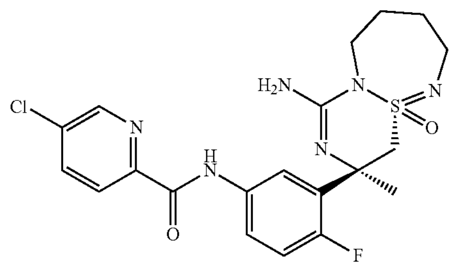 | |
| 12 | 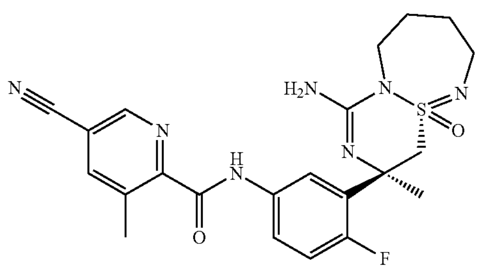 [SMILES: C[C@@]1(c2cc(NC(=O)c3ccc(C#N)cn3)ccc2F)C[S@@]2(=O)=NCCCCN2C(N)=N1] | |
| 13 | | 0.012 |
| 14 | | 0.095 |

TABLE 1-continued
| | IC$_{50}$ values | |
|---|---|---|
| Exam. | Structure | BACE1 IC$_{50}$ [μM] |
| 15 | 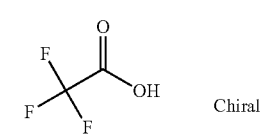 | 0.095 |
| 16 | 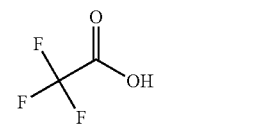 | 0.021 |
| 17 | 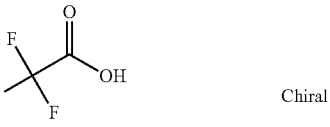 | 0.009 |

TABLE 1-continued
| | IC50 values | |
|---|---|---|
| Exam. | Structure | BACE1 IC50 [μM] |
| 18 | 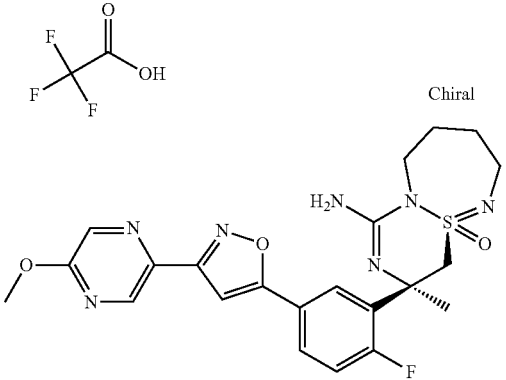 [SMILES: O=C(O)C(F)(F)F ; COc1cnc(-c2cc(-c3ccc(F)c([C@]4(C)C[S@]5(=O)=NCCCCN5C(N)=N4)c3)on2)cn1] | 0.694 |
| 19 | 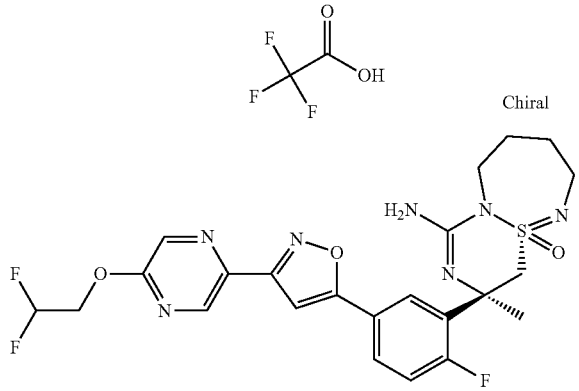 [SMILES: O=C(O)C(F)(F)F ; C[C@@]1(c2cc(-c3cc(-c4cnc(OCC(F)F)cn4)no3)ccc2F)C[S@@]2(=O)=NCCCCN2C(N)=N1] | 0.014 |
| 20 | 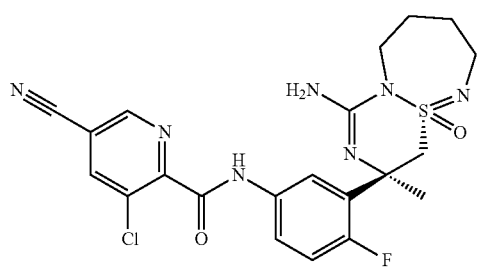 | 0.001 |
| 21 | 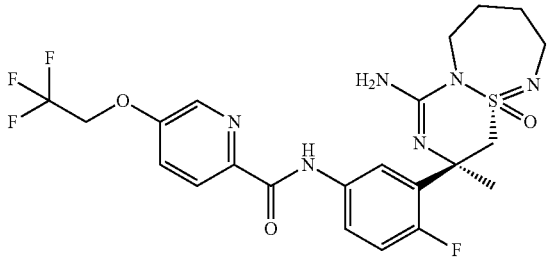 | 0.01 |

TABLE 1-continued

| Exam. | Structure | BACE1 IC$_{50}$ [μM] |
|---|---|---|
| 22 | Chiral | 0.0002 |
| 23 | Chiral | 0.0015 |
| 24 | 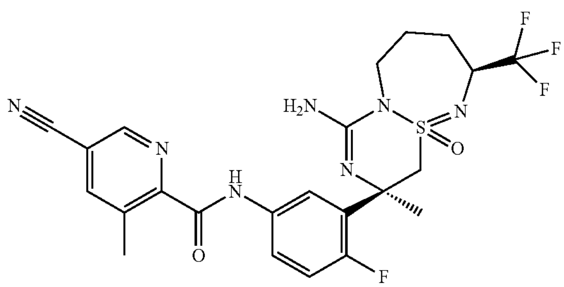 [SMILES: Cc1cc(C#N)cnc1C(=O)Nc1ccc(F)c([C@]2(C)CS3(=O)=N[C@H](C(F)(F)F)CCCN3C(N)=N2)c1] | |
| 25 | 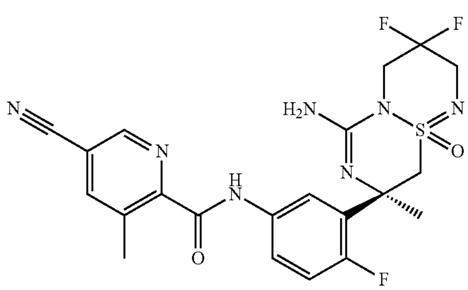 [SMILES: Cc1cc(C#N)cnc1C(=O)Nc1ccc(F)c([C@]2(C)CS3(=O)=NCC(F)(F)CN3C(N)=N2)c1] | 0.002 |

Pharmaceutical Compositions

The compounds of formula I' and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I' and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I' or a pharmaceutically acceptable salt thereof and a therapeutically inert carrier are also provided by the present invention, as is a process for their production, which comprises bringing one or more compounds of formula I' and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I' or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I'. Examples of compositions according to the invention are:

Example A

Tablets of the following composition are manufactured in the usual manner:

TABLE 2 possible tablet composition

| ingredient | mg/tablet | | | |
|---|---|---|---|---|
|  | 5 | 25 | 100 | 500 |
| Compound of formula I' | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the Following Composition are Manufactured:

TABLE 3 possible capsule ingredient composition

| ingredient | mg/capsule | | | |
|---|---|---|---|---|
|  | 5 | 25 | 100 | 500 |
| Compound of formula I' | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula I', lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the Following Composition are Manufactured:

TABLE 4 possible soft gelatin capsule ingredient composition

| ingredient | mg/capsule |
|---|---|
| Compound of formula I' | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I' is dissolved in a warm melting of the other ingredients and the mixture is filled into soft gelatin capsules of appropriate size. The filled soft gelatin capsules are treated according to the usual procedures.

Example C

Suppositories of the Following Composition are Manufactured:

TABLE 6

| possible suppository composition | |
| --- | --- |
| ingredient | mg/supp. |
| Compound of formula I' | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I' is added thereto and stirred until it has dispersed completely. The mixture is poured into suppository moulds of suitable size, left to cool; the suppositories are then removed from the moulds and packed individually in wax paper or metal foil.

Example D

Injection Solutions of the Following Composition are Manufactured:

TABLE 7

| possible injection solution composition | |
| --- | --- |
| ingredient | mg/injection solution. |
| Compound of formula I' | 3 |
| Polyethylene Glycol 400 | 150 |
| acetic acid | q.s. ad pH 5.0 |
| water for injection solutions | ad 1.0 ml |

Manufacturing Procedure

The compound of formula I' is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the Following Composition are Manufactured:

TABLE 8

| possible sachet composition | |
| --- | --- |
| ingredient | mg/sachet |
| Compound of formula I' | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I' is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

General

NMR: $^1$H NMR spectra were recorded on a Bruker AC-300 spectrometer at 25° C. with TMS (tetramethylsilane) or residual $^1$H of the given deuterated solvents as internal standards.

MS: Mass spectra (MS) were measured either with ion spray positive or negative (ISP or ISN) method on a Perkin-Elmer SCIEX API 300 or with electron impact method (EI, 70 eV) on a Finnigan MAT SSQ 7000 spectrometer.

LC-MS (ESI, positive or negative ion) data were recorded on Waters UPLC-MS Systems equipped with Waters Acquity, a CTC PAL auto sampler and a Waters SQD single quadrupole mass spectrometer using ES ionization modes (positive and/or negative). The separation was achieved on a Zorbax Eclipse Plus C18 1.7 µm 2.1×30 mm column at 50° C.; A=0.01% formic acid in water, B=acetonitrile at flow 1; gradient: 0 min 3% B, 0.2 min 3% B, 2 min 97% B, 1.7 min 97% B, 2.0 min 97% B. The injection volume was 2 µL. MS (ESI, positive or negative ion): FIA (flow injection analysis)-MS were recorded on an AppliedBiosystem API150 mass spectrometer. Sample introduction was made with a CTC PAL auto sampler and a Shimadzu LC-10ADVP Pump. The samples were directly flushed to the ESI source of the mass spectrometer with a flow 50 µL/min of a mixture of acetonitrile and 10 mM ammonium acetate (1:1) without a column. The injection volume was 2 µL.

Synthesis of Intermediates A4

A4a: (RS)-5-(3-Bromo-phenyl)-5-methyl-imidazolidine-2,4-dione

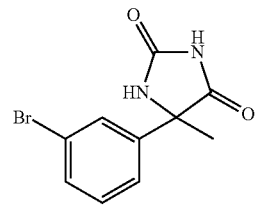

A mixture of 3-bromo-acetophenone (10.0 g, 50 mmol), potassium cyanide (4.96 g, 75 mmol), and ammonium carbonate (33.45 g, 348 mmol) in ethanol (65 ml) was heated in an autoclave at 120° C. for 16 h. For the workup, the reaction mixture was cooled to room temperature, and then treated with water (250 ml) and ethyl acetate (500 ml). The aqueous layer was separated and re-extracted with ethyl acetate (250 ml). The combined organic layers were washed twice with saturated sodium chloride solution (2×250 ml), thereafter dried over sodium sulfate, and evaporated at reduced pressure. There were obtained 13.2 g (98.6% of theory) of (RS)-5-(3-bromo-phenyl)-5-methyl-imidazolidine-2,4-dione as a white solid. The purity of the product allowed using it in the next step without further purification. Mass (calculated) $C_{10}H_9BrN_2O_2$ [269.099]; (found) [M−H]$^−$=267, 269.

A4b: (RS)-5-(5-Bromo-2-fluoro-phenyl)-5-methyl-imidazolidine-2,4-dione

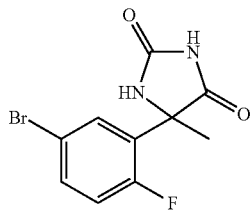 [SMILES: CC1(c2cc(Br)ccc2F)NC(=O)NC1=O]

The reaction of commercially available 1-(5-bromo-2-fluoro-phenyl)-ethanone with potassium cyanide and ammonium carbonate in ethanol in an autoclave at 120° C. for 16 h yielded the title compound as light yellow solid. Mass (calculated) $C_{10}H_8BrFN_2O_2$ [287.087]; (found) $[M-H]^- = $ 285, 287.

A4c: (RS)-5-(2-Fluoro-phenyl)-5-methyl-imidazolidine-2,4-dione

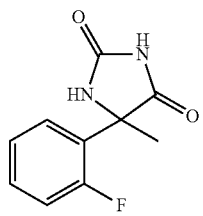

A mixture of freshly distilled 1-(2-fluorophenyl)ethanone (27.6 g, 24.6 ml, 200 mmol, Eq: 1.00), potassium cyanide (15.6 g, 240 mmol, Eq: 1.20), ammonium carbonate (96.1 g, 1.00 mol, Eq: 5.00) and ammonium hydroxide (25%) (130 g, 145 ml, 931 mmol, Eq: 4.65) in ethanol (250 ml) and water (200 ml) was stirred at 60° C. for 5.5 h. The ethanol was removed in vacuum, then cooled to 0° C., cautiously acidified the residue to pH 1, the precipitate was filtered off, washed with dilute HCl and dried at 50° C. first at rotary evaporator, then at high vacuum to give the 5-(2-fluorophenyl)-5-methylimidazolidine-2,4-dione (40.4 g, 194 mmol, 97.0% yield) as a white solid. MS (ISN): m/z=207.5 $[M-H]^-$.

Synthesis of Intermediates A6

A6a: (RS)-2-Amino-2-(3-bromo-phenyl)-propionic acid methyl ester

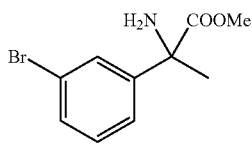

A dispersion of (RS)-5-(3-bromo-phenyl)-5-methyl-imidazolidine-2,4-dione (12.81 g, 48 mmol) in 6 N sodium hydroxide solution (95.23 ml) was heated to reflux for 48 h. For the workup, the reaction mixture was cooled with ice and treated with hydrochloric acid (36.5%) until pH 1 was reached. The mixture was evaporated to dryness at reduced pressure. The crude (RS)-2-amino-2-(3-bromo-phenyl)-propionic acid hydrochloride was dispersed in methanol (500 ml) and cooled to 0° C. Within 12 minutes and under ice cooling, thionylchloride (18.02 ml, 246 mmol) was added dropwise. After complete addition, the reaction mixture was heated to reflux for 60 h. For the workup, the reaction mixture was cooled to room temperature and evaporated at reduced pressure. The white residue was treated with a mixture of water and ice (200 ml), triethylamine (16.5 ml), and diethylether (500 ml). The resulting suspension was filtrated over Dicalit; thereafter the aqueous layer was separated and re-extracted with diethylether (250 ml). The combined organic layers were washed with saturated sodium chloride solution (250 ml), dried over sodium sulfate, and evaporated at reduced pressure. There were obtained 9.39 g (76.7% of theory) of (RS)-2-amino-2-(3-bromo-phenyl)-propionic acid methyl ester as a light yellow oil. The purity of the product allowed using it in the next step without further purification. Mass (calculated) $C_{10}H_{12}BrNO_2$ [258.117]; (found) $[M+H]^+=258$, 260.

A6b: (RS)-2-Amino-2-(5-bromo-2-fluoro-phenyl)-propionic acid methylester

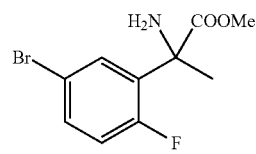

The hydrolysis of the (RS)-5-(5-bromo-2-fluoro-phenyl)-5-methyl-imidazolidine-2,4-dione with 6 N sodium hydroxide solution and esterification of the resulting (RS)-2-amino-2-(5-bromo-2-fluoro-phenyl)-propionic acid with methanol and thionylchloride yielded the (RS)-2-amino-2-(5-bromo-2-fluoro-phenyl)-propionic acid methylester as a light yellow oil. The purity of the product allowed using it in the next step without further purification. Mass (calculated) $C_{10}H_{11}BrFNO_2$ [276.107]; (found) $[M+H]^+=276$, 278.

A6c: (RS)-2-Amino-2-(2-fluoro-phenyl)-propionic acid methylester

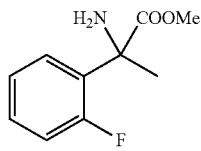

The hydrolysis of the (RS)-5-(2-fluoro-phenyl)-5-methyl-imidazolidine-2,4-dione with 3 N sodium hydroxide solution and esterification of the resulting (RS)-2-amino-2-(2-fluoro-phenyl)-propionic acid with methanol and thionylchloride yielded the (RS)-2-amino-2-(2-fluoro-phenyl)-propionic acid methylester as a light yellow liquid. The purity of the product allowed using it in the next step without further purification. MS (ISP): m/z=198.2 $[M+H]^+$.

A6d: (R)-2-Amino-2-(5-bromo-2-fluoro-phenyl)-propionic acid methyl ester

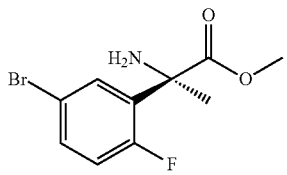

A mixture of (R)-N-((R)-1-(5-bromo-2-fluorophenyl)-1-cyanoethyl)-2-methylpropane-2-sulfinamide (8.869 g, 25.54 mmol) in conc. hydrochloric acid (90 ml, 1078 mmol) was stirred at 23° C. for 4 h, then cooled to 0° C. and treated with 32% sodium hydroxide solution (120 ml, 1277 mmol), diluted with water (100 ml) and extracted with ethyl acetate (1×300 ml and 2×200 ml). The combined organic layers were dried over $Na_2SO_4$, filtered and the solvent was removed in vacuum to leave the amide (intermediate A29) as an off-white solid. Dissolved in methanol (100 ml) and cautiously added conc. sulfuric acid (21.39 ml, 383 mmol), the mixture was stirred at reflux for 40 h, cooled to 0° C. and neutralized with sat. $Na_2CO_3$-sol. until pH 9 was reached. Extracted with ethyl acetate (3×100 ml), the combined organic layers were dried over Na2SO4, filtered and the solvent was removed in vacuum to give the (R)-methyl 2-amino-2-(5-bromo-2-fluorophenyl)propanoate (5.17 g, 73%) as a light yellow oil which was used without further purification. MS (ISP): m/z=276.1 $[M+H]^+$ and 278.0 $[M+2+H]^+$.

Synthesis of Intermediates A7

A7a: (RS)-2-Amino-2-(3-bromo-phenyl)-propan-1-ol

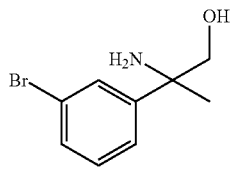

A solution of the (RS)-2-amino-2-(3-bromo-phenyl)-propionic acid methyl ester (9.39 g, mmol) in tetrahydrofuran (360 ml) was treated portionwise at −5° C. with lithiumaluminiumhydride (1.41 g, 36 mmol; 282 mg/2 min). After complete addition, stiffing was continued at 0-5° C. for 30 minutes. For the workup, the reaction mixture was cooled to −7° C., and water (9 ml) was added dropwise. Thereafter, 2 N sodium hydroxide solution (9 ml) was added and stirring continued for 15 minutes at room temperature. They grey suspension was filtrated through Dicalite which was washed with tetrahydrofuran (200 ml). The filtrate was evaporated at reduced pressure. There were obtained 8.67 g of crude (RS)-2-amino-2-(3-bromo-phenyl)-propan-1-ol as colorless oil. The purity of the product allowed using it in the next step without further purification. Mass (calculated) $C_9H_{12}BrNO$ [230.106]; (found) $[M+H]^+$=230, 232.

A7b: (RS)-2-Amino-2-(5-bromo-2-fluoro-phenyl)-propan-1-ol

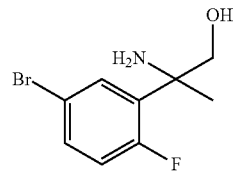

The reduction of the (RS)-2-amino-2-(5-bromo-2-fluorophenyl)-propionic acid methylester with lithiumaluminiumhydride in tetrahydrofuran yielded the (RS)-2-amino-2-(5-bromo-2-fluoro-phenyl)-propan-1-ol as a light yellow oil. The purity of the product allowed using it in the next step without further purification. Mass (calculated) $C_9H_{11}BrFNO$ [248.097]; (found) $[M+H]^+$=248, 250.

A7c: (RS)-2-Amino-2-(2-fluoro-phenyl)-propan-1-ol

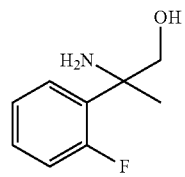

The reduction of the (RS)-2-amino-2-(2-fluoro-phenyl)-propionic acid methylester with lithiumaluminiumhydride in diethyl ether yielded the (RS)-2-amino-2-(2-fluoro-phenyl)-propan-1-ol as a light yellow oil. The purity of the product allowed using it in the next step without further purification. MS (ISP): m/z=170.3 $[M+H]^+$.

A7d: (R)-2-Amino-2-(5-bromo-2-fluorophenyl)propan-1-ol

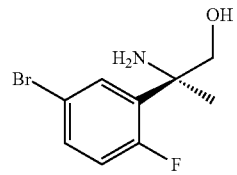

To a solution of (R)-methyl 2-amino-2-(5-bromo-2-fluorophenyl)propanoate (3.95 g, 14.3 mmol, Eq: 1.00) in diethyl ether (120 ml) was added at 0° C. lithium aluminum hydride (652 mg, 17.2 mmol, Eq: 1.2) in five portions. The icebath was removed and stirring continued at room temperature for 2 hours. To the cooled reaction mixture was added dropwise water (652 mg, 652 μl, 36.2 mmol, Eq: 2.53), NaOH (15% in water) (572 mg, 652 μl, 14.3 mmol, Eq: 1.00) and water (1.96 g, 1956 μl, 109 mmol, Eq: 7.59) via syringe (1:1:3 system) and the mixture was stirred for 20 min until a white suspension occurred. Three small spoons of $Na_2SO_4$ were added to the mixture, which was filtered after 5 min. The colourless ether solution was evaporated to give (R)-2-amino-2-(5-bromo-2-fluorophenyl)propan-1-ol Synthesis of Intermediates A8

A8a: (R)-Benzyl 2-(5-bromo-2-fluorophenyl)-1-hydroxypropan-2-ylcarbamate

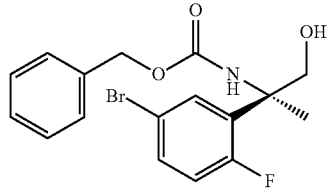 [SMILES: C[C@@](CO)(NC(=O)OCc1ccccc1)c1cc(Br)ccc1F]

(3.2 g, 12.9 mmol, 90.2% yield) as a white solid which was used in the next step without further purification. MS (ISP): m/z=248.1 [M+H]$^+$ and 250.0 [M+2+H]$^+$.

To a solution of (R)-2-amino-2-(5-bromo-2-fluorophenyl) propan-1-ol (1.97 g, 7.94 mmol, Eq: 1.00) in tetrahydrofuran (10.6 ml) and sat. aqueous sodium bicarbonate solution (1.02 g, 10.7 ml, 12.2 mmol, Eq: 1.53) at room temperature was added benzyl chloroformate (Cbz-Cl) (2.03 g, 1.7 ml, 11.9 mmol, Eq: 1.5) and the mixture was stirred at room temperature for 3 hours. Poured into sat. NaHCO$_3$-sol., extracted with ethyl acetate, the organic layer was dried over Na$_2$SO$_4$. Removal of the solvent in vacuum left of a yellow oil which was purified by flash chromatography (silica gel, 50 g, 0% to 35% EtOAc in heptane) to give the (R)-benzyl 2-(5-bromo-2-fluorophenyl)-1-hydroxypropan-2-ylcarbamate (2.16 g, 5.65 mmol, 71.2% yield) as an off-white solid. MS (ISP): m/z=382.2 [M+H]$^+$ and 384.2 [M+2+H]$^+$.

A8b: (RS)-Benzyl 2-(2-fluorophenyl)-1-hydroxypropan-2-ylcarbamate

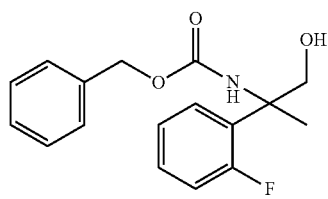 [SMILES: CC(CO)(NC(=O)OCc1ccccc1)c1ccccc1F]

To a vigorously stirred mixture of 2-amino-2-(2-fluorophenyl)propan-1-ol (10.57 g, 62.5 mmol, Eq: 1.00) and sodium bicarbonate (10.5 g, 125 mmol, Eq: 2.00) in dichloromethane (35.0 ml) and water (35.0 ml) at 0° C. was added benzyl chloroformate (16.0 g, 13.4 ml, 93.7 mmol, Eq: 1.50) and the mixture was stirred at 0° C. slowly warming up to 23° C. over night. Poured into brine, extracted twice with ethyl acetate, dried combined organic layer over Na$_2$SO$_4$. Filtration and removal of the solvent in vacuum left a light yellow liquid which was purified by flash chromatography (silica gel, 100 g, 0% to 30% EtOAc in heptane) to give the (RS)-benzyl 2-(2-fluorophenyl)-1-hydroxypropan-2-ylcarbamate (10.46 g, 34.5 mmol, 55.2% yield) as a colorless liquid. MS (ISP): m/z=304.2 [M+H]$^+$.

A8c: (R)-Benzyl 2-(2-fluorophenyl)-1-hydroxypropan-2-ylcarbamate

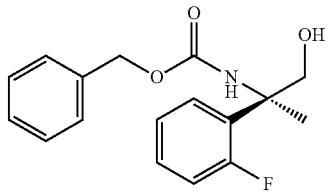 [SMILES: C[C@@](CO)(NC(=O)OCc1ccccc1)c1ccccc1F]

To a vigorously stirred mixture of commercially available (R)-2-amino-2-(2-fluorophenyl)propan-1-ol hydrochloride (20 g, 97.2 mmol, Eq: 1.00) [CAS-no. 1213310-23-6 (as HCl salt 1391434-81-3)] and sodium bicarbonate (8.17 g, 97.2 mmol, Eq: 1.00) in tetrahydrofuran (108 ml) and sodium bicarbonate sat. solution (10.4 g, 108 ml, 123 mmol, Eq: 1.27) at 23° C. was dropwise added benzyl chloroformate (Cbz-Cl) (24.9 g, 20.8 ml, 146 mmol, Eq: 1.5) and the mixture was stirred at 23° C. for 3 h. Poured into sat NaHCO$_3$-sol., extracted with ethyl acetate, the organic layer was washed with brine, the combined aqueous layer was reextracted with ethyl acetate and the combined organic layer was dried over Na$_2$SO$_4$. Filtration and removal of the solvent in vacuum left of a yellow oil which was purified by flash chromatography (silica gel, 100 g, 0% to 35% EtOAc in heptane) to give the (R)-benzyl 2-(2-fluorophenyl)-1-hydroxypropan-2-ylcarbamate (28.78 g, 94.9 mmol, 97.6% yield) as a colorless oil which crystallized to a white solid. MS (ISP): m/z=304.2 [M+H]$^+$.

Synthesis of Intermediates A9

A9a: (R)-4-(5-Bromo-2-fluoro-phenyl)-4-methyl-2-oxo-aλ4-[1,2,3]oxathiazolidine-3-carboxylic acid benzylester

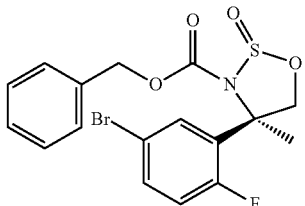

A solution of (R)-benzyl 2-(5-bromo-2-fluorophenyl)-1-hydroxypropan-2-ylcarbamate (2.37 g, 6.2 mmol, Eq: 1.00) in acetonitrile (5 ml) was dropwise added to a stirred solution of thionyl chloride (1.84 g, 1.13 ml, 15.5 mmol, Eq: 2.5) in acetonitrile (25.0 ml) at 40° C., and the mixture was stirred at 40° C. for 1 hour before pyridine (2.45 g, 2.51 ml, 31.0 mmol, Eq: 5) was dropwise added. The reaction was allowed to warm to room temperature and stirred over night. Evaporated totally, added ether and filtered the solid off. Washed the organic layer once with 0.5 M HCl, once with brine, the organic layer was dried over Na$_2$SO$_4$. Removal of the solvent in vacuum left the (R)-4-(5-bromo-2-fluoro-phenyl)-4-methyl-2-oxo-2λ4-[1,2,3]oxathiazolidine-3-carboxylic acid benzylester (2.66 g, 6.21 mmol, 100% yield) as a light yellow oil. MS (ISN): m/z=426.3 [M−H]$^−$ and 428.3 [M+2−H]$^−$.

A9b: (RS)-4-(2-Fluoro-phenyl)-4-methyl-2-oxo-2λ4-[1,2,3]oxathiazolidine-3-carboxylic acid benzyl ester

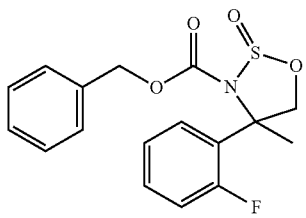 [SMILES: CC1(c2ccccc2F)COS(=O)N1C(=O)OCc1ccccc1]

A solution of benzyl 2-(2-fluorophenyl)-1-hydroxypropan-2-ylcarbamate (10.35 g, 34.1 mmol, Eq: 1.00) in acetonitrile (30 ml) was dropwise added to a stirred solution of thionyl chloride (10.1 g, 6.23 ml, 85.3 mmol, Eq: 2.5) in acetonitrile (150 ml) at 40° C., and the mixture was stirred at 40° C. for 1 hour before pyridine (13.5 g, 13.8 ml, 171 mmol, Eq: 5) was dropwise added and the reaction was allowed to warm to room temperature and stirred over night. Evaporated totally, added ether and filtered the solid off, washed the organic layer once with 0.5 M HCl, once with brine, the organic layer was dried over $Na_2SO_4$. Removal of the solvent in vacuum left the (RS)-4-(2-fluoro-phenyl)-4-methyl-2-oxo-2λ4-[1,2,3]oxathiazolidine-3-carboxylic acid benzyl ester (11.42 g, 32.7 mmol, 95.8% yield) as a colorless oil. MS (ISP): m/z=367.2 [M+NH4]+.

A9c: (R)-4-(2-Fluoro-phenyl)-4-methyl-2-oxo-2λ4-[1,2,3]oxathiazolidine-3-carboxylic acid benzyl ester

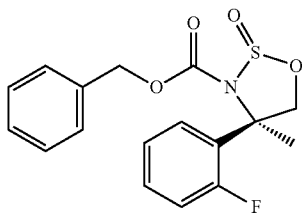 [SMILES: C[C@@]1(c2ccccc2F)COS(=O)N1C(=O)OCc1ccccc1]

To a solution of thionyl chloride (28.2 g, 17.3 ml, 237 mmol, Eq: 2.5) in acetonitrile (417 ml) at −40° C. was dropwise a solution of (R)-benzyl 2-(2-fluorophenyl)-1-hydroxypropan-2-ylcarbamate (28.75 g, 94.8 mmol, Eq: 1.00) in acetonitrile (83.3 ml), the mixture was stirred at 40° C. for 1 h then pyridine (37.5 g, 38.3 ml, 474 mmol, Eq: 5) was dropwise added and the reaction was allowed to warm to 23° C. and stirred for 20 h. All volatiles were removed in vacuum, added diethyl ether, the solid was filtered off, the organic layer was washed with 0.5 M HCl and brine, dried over $Na_2SO_4$. Filtration and removal of the solvent in vacuum left the crude (R)-4-(2-fluoro-phenyl)-4-methyl-2-oxo-2λ4-[1,2,3]oxathiazolidine-3-carboxylic acid benzyl ester (29.2 g, 83.6 mmol, 88.2% yield) as a colorless oil which was used without further purification. MS (ISP): m/z=348.3 [M+H]+.

Synthesis of Intermediates A10

A10a: (R)-4-(5-Bromo-2-fluoro-phenyl)-4-methyl-2,2-dioxo-λ6-[1,2,3]oxathiazolidine-3-carboxylic acid benzyl ester

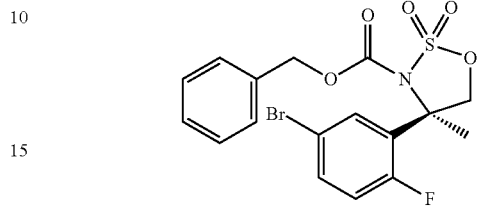

To a solution of (R)-4-(5-bromo-2-fluoro-phenyl)-4-methyl-2-oxo-2λ4-[1,2,3]oxathiazolidine-3-carboxylic acid benzylester (2.67 g, 6.23 mmol, Eq: 1.00) in ethyl acetate (20 ml), acetonitrile (20.0 ml) and water (30.0 ml) at room temperature was added sodium periodate (2.00 g, 9.35 mmol, Eq: 1.5) followed by ruthenium(III) chloride hydrate (14.1 mg, 62.3 µmol, Eq: 0.01) and the mixture was stirred at room temperature for 1.5 h. Poured into water, extracted with ethyl acetate, the organic layer was dried over $Na_2SO_4$. Removal of the solvent in vacuum left a dark oil which was purified by flash chromatography (silica gel, 50 g, 0% to 100% ethyl acetate in heptane) to give the (R)-4-(5-bromo-2-fluoro-phenyl)-4-methyl-2,2-dioxo-2λ6-[1,2,3]oxathiazolidine-3-carboxylic acid benzyl ester (2.443 g, 5.5 mmol, 88.2% yield) as a colorless oil. MS (ISN): m/z=488.2 [M+HCO2]− and 490.2 [M+2 HCO2]−.

A10b: (RS)-4-(2-Fluoro-phenyl)-4-methyl-2,2-dioxo-2λ6-[1,2,3]oxathiazolidine-3-carboxylic acid benzyl ester

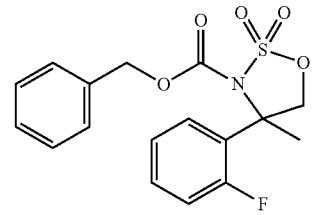 [SMILES: CC1(c2ccccc2F)COS(=O)(=O)N1C(=O)OCc1ccccc1]

To a solution of 4-(2-fluoro-phenyl)-4-methyl-2-oxo-2λ4-[1,2,3]oxathiazolidine-3-carboxylic acid benzyl ester (11.42 g, 32.7 mmol, Eq: 1.00) in ethyl acetate (100 ml), acetonitrile (100 ml) and water (150 ml) at 0° C. was added sodium periodate (10.5 g, 49.0 mmol, Eq: 1.5) followed by ruthenium(III) chloride hydrate (73.7 mg, 327 µmol, Eq: 0.01) and the mixture was stirred at room temperature for 2 hours. Poured into water, extracted with ethyl acetate, the organic layer was dried over $Na_2SO_4$. Removal of the solvent in vacuum left a black oil which was purified by flash chromatography (silica gel, 100 g, 0% to 35% ethyl acetate in heptane) to give the (RS)-4-(2-fluoro-phenyl)-4-methyl-2,2-dioxo-2λ6-[1,2,3]oxathiazolidine-3-carboxylic acid benzyl ester (10.36 g, 28.4 mmol, 86.7% yield) as a colorless oil. MS (ISP): m/z=383.1 [M+NH4]+.

A10c: (R)-4-(2-Fluoro-phenyl)-4-methyl-2,2-dioxo-2λ⁶-[1,2,3]oxathiazolidine-3-carboxylic acid benzyl ester

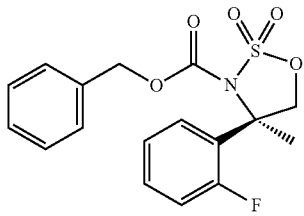 [SMILES: C[C@@]1(c2ccccc2F)COS(=O)(=O)N1C(=O)OCc1ccccc1]

To a solution of (R)-4-(2-fluoro-phenyl)-4-methyl-2-oxo-2λ4-[1,2,3]oxathiazolidine-3-carboxylic acid benzyl ester (29.2 g, 83.6 mmol, Eq: 1.00) in ethyl acetate (239 ml), acetonitrile (239 ml) and water (358 ml) at 5° C. was added sodium periodate (26.8 g, 125 mmol, Eq: 1.5) followed by ruthenium(III) chloride hydrate (188 mg, 836 µmol, Eq: 0.01) and the mixture was stirred at 23° C. for 1.75 h. Poured into water, extracted with ethyl acetate, the organic layer was washed with brine, the combined organic layer was reextracted with ethyl acetate and the combined organic layer was dried over Na₂SO₄. Filtration and removal of the solvent in vacuum left a black oil which was purified by flash chromatography (silica gel, 100 g, 0% to 35% EtOAc in heptane) to give the (R)-4-(2-fluoro-phenyl)-4-methyl-2,2-dioxo-2λ⁶-[1,2,3]oxathiazolidine-3-carboxylic acid benzyl ester (26.45 g, 72.4 mmol, 86.6% yield) as a colorless oil. MS (ISP): m/z=383.1 [M+NH₄]⁺.

Synthesis of Intermediates A11

A11a: (R)-S-2-(Benzyloxycarbonylamino)-2-(5-bromo-2-fluorophenyl)propyl ethanethioate

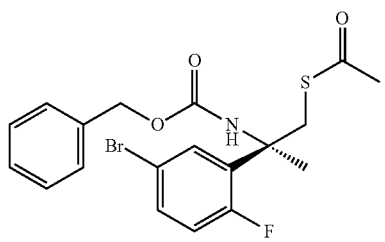 [SMILES: CC(=O)SC[C@](C)(NC(=O)OCc1ccccc1)c1cc(Br)ccc1F]

To a solution of (R)-4-(5-bromo-2-fluoro-phenyl)-4-methyl-2,2-dioxo-2λ⁶-[1,2,3]oxathiazolidine-3-carboxylic acid benzyl ester (2.443 g, 5.5 mmol, Eq: 1.00) in N,N-dimethylformamide (11 ml) at room temperature was added potassium thioacetate (942 mg, 8.25 mmol, Eq: 1.5) and the mixture was stirred at room temperature for 30 min. Evaporated the DMF at high vacuum and residue was vigorously stirred in dichloromethane (22.0 ml) and sulfuric acid (20% in water) (40.4 g, 22.0 ml, 82.5 mmol, Eq: 15) at room temperature over night. Poured into sat NaCl-sol., extracted with ethyl acetate, the organic layer was dried over Na₂SO₄. Removal of the solvent in vacuum left a yellow oil which was purified by flash chromatography (silica gel, 50 g, 0% to 40% EtOAc in heptane) to give the (R)-S-2-(benzyloxycarbonylamino)-2-(5-bromo-2-fluorophenyl)propyl eth- anethioate (2.217 g, 5.03 mmol, 91.6% yield) as a light yellow oil. MS (ISP): m/z=457.9 [M+NH₄]⁺ and 458.9 [M+2+NH₄]⁺.

A11b: (RS)-S-2-(Benzyloxycarbonylamino)-2-(2-fluorophenyl)propyl ethanethioate

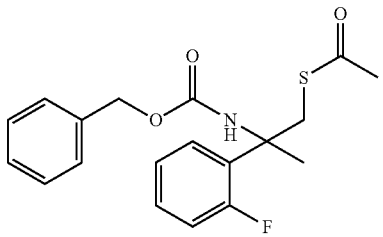 [SMILES: CC(=O)SCC(C)(NC(=O)OCc1ccccc1)c1ccccc1F]

To a solution of (RS)-4-(2-fluoro-phenyl)-4-methyl-2,2-dioxo-2λ⁶-[1,2,3]oxathiazolidine-3-carboxylic acid benzyl ester (907 mg, 2.48 mmol, Eq: 1.00) in N,N-dimethylformamide (5.01 ml) at 23° C. was added potassium thioacetate (425 mg, 3.72 mmol, Eq: 1.5) and the mixture was stirred at 23° C. for 1.5 h. The DMF was evaporated to give a red oil, dissolved in dichloromethane (10.0 ml), added sulfuric acid (20% in H₂O) (18.3 g, 9.92 ml, 37.2 mmol, Eq: 15) and vigorously stirred at 23° C. for 16 h. Partitioned between water and ethyl acetate, washed organic layer with sat. NaHCO₃-sol. and dried over Na₂SO₄. Filtration and removal of the solvent in vacuum left an orange oil which was purified by flash chromatography (silica gel, 50 g, 0% to 30% EtOAc in heptane) to give the (RS)-S-2-(benzyloxycarbonylamino)-2-(2-fluorophenyl)propyl ethanethioate (851 mg, 2.35 mmol, 94.9% yield) as an orange oil. MS (ISP): m/z=407.3 [M+HCO₂H]⁺.

A11c: (R)-S-2-(Benzyloxycarbonylamino)-2-(2-fluorophenyl)propyl ethanethioate

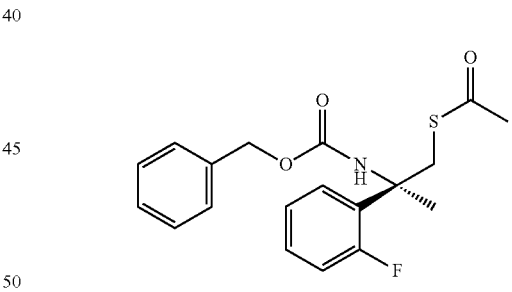

To a solution of (R)-4-(2-fluoro-phenyl)-4-methyl-2,2-dioxo-2λ⁶-[1,2,3]oxathiazolidine-3-carboxylic acid benzyl ester (11.69 g, 32.0 mmol, Eq: 1.00) in N,N-dimethylformamide (64.6 ml) at 23° C. was added potassium thioacetate (5.48 g, 48.0 mmol, Eq: 1.5) and the mixture was stirred at 23° C. for 0.5 h. The DMF was evaporated in high vacuum to give an orange oil, dissolved in dichloromethane (129 ml), added sulfuric acid (20% in H₂O) (235 g, 128 ml, 480 mmol, Eq: 15) and vigorously stirred at 23° C. for 18 h. Partitioned between brine and ethyl acetate, reextracted the aqueous layer with ethyl acetate, washed the combined organic layer with sat. NaHCO₃-sol. and brine and dried over Na₂SO₄. Filtration and removal of the solvent in vacuum left an orange oil which was purified by flash chromatography (silica gel, 70 g, 0% to 25% EtOAc in heptane) to give the (R)-S-2-(benzyloxycarbonylamino)-2-

(2-fluorophenyl)propyl ethanethioate (11.22 g, 31.0 mmol, 97.0% yield) as an orange oil. MS (ISP): m/z=362.2 [M+H]⁺.

Synthesis of Intermediates A12

A12a: Benzyl (2¹⁶)-1-(chlorosulfinyl)-2-(2-fluorophenyl)propan-2-ylcarbamate

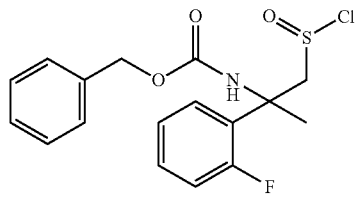 [SMILES: CC(CS(=O)Cl)(NC(=O)OCc1ccccc1)c1ccccc1F]

To a solution of S-2-(benzyloxycarbonylamino)-2-(2-fluorophenyl)propyl ethanethioate (8.76 g, 24.2 mmol, Eq: 1.00) in dichloromethane (dry) (37.3 ml) at 20° C. was added acetic anhydride (2.47 g, 2.29 ml, 24.2 mmol, Eq: 1.00) and sulfuryl chloride (6.54 g, 3.94 ml, 48.5 mmol, Eq: 2.00) and the mixture was stirred at 30° C. to 5° C. for 1 h. All volatiles were removed in vacuum and the residue was dried in high vacuum to give the crude benzyl (2RS)-1-(chlorosulfinyl)-2-(2-fluorophenyl)propan-2-ylcarbamate (9.144 g, 24.7 mmol, 102% yield) as a yellow oil which was used without further purification.

A12b: Benzyl (2R)-1-(chlorosulfinyl)-2-(2-fluorophenyl)propan-2-ylcarbamate

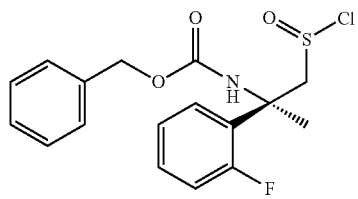 [SMILES: C[C@@](CS(=O)Cl)(NC(=O)OCc1ccccc1)c1ccccc1F]

To a solution of (R)-S-2-(benzyloxycarbonylamino)-2-(2-fluorophenyl)propyl ethanethioate (11.22 g, 31.0 mmol, Eq: 1.00) in dichloromethane (dry) (47.8 ml) at 20° C. was added acetic anhydride (3.17 g, 2.93 ml, 31.0 mmol, Eq: 1.00) and sulfuryl chloride (8.38 g, 5.05 ml, 62.1 mmol, Eq: 2.00) and the mixture was stirred at 30° C. to −5° C. for 1 h. All volatiles were removed in vacuum and the residue was dried in high vacuum to give the crude benzyl (2R)-1-(chlorosulfinyl)-2-(2-fluorophenyl)propan-2-ylcarbamate (11.85 g, 31.1 mmol, 100% yield) as a yellow oil which was used without further purification.

Synthesis of Intermediates A13

A13a: Benzyl (2¹⁶)-1-(N-allylsulfinamoyl)-2-(2-fluorophenyl)propan-2-ylcarbamate

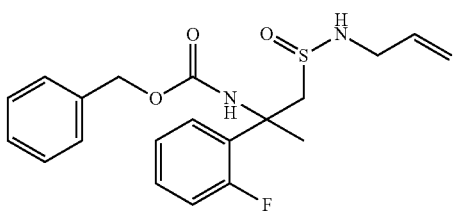 [SMILES: C=CCNS(=O)CC(C)(NC(=O)OCc1ccccc1)c1ccccc1F]

To a solution of benzyl (2RS)-1-(chlorosulfinyl)-2-(2-fluorophenyl)propan-2-ylcarbamate (4.09 g, 11.1 mmol, Eq: 1.00) in dichloromethane (dry) (44.2 ml) at −78° C. was quickly added prop-2-en-1-amine (1.58 g, 2.08 ml, 27.6 mmol, Eq: 2.5), the cooling bath was removed and the mixture was stirred at −78 to 0° C. for 2.5 h. Poured into brine, extracted with ethyl acetate, dried organic layer over Na₂SO₄. Filtration and removal of the solvent in vacuum left a yellow oil which was purified by flash chromatography (silica gel, 50 g, 0% to 100% EtOAc in heptane) to give the benzyl (2RS)-1-(N-allylsulfinamoyl)-2-(2-fluorophenyl)propan-2-ylcarbamate (2.87 g, 7.35 mmol, 66.5% yield) as a light yellow gum. MS (ISP): m/z=391.3 [M+H]⁺.

A13b: Benzyl (2R)-1-(N-allylsulfinamoyl)-2-(2-fluorophenyl)propan-2-ylcarbamate

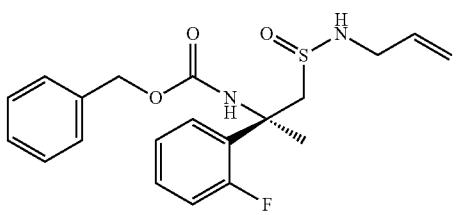 [SMILES: C=CCNS(=O)C[C@](C)(NC(=O)OCc1ccccc1)c1ccccc1F]

To a solution of benzyl (2R)-1-(chlorosulfinyl)-2-(2-fluorophenyl)propan-2-ylcarbamate (5.10 g, 13.8 mmol, Eq: 1.00) in dichloromethane (dry) (55.2 ml) at −78° C. was quickly added prop-2-en-1-amine (1.97 g, 2.59 ml, 34.5 mmol, Eq: 2.5), the cooling bath was removed and the mixture was stirred at −78 to 0° C. for 1.5 h. Poured into brine, extracted with ethyl acetate, dried organic layer over Na₂SO₄. Filtration and removal of the solvent in vacuum left a yellow oil which was purified by flash chromatography (silica gel, 50 g, 0% to 100% EtOAc in heptane) to give the benzyl (2R)-1-(N-allylsulfinamoyl)-2-(2-fluorophenyl)propan-2-ylcarbamate (3.737 g, 9.57 mmol, 69.4% yield) as a light yellow gum. MS (ISP): m/z=391.3 [M+H]⁺.

A13c: Benzyl 02R)-2-(2-fluorophenyl)-1-(N-((S)-1,1,1-trifluorobut-3-en-2-yl)sulfinamoyl)propan-2-yl)carbamate

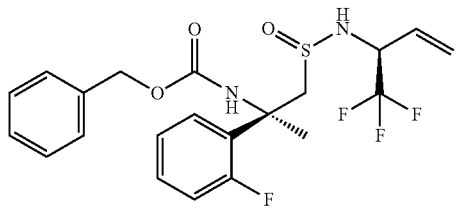 [SMILES: C=C[C@H](NS(=O)C[C@](C)(NC(=O)OCc1ccccc1)c1ccccc1F)C(F)(F)F]

To a solution of (S)-1,1,1-trifluorobut-3-en-2-amine hydrochloride (4.15 g, 25.7 mmol, Eq: 0.95) in DMF (40 ml) at −78° C., was added N-methylmorpholine (8.2 g, 8.92 ml, 81.1 mmol, Eq: 3) and stirred at −78° C. for 30 minutes. Then a solution of benzyl (2R)-1-(chlorosulfinyl)-2-(2-fluorophenyl)propan-2-ylcarbamate (10 g, 27 mmol, Eq: 1.00) in dichloromethane (dry) (30 ml) at −78° C. was added and the mixture was stirred at −78 to 23° C. for 18 h. Poured into brine, extracted with ethyl acetate, dried organic layer over Na$_2$SO$_4$. Poured into brine, extracted with EtOAc, dried the organic layer over Na$_2$SO$_4$. Filtration and removal of the solvent in vacuum left a yellow oil which was purified by flash chromatography (silica gel, 50 g, 0% to 50% EtOAc in heptane) to give the benzyl ((2R)-2-(2-fluorophenyl)-1-(N-((S)-1,1,1-trifluorobut-3-en-2-yl)sulfinamoyl)propan-2-yl)carbamate (7.92 g, 17.3 mmol, 63.9% yield) as a light brown oil. MS (ISP): m/z=459.3 [M+H]$^+$.

A13d: Benzyl ((2R)-1-(N-(2,2-difluoro-3-hydroxypropyl)sulfinamoyl)-2-(2-fluorophenyl)propan-2-yl)carbamate

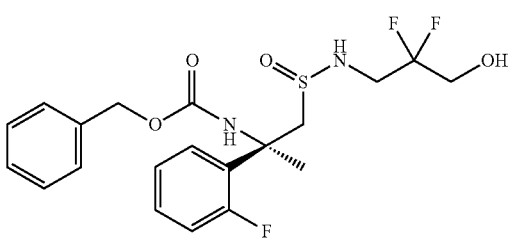 [SMILES: C[C@@](CS(=O)NCC(F)(F)CO)(NC(=O)OCc1ccccc1)c1ccccc1F]

To a solution of 3-amino-2,2-difluoropropan-1-ol hydrochloride (1.2 g, 8.11 mmol, Eq: 1) in DMF (15 ml) at 0° C., was added N-methylmorpholine (2.46 g, 2.68 ml, 24.3 mmol, Eq: 3) and stirred at 0° C. for 10 minutes. Then a solution of benzyl (2R)-1-(chlorosulfinyl)-2-(2-fluorophenyl)propan-2-ylcarbamate (3 g, 8.11 mmol, Eq: 1) in dichloromethane (dry) (5 ml) at 0° C. was added and the mixture was stirred at 23° C. for 16 h. Poured into brine, extracted with ethyl acetate, dried organic layer over Na$_2$SO$_4$. Poured into brine, extracted with EtOAc, dried the organic layer over Na$_2$SO$_4$. Filtration and removal of the solvent in vacuum left a yellow oil which was purified by flash chromatography (silica gel, 50 g, 0% to 100% EtOAc in heptane) to give the benzyl ((2R)-1-(N-(2,2-difluoro-3-hydroxypropyl) sulfinamoyl)-2-(2-fluorophenyl)propan-2-yl) carbamate (1.7 g, 3.82 mmol, 47.2% yield) as a light yellow foam. MS (ISP): m/z=445.3 [M+H]$^+$.

Synthesis of Intermediates A14

A14a: (RS)-[1-(2-Fluoro-phenyl)-1-methyl-2-(1-oxo-3,6-dihydro-2H-1λ$^6$-[1,2,7]thiadiazepin-1-yl)-ethyl]-carbamic acid benzyl ester

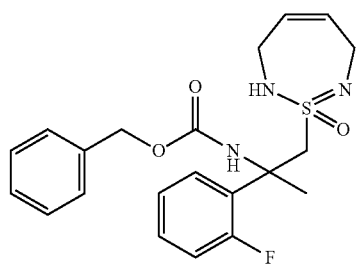 [SMILES: CC(CS1(=O)=NCC=CCN1)(NC(=O)OCc1ccccc1)c1ccccc1F]

a) Benzyl (RS)-1-(N,N'-diallylsulfamimidoyl)-2-(2-fluorophenyl)propan-2-ylcarbamate: To a solution of benzyl (RS)-1-(N-allylsulfinamoyl)-2-(2-fluorophenyl)propan-2-ylcarbamate (2.5 g, 6.4 mmol, Eq: 1.00) in dichloromethane (dry) (42.7 ml) at −78° C. was added tert-butyl hypochlorite (730 mg, 760 µl, 6.72 mmol, Eq: 1.05) and the mixture was stirred at −78° C. for 45 min. Then prop-2-en-1-amine (1.1 g, 1.44 ml, 19.2 mmol, Eq: 3) was added, the cooling bath was removed and stirring was continued at −78 to 23° C. for 1 h. Poured into brine, extracted with ethyl acetate, dried the organic layer over Na$_2$SO$_4$. Filtration and removal of the solvent in vacuum left the crude benzyl (RS)-1-(N,N'-diallylsulfamimidoyl)-2-(2-fluorophenyl)propan-2-ylcarbamate (2.85 g, 6.4 mmol, 99.9% yield) as a light yellow oil which was used without further purification. MS (ISP): m/z=446.3 [M+H]$^+$.

b) (RS)-[1-(2-Fluoro-phenyl)-1-methyl-2-(1-oxo-3,6-dihydro-2H-1λ$^6$-[1,2,7]thiadiazepin-1-yl)-ethyl]-carbamic acid benzyl ester: To a solution of benzyl (RS)-1-(N,N'-diallylsulfamimidoyl)-2-(2-fluorophenyl)propan-2-ylcarbamate (2.85 g, 6.4 mmol, Eq: 1.00) in dichloromethane (dry) (183 ml) under argon atmosphere at 23° C. was added tricyclohexylphosphine[1,3-bis (2,4,6-trimethylphenyl)-4,5-dihydroimidazol-2-ylidene]ruthenium (II) (Grubbs II, Grubbs 2nd generation catalyst) (272 mg, 320 µmol, Eq: 0.05) and the mixture was refluxed for 5 h. Evaporated all volatiles and the crude material was purified by flash chromatography (silica gel, 50 g, 0% to 50% EtOAc in heptane) to give the (RS)-[1-(2-fluoro-phenyl)-1-methyl-2-(1-oxo-3,6-dihydro-2H-1λ$^6$-[1,2,7]thiadiazepin-1-yl)-ethyl]-carbamic acid benzyl ester (2.00 g, 4.79 mmol, 74.9% yield) as a brown gum. MS (ISP): m/z=418.3 [M+H]$^+$.

A14b: [(R)-1-(2-fluoro-phenyl)-1-methyl-2-(1-oxo-3,6-dihydro-2H-1λ$^6$-[1,2,7]thiadiazepin-1-yl)-ethyl]-carbamic acid benzyl ester

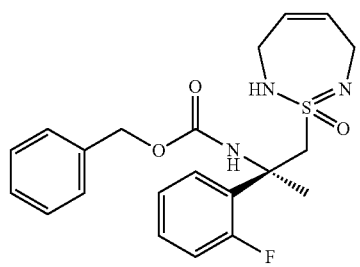 [SMILES: C[C@@](CS1(=O)=NCC=CCN1)(NC(=O)OCc1ccccc1)c1ccccc1F]

a) Benzyl (2R)-1-(N,N'-diallylsulfamimidoyl)-2-(2-fluorophenyl)propan-2-ylcarbamate: To a solution of benzyl (2R)-1-(N-allylsulfinamoyl)-2-(2-fluorophenyl)propan-2-ylcarbamate (3.73 g, 9.55 mmol, Eq: 1.00) in dichloromethane (dry) (63.7 ml) at −78° C. was added tert-butyl hypochlorite (1.09 g, 1.13 ml, 10.0 mmol, Eq: 1.05) and the mixture was stirred at −78° C. for 45 min (tlc indicated complete & clean conversion after 40 min). Then prop-2-en-1-amine (1.64 g, 2.15 ml, 28.7 mmol, Eq: 3) was added, the cooling bath was removed and stirring was continued at −78 to 23° C. for 1 h. Poured into brine, extracted with ethyl acetate, dried the organic layer over Na$_2$SO$_4$. Filtration and removal of the solvent in vacuum left the crude benzyl (2R)-1-(N,N'-diallylsulfamimidoyl)-2-(2-fluorophenyl)propan-2-ylcarbamate (4.01 g, 9.00 mmol, 94.2% yield) as a yellow oil which was used without further purification. MS (ISP): m/z=446.3 [M+H]$^+$.

b) [(R)-1-(2-Fluoro-phenyl)-1-methyl-2-(1-oxo-3,6-dihydro-2H-1λ$^6$-[1,2,7]thiadiazepin-1-yl)-ethyl]-carbamic acid benzyl ester: A solution of benzyl (2R)-1-(N,N'-diallylsulfamimidoyl)-2-(2-fluorophenyl)propan-2-ylcarbamate (4.01 g, 9.00 mmol, Eq: 1.00) in dichloromethane (180 ml) under argon atmosphere at 23° C. was degassed using ultrasonication and purging with argon for 10 min, then tricyclohexylphosphine[1,3-bis(2,4,6-trimethylphenyl)-4,5-dihydroimidazol-2-ylidene]ruthenium (II) (Grubbs II, Grubbs 2nd generation catalyst) (382 mg, 450 µmol, Eq: 0.05) was added and the mixture was refluxed for 24 h. Evaporated all volatiles and the crude material was purified by flash chromatography (silica gel, 70 g, 0% to 50% EtOAc in heptane) to give the [(R)-1-(2-fluoro-phenyl)-1-methyl-2-(1-oxo-3,6-dihydro-2H-1λ$^6$-[1,2,7]thiadiazepin-1-yl)-ethyl]-carbamic acid benzyl ester (2.89 g, 6.92 mmol, 76.9% yield) as a light brown foam. MS (ISP): m/z=418.2 [M+H]$^+$.

A14c: Benzyl 02R)-2-(2-fluorophenyl)-1-((6S)-1-oxido-6-(trifluoromethyl)-3,6-dihydro-2H-1,2,7-thiadiazepin-1-yl)propan-2-yl)carbamate

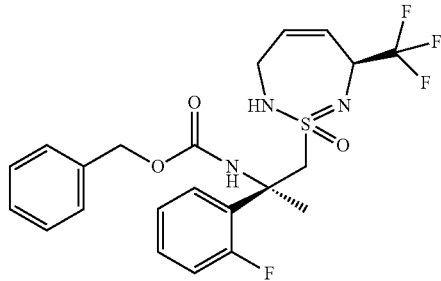 [SMILES: C[C@@](CS1(=O)=N[C@H](C(F)(F)F)C=CCN1)(NC(=O)OCc1ccccc1)c1ccccc1F]

a) benzyl ((2R)-1-(N-allyl-N'-((S)-1,1,1-trifluorobut-3-en-2-yl)sulfamimidoyl)-2-(2-fluorophenyl)propan-2-yl)carbamate: To a solution of benzyl ((2R)-2-(2-fluorophenyl)-1-(N-((S)-1,1,1-trifluorobut-3-en-2-yl)sulfinamoyl)propan-2-yl)carbamate (8.19 g, 17.9 mmol, Eq: 1) in dichloromethane (dry) (164 ml) at −78° C. was added tert-butyl hypochlorite (2.04 g, 2.12 ml, 10.0 mmol, Eq: 1.05) and the mixture was stirred at 0° C. for 1.5 h (tlc indicated complete conversion). Then prop-2-en-1-amine (3.06 g, 2.12 ml, 18.8 mmol, Eq: 3) was added, the cooling bath was removed and stiffing was continued at 23° C. for 18 h. Poured into brine, extracted with ethyl acetate, dried the organic layer over Na$_2$SO$_4$. Filtration and removal of the solvent in vacuum left the crude material which was purified by chromatography (silica gel, 100 g, 0 to 50% EtOAc in heptane) to give the benzyl ((2R)-1-(N-allyl-N'-((S)-1,1,1-trifluorobut-3-en-2-yl)sulfamimidoyl)-2-(2-fluorophenyl)propan-2-yl)carbamate (mixture of isomers) (7.16 g, 14.0 mmol, 78% yield) as a yellow oil. MS (ISP): m/z=514.3 [M+H]$^+$.

b) Benzyl ((2R)-2-(2-fluorophenyl)-1-((6S)-1-oxido-6-(trifluoromethyl)-3,6-dihydro-2H-1,2,7-thiadiazepin-1-yl)propan-2-yl)carbamate: A solution of benzyl ((2R)-1-(N-allyl-N'-((S)-1,1,1-trifluorobut-3-en-2-yl)sulfamimidoyl)-2-(2-fluorophenyl)propan-2-yl)carbamate (5.1 g, 9.93 mmol, Eq: 1) in dichloromethane (662 ml) under argon atmosphere at 23° C. was degassed using ultrasonication and purging with argon for 10 min, then tricyclohexylphosphine[1,3-bis(2,4,6-trimethylphenyl)-4,5-dihydroimidazol-2-ylidene]ruthenium (II) (Grubbs II, Grubbs 2nd generation catalyst) (422 mg, 497 µmol, Eq: 0.05) was added and the mixture was refluxed for 3 h. Evaporated all volatiles and the crude material was purified by flash chromatography (silica gel, 100 g, 0% to 50% EtOAc in heptane) to give the benzyl ((2R)-2-(2-fluorophenyl)-1-((6S)-1-oxido-6-(trifluoromethyl)-3,6-dihydro-2H-1,2,7-thiadiazepin-1-yl)propan-2-yl)carbamate (mixture of isomers) (4 g, 8.24 mmol, 83% yield) as a brown foam. MS (ISP): m/z=486.3 [M+H]$^+$.

A14d: Benzyl ((2R)-1-(4,4-difluoro-1-oxido-2,3,4,5-tetrahydro-1,2,6-thiadiazin-1-yl)-2-(2-fluorophenyl)propan-2-yl)carbamate

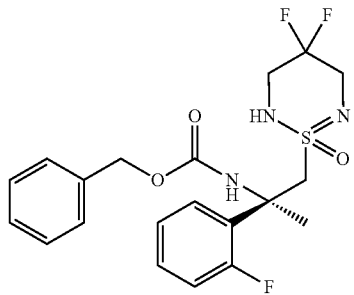 [SMILES: C[C@@](CS1(=O)=NCC(F)(F)CN1)(NC(=O)OCc1ccccc1)c1ccccc1F]

a) To a solution of benzyl ((2R)-1-(N-(2,2-difluoro-3-hydroxypropyl)sulfinamoyl)-2-(2-fluorophenyl)propan-2-yl)carbamate (1.2 g, 2.7 mmol, Eq: 1) and triethylamine (546 mg, 753 µl, 5.4 mmol, Eq: 2) in dichloromethane (24 ml) at 0° C. was added methanesulfonyl chloride (433 mg, 295 µl, 3.78 mmol, Eq: 1.4) and stirred at 23° C. for 3 h. Poured into sat. NaCl extracted with DCM, the organic layer was dried over Na$_2$SO$_4$. Filtration and removal of the solvent in vacuum left the crude material (520 mg) as a yellow oil which was purified by chromatography (silica gel, 20 g, 0% to 100% EtOAc in heptane) to give the [3-[[amino-[(2R)-2-amino-2-(2-fluorophenyl)propyl]-oxo-λ$^6$-sulfanylidene]amino]-2,2-difluoro-propyl]methanesulfonate (1.31 g, 2.51 mmol, 92.9% yield) as a light yellow foam. MS (ISP): m/z=521.3 [M+H]$^+$.

b) To a solution of [3-[[amino-[(2R)-2-amino-2-(2-fluorophenyl)propyl]-oxo-λ$^6$-sulfanylidene]amino]-2,2-difluoro-propyl]methanesulfonate (1.31 g, 2.51 mmol, Eq: 1) in dichloromethane (30 ml) at −78° C. was added tert-butyl hypochlorite (286 mg, 298 µl, 2.63 mmol, Eq: 1.05) and the mixture was stirred at 0° C. for 30 minutes. Dry ammonia gas was bubbled through the mixture for 10 min and stiffing was continued at 0° C. for 2.5 h. Extracted with water and DCM, dried the organic layer over $Na_2SO_4$. Filtration and removal of the solvent in vacuum left the crude [3-[[amino-[(2R)-2-(2-fluorophenyl)-2-(phenylmethoxycarbonylamino)propyl]-oxo-$\lambda^6$-sulfanylidene]amino]-2,2-difluoropropyl]methanesulfonate (1.25 g, 2.33 mmol, 92.8% yield) as a yellow foam. MS (ISP): m/z=538.2 [M+H]$^+$.

c) To a solution of [3-[[amino-[(2R)-2-(2-fluorophenyl)-2-(phenylmethoxycarbonylamino)propyl]-oxo-$\lambda^6$-sulfanylidene]amino]-2,2-difluoropropyl]methanesulfonate (1.25 g, 2.33 mmol, Eq: 1) in DMF (57.8 ml) was added cesium carbonate (758 mg, 2.33 mmol, Eq: 1) at 50° C. for 5 h. The mixture was extracted with brine, water and EtOAc, dried over $Na_2SO_4$, filtered and evaporated. The light yellow oil was purified by chromatography (silica gel, 20 g, 0% to 50% EtOAc in heptane) to give the benzyl ((2R)-1-(4,4-difluoro-1-oxido-2,3,4,5-tetrahydro-1,2,6-thiadiazin-1-yl)-2-(2-fluorophenyl)propan-2-yl)carbamate (mixture of isomers) (350 mg, 793 µmol, 34.1% yield) as a colorless oil. MS (ISP): m/z=442.3 [M+H]$^+$.

Synthesis of Intermediates A15

A15a: 1-(2-Fluoro-phenyl)-1-methyl-2-(1-oxo-3,4,5,6-tetrahydro-2H-1$\lambda^6$-[1,2,7]thiadiazepin-1-yl)-ethylamine

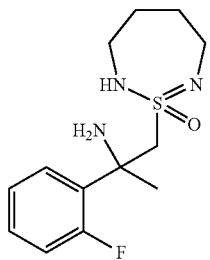 [SMILES: CC(N)(CS1(=O)=NCCCCN1)c1ccccc1F]

A mixture of (RS)-[1-(2-fluoro-phenyl)-1-methyl-2-(1-oxo-3,6-dihydro-2H-1$\lambda^6$-[1,2,7]thiadiazepin-1-yl)-ethyl]-carbamic acid benzyl ester (1.98 g, 4.74 mmol, Eq: 1.00) and palladium on carbon (10% Pd/C) (1.48 g, 1.39 mmol, Eq: 0.294) in ethyl acetate (50 ml) was hydrogenated (balloon pressure) at 23° C. for 1.5 h, added more palladium on carbon (10% Pd/C) (1.30 g, 1.22 mmol, Eq: 0.258) and continued hydrogenation at 23° C. for 2 h. Filtered catalyst off, washed with ethyl acetate and the filtrate containing the crude 1-(2-fluoro-phenyl)-1-methyl-2-(1-oxo-3,4,5,6-tetrahydro-2H-1$\lambda^6$-[1,2,7]thiadiazepin-1-yl)-ethylamine was used directly in the next step without further purification. MS (ISP): m/z=286.2 [M+H]$^+$.

A15b: (R)-1-(2-Fluoro-phenyl)-1-methyl-2-(1-oxo-3,4,5,6-tetrahydro-2H-1$\lambda^6$-[1,2,7]thiadiazepin-1-yl)-ethylamine

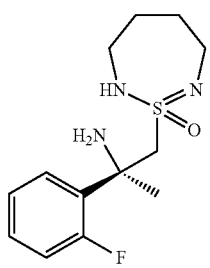 [SMILES: C[C@](N)(CS1(=O)=NCCCCN1)c1ccccc1F]

A mixture of [(R)-1-(2-fluoro-phenyl)-1-methyl-2-(1-oxo-3,6-dihydro-2H-1$\lambda^6$-[1,2,7]thiadiazepin-1-yl)-ethyl]-carbamic acid benzyl ester (2.89 g, 6.92 mmol, Eq: 1.00) and palladium on carbon (10% Pd/C) (1.77 g, 1.66 mmol, Eq: 0.24) in ethyl acetate (93.4 ml) was hydrogenated (balloon pressure) at 23° C. for 16 h. Filtered catalyst off, washed with ethyl acetate and the solution of the crude (R)-1-(2-fluoro-phenyl)-1-methyl-2-(1-oxo-3,4,5,6-tetrahydro-2H-1$\lambda^6$-[1,2,7]thiadiazepin-1-yl)-ethylamine was used directly in the next step without further purification. MS (ISP): m/z=286.1 [M+H]$^+$.

A15c: (6S)-1-((R)-2-amino-2-(2-fluorophenyl)propyl)-6-(trifluoromethyl)-3,4,5,6-tetrahydro-2H-1,2,7-thiadiazepine 1-oxide

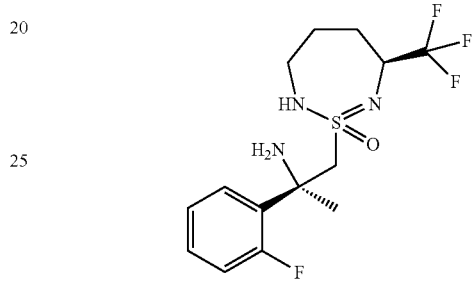

A mixture of benzyl ((2R)-2-(2-fluorophenyl)-1-((6S)-1-oxido-6-(trifluoromethyl)-3,6-dihydro-2H-1,2,7-thiadiazepin-1-yl)propan-2-yl)carbamate (4 g, 8.24 mmol, Eq: 1) and palladium on carbon (10% Pd/C) (4.38 g, 4.12 mmol, Eq: 0.5) in ethyl acetate (800 ml) was hydrogenated (balloon pressure) at 23° C. for 5 days. Filtered catalyst off, washed with ethyl acetate, evaporated all volatiles to give the crude (6S)-1-((R)-2-amino-2-(2-fluorophenyl)propyl)-6-(trifluoromethyl)-3,4,5,6-tetrahydro-2H-1,2,7-thiadiazepine 1-oxide (2.69 g, 7.61 mmol, 92.4% yield) as a colorless oil which was used directly in the next step without further purification. MS (ISP): m/z=354.2 [M+H]$^+$.

A15d: 1-0R)-2-Amino-2-(2-fluorophenyl)propyl)-4,4-difluoro-2,3,4,5-tetrahydro-1,2,6-thiadiazine 1-oxide

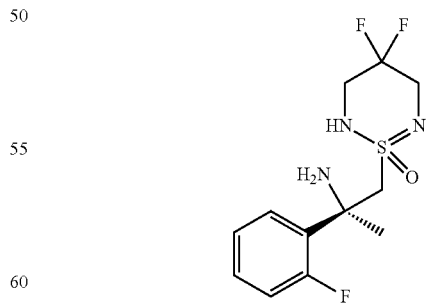

A mixture of benzyl ((2R)-1-(4,4-difluoro-1-oxido-2,3,4,5-tetrahydro-1,2,6-thiadiazin-1-yl)-2-(2-fluorophenyl)propan-2-yl)carbamate (330 mg, 748 µmol, Eq: 1) and palladium on carbon (10% Pd/C) (795 mg, 748 µmol, Eq: 1) in ethyl acetate (60 ml) was hydrogenated (1.5 bar pressure) at 23° C. for 16 h. Filtered catalyst off, washed with ethyl acetate, evaporated all volatiles to give the crude 1-((R)-2-amino-2-(2-fluorophenyl)propyl)-4,4-difluoro-2,3,4,5-tetrahydro-1,2,6-thiadiazine 1-oxide (mixture of isomers) (260 mg, 846 µmol, 113% yield) as a colorless oil which was used directly in the next step without further purification. MS (ISP): m/z=308.1 [M+H]$^+$.

Synthesis of Intermediates A16

A16a: (RS)-1-Benzoyl-3-[1-(2-fluoro-phenyl)-1-methyl-2-(1-oxo-3,4,5,6-tetrahydro-2H-1$\lambda^6$-[1,2,7]thiadiazepin-1-yl)-ethyl]-thiourea

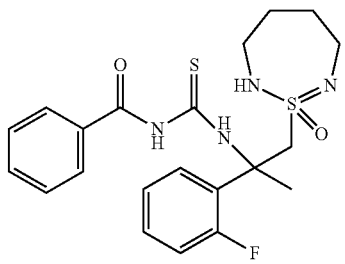 [SMILES: CC(CS1(=O)=NCCCCN1)(NC(=S)NC(=O)c1ccccc1)c1ccccc1F]

To a solution of crude 1-(2-fluoro-phenyl)-1-methyl-2-(1-oxo-3,4,5,6-tetrahydro-2H-1$\lambda^6$-[1,2,7]thiadiazepin-1-yl)-ethylamine in ethyl acetate (ca. 100 ml) was added benzoyl isothiocyanate (813 mg, 669 µl, 4.98 mmol, Eq: 1.05) and the mixture was stirred at 23° C. for 25 min. Evaporated all volatiles and the crude (RS)-1-benzoyl-3-[1-(2-fluoro-phenyl)-1-methyl-2-(1-oxo-3,4,5,6-tetrahydro-2H-1$\lambda^6$-[1,2,7]thiadiazepin-1-yl)-ethyl]-thiourea was obtained as a yellow foam which was used without further purification. MS (ISP): m/z=449.2 [M+H]$^+$.

A16b: 1-Benzoyl-3-[(R)-1-(2-fluoro-phenyl)-1-methyl-2-(1-oxo-3,4,5,6-tetrahydro-2H-1λ-[1,2,7]thiadiazepin-1-yl)-ethyl]-thiourea

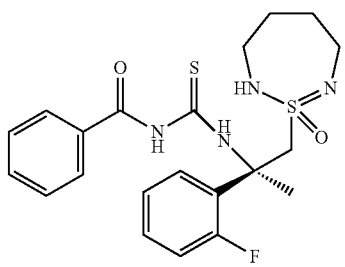 [SMILES: C[C@@](CS1(=O)=NCCCCN1)(NC(=S)NC(=O)c1ccccc1)c1ccccc1F]

To a solution of crude (R)-1-(2-fluoro-phenyl)-1-methyl-2-(1-oxo-3,4,5,6-tetrahydro-2H-1$\lambda^6$-[1,2,7]thiadiazepin-1-yl)-ethylamine in ethyl acetate (ca. 250 ml) was added benzoyl isothiocyanate (1.19 g, 977 µl, 7.27 mmol, Eq: 1.05) and the mixture stirred at 23° C. for 25 min. Evaporated all volatiles and the crude 1-benzoyl-3-[(R)-1-(2-fluoro-phenyl)-1-methyl-2-(1-oxo-3,4,5,6-tetrahydro-2H-1λ-[1,2,7]thiadiazepin-1-yl)-ethyl]-thiourea was obtained as a yellow foam which was used without further purification. MS (ISP): m/z=449.2 [M+H]$^+$.

A16c: 1-Benzoyl-3-[(R)-1-(2-fluoro-phenyl)-1-methyl-2-((S)-1-oxo-6-trifluoromethyl-3,4,5,6-tetrahydro-2H-1$\lambda^6$-[1,2,7]thiadiazepin-1-yl)-ethyl]-thiourea

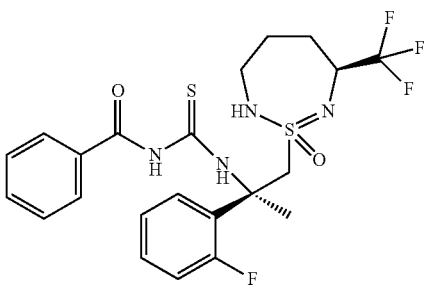 [SMILES: C[C@@](CS1(=O)=N[C@H](C(F)(F)F)CCCN1)(NC(=S)NC(=O)c1ccccc1)c1ccccc1F]

To a solution of crude (6S)-1-((R)-2-amino-2-(2-fluorophenyl)propyl)-6-(trifluoromethyl)-3,4,5,6-tetrahydro-2H-1,2,7-thiadiazepine 1-oxide (2.69 g, 7.61 mmol, Eq: 1) in ethyl acetate (300 ml) at 0° C. was added benzoyl isothiocyanate (1.3 g, 1.07 ml, 7.99 mmol, Eq: 1.05) and the mixture stirred at 0° C. for 3 h. Evaporated all volatiles and the crude 1-benzoyl-3-[(R)-1-(2-fluoro-phenyl)-1-methyl-2-((S)-1-oxo-6-trifluoromethyl-3,4,5,6-tetrahydro-2H-1$\lambda^6$-[1,2,7]thiadiazepin-1-yl)-ethyl]-thiourea was obtained as a yellow foam which was used without further purification. MS (ISP): m/z=517.2 [M+1-1]$^+$.

A16d: 1-Benzoyl-3-[(R)-2-(4,4-difluoro-1-oxo-2,3,4,5-tetrahydro-1$\lambda^6$-[1,2,6]thiadiazin-1-yl)-1-(2-fluoro-phenyl)-1-methyl-ethyl]-thiourea

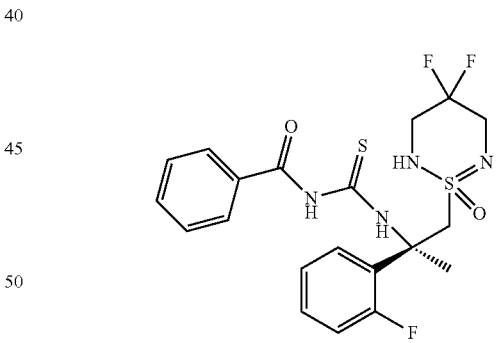

To a solution of crude 1-((R)-2-amino-2-(2-fluorophenyl)propyl)-4,4-difluoro-2,3,4,5-tetrahydro-1,2,6-thiadiazine 1-oxide (260 mg, 846 µmol, Eq: 1) in ethyl acetate (25 ml) at 0° C. was added benzoyl isothiocyanate (145 mg, 119 µl, 888 µmol, Eq: 1.05) and the mixture stirred at 0° C. for 1.5 h. Evaporated all volatiles and the crude 1-benzoyl-3-[(R)-2-(4,4-difluoro-1-oxo-2,3,4,5-tetrahydro-1$\lambda^6$-[1,2,6]thiadiazin-1-yl)-1-(2-fluoro-phenyl)-1-methyl-ethyl]-thiourea (mixture of isomers) was obtained as a yellow foam which was used without further purification. MS (ISP): m/z=471.2 [M+H]$^+$.

Synthesis of Intermediates A17

A17a1: N-[(3RS,4aRS)-3-(2-fluoro-phenyl)-3-methyl-4a-oxo-3,4,6,7,8,9-hexahydro-4aλ⁶-thia-2,5,9a-triaza-benzocyclohepten-1-yl]-benzamide and
A17a2: N-[(3RS,4aSR)-3-(2-fluoro-phenyl)-3-methyl-4a-oxo-3,4,6,7,8,9-hexahydro-4aλ⁶-thia-2,5,9a-triaza-benzocyclohepten-1-yl]-benzamide

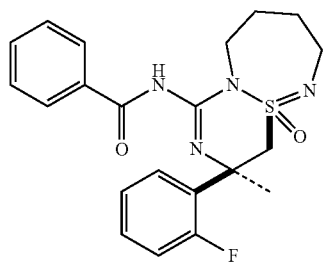

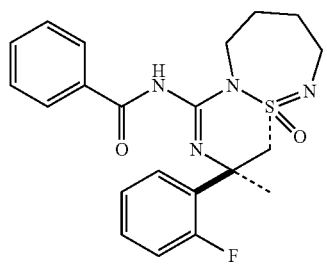

To a solution of crude (RS)-1-benzoyl-3-[1-(2-fluoro-phenyl)-1-methyl-2-(1-oxo-3,4,5,6-tetrahydro-2H-1λ⁶-[1,2,7]thiadiazepin-1-yl)-ethyl]-thiourea in acetonitrile (70 ml) at 23° C. was added N-(3-dimethylaminopropyl)-N'-ethylcarbodiimide hydrochloride (EDC HCl) (1.36 g, 7.11 mmol, Eq: 1.5) and the mixture was stirred at 80° C. for 70 min. Concentrated in vacuum and the crude material was purified by flash chromatography (silica gel, 70 g, 0% to 60% EtOAc in heptane) to give the N-[(3RS,4aRS)-3-(2-fluoro-phenyl)-3-methyl-4a-oxo-3,4,6,7,8,9-hexahydro-4aλ⁶-thia-2,5,9a-triaza-benzocyclohepten-1-yl]-benzamide (634 mg, 1.53 mmol, 32.3% yield) as a white foam (faster eluting diastereomer) and the N-[(3RS,4aSR)-3-(2-fluoro-phenyl)-3-methyl-4a-oxo-3,4,6,7,8,9-hexahydro-4aλ⁶-thia-2,5,9a-triaza-benzocyclohepten-1-yl]-benzamide (857 mg, 2.07 mmol, 43.6% yield) as a white foam (slower eluting diastereomer). MS (ISP) for A17a1: m/z=415.3; [M+H]⁺. MS (ISP) for A17a2: m/z=415.3 [M+H]+.

A17b1: N-[(3R,4aR)-3-(2-fluoro-phenyl)-3-methyl-4a-oxo-3,4,6,7,8,9-hexahydro-4aλ⁶-thia-2,5,9a-triaza-benzocyclohepten-1-yl]-benzamide and A17b2: N-[(3R,4aS)-3-(2-fluoro-phenyl)-3-methyl-4a-oxo-3,4,6,7,8,9-hexahydro-4aλ⁶-thia-2,5,9a-triaza-benzocyclohepten-1-yl]-benzamide

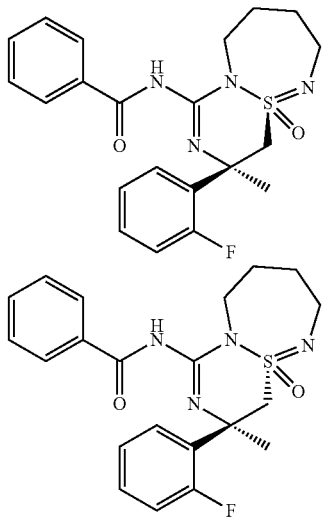

To a solution of crude 1-benzoyl-3-[(R)-1-(2-fluoro-phenyl)-1-methyl-2-(1-oxo-3,4,5,6-tetrahydro-2H-1λ-[1,2,7]thiadiazepin-1-yl)-ethyl]-thiourea in acetonitrile (131 ml) at 23° C. was added N-(3-dimethylaminopropyl)-N'-ethylcarbodiimide hydrochloride (EDC HCl) (1.99 g, 10.4 mmol, Eq: 1.5) and stirred at 80° C. for 80 min. Concentrated in vacuum and the crude material was purified thrice by flash chromatography (silica gel, 70 g, 0% to 50% EtOAc in heptane) to give the N-[(3R,4aR)-3-(2-fluoro-phenyl)-3-methyl-4a-oxo-3,4,6,7,8,9-hexahydro-4aλ⁶-thia-2,5,9a-triaza-benzocyclohepten-1-yl]-benzamide (0.948 g, 2.29 mmol, 33.0% yield) as a light yellow foam (faster eluting diastereomer) and the N-[(3R,4aS)-3-(2-fluoro-phenyl)-3-methyl-4a-oxo-3,4,6,7,8,9-hexahydro-4aλ⁶-thia-2,5,9a-triaza-benzocyclohepten-1-yl]-benz amide (1.178 g, 2.84 mmol, 41.1% yield) as a white solid (slower eluting diastereomer). MS (ISP) for A17b1: m/z=415.2 [M+H]⁺. MS (ISP) for A17b2: m/z=415.2 [M+H]⁺.

A17c: N-((2S,9R)-9-(2-fluorophenyl)-9-methyl-11-oxido-2-(trifluoromethyl)-2,3,4,5,9,10-hexahydro-[1,2,4]thiadiazino[1,2-a][1,2,7]thiadiazepin-7-yl)benzamide

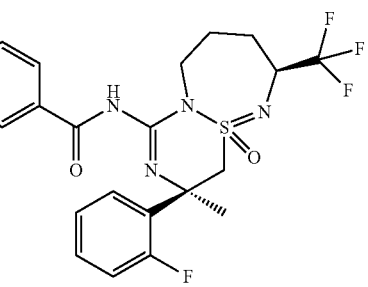

To a solution of crude 1-benzoyl-3-[(R)-1-(2-fluoro-phenyl)-1-methyl-2-((S)-1-oxo-6-trifluoromethyl-3,4,5,6-tetrahydro-2H-1λ⁶-[1,2,7]thiadiazepin-1-yl)-ethyl]-thiourea in acetonitrile (300 ml) at 23° C. was added N-(3-dimethylaminopropyl)-N'-ethylcarbodiimide hydrochloride (EDC HCl) (2.19 g, 11.4 mmol, Eq: 1.5) and stirred at 65° C. for 2 h. Poured onto sat. NaHCO₃-sol., extracted with ethyl acetate, dried the organic layer over Na₂SO₄. Filtration and removal of the solvent in vacuum left the crude material (4.18 g) as a light yellow solid which was purified twice by flash chromatography (silica gel, 100 g, 0% to 30% EtOAc in heptane) to give the N-((2S,9R)-9-(2-fluorophenyl)-9-methyl-11-oxido-2-(trifluoromethyl)-2,3,4,5,9,10-hexahydro-[1,2,4]thiadiazino[1,2-a][1,2,7]thiadiazepin-7-yl)benzamide (1.73 g, 3.59 mmol, 47.1% yield) as a white solid (mixture of isomers). MS (ISP): m/z=482.1 [M+H].

A17d: N-((8R)-3,3-Difluoro-8-(2-fluorophenyl)-8-methyl-10-oxido-3,4,8,9-tetrahydro-2H-[1,2,6]thiadiazino[1,2-a][1,2,4]thiadiazin-6-yl)benzamide

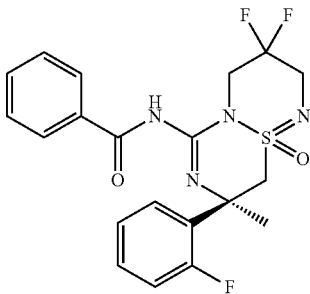 [SMILES: C[C@@]1(c2ccccc2F)CS2(=O)=NCC(F)(F)CN2C(NC(=O)c2ccccc2)=N1]

To a solution of crude 1-benzoyl-3-[(R)-2-(4,4-difluoro-1-oxo-2,3,4,5-tetrahydro-1λ⁶-[1,2,6]thiadiazin-1-yl)-1-(2-fluoro-phenyl)-1-methyl-ethyl]-thiourea in acetonitrile (25 ml) at 23° C. was added N-(3-dimethylaminopropyl)-N'-ethylcarbodiimide hydrochloride (EDC HCl) (243 mg, 1.27 mmol, Eq: 1.5) and stirred at 65° C. for 1.5 h. Poured onto sat. NaHCO₃-sol., extracted with ethyl acetate, dried the organic layer over Na₂SO₄. Filtration and removal of the solvent in vacuum left the crude material which was purified twice by flash chromatography (silica gel, 20 g, 0% to 50% EtOAc in heptane) to give the N-((8R)-3,3-difluoro-8-(2-fluorophenyl)-8-methyl-10-oxido-3,4,8,9-tetrahydro-2H-[1,2,6]thiadiazino[1,2-a][1,2,4]thiadiazin-6-yl)benzamide (mixture of isomers) (200 mg, 458 μmol, 54.2% yield) as a yellow foam. MS (ISP): m/z=437.2 [M+H].

Synthesis of Intermediates A19

A19a1: [(3RS,4aRS)-3-(2-Fluoro-phenyl)-3-methyl-4a-oxo-3,4,6,7,8,9-hexahydro-4aλ⁶-thia-2,5,9a-triaza-benzocyclohepten-1-yl]-carbamic acid tert-butyl ester and A19a2: [(3RS,4aSR)-3-(2-fluoro-phenyl)-3-methyl-4a-oxo-3,4,6,7,8,9-hexahydro-4aλ⁶-thia-2,5,9a-triaza-benzocyclohepten-1-yl]-carbamic acid tert-butyl ester

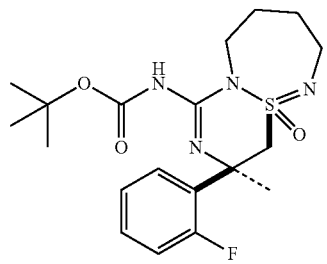

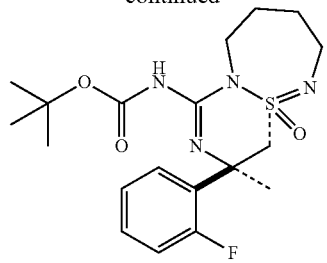

To a dry mixture of (RS)-N-[3-(2-fluoro-phenyl)-3-methyl-4a-oxo-3,4,6,7,8,9-hexahydro-4aλ⁶-thia-2,5,9a-triaza-benzocyclohepten-1-yl]-benzamide (204 mg, 492 μmol, Eq: 1.00), di-tert-butyl dicarbonate (118 mg, 126 μl, 541 μmol, Eq: 1.10) and DMAP (12.0 mg, 98.4 μmol, Eq: 0.20) was added at 23° C. tetrahydrofuran (5 ml) followed by triethylamine (54.8 mg, 75.5 μl, 541 μmol, Eq: 1.10). The mixture was stirred at 23° C. for 2 h, incomplete conversion, added di-tert-butyl dicarbonate (118 mg, 126 μl, 541 μmol, Eq: 1.10), triethylamine (54.8 mg, 75.5 μl, 541 μmol, Eq: 1.10) and DMAP (12.0 mg, 98.4 μmol, Eq: 0.20), continued stirring at 23° C. for 18 h, all volatiles were evaporated and the crude material was allowed to stand at 23° C. for 6 h to give the intermediates A18a1 and A18a2. Dissolved in methanol (5 ml), added ammonia (7 M in MeOH) (1.76 ml, 12.3 mmol, Eq: 25) and stirred at 23° C. for 40 min. All volatiles were removed in vacuum and the crude material was purified by flash chromatography (silica gel, 20 g, 0% to 50% EtOAc in heptane) to give the [(3RS,4aRS)-3-(2-fluoro-phenyl)-3-methyl-4a-oxo-3,4,6,7,8,9-hexahydro-4aλ⁶-thia-2,5,9a-triaza-benzocyclohepten-1-yl]-carbamic acid tert-butyl ester (75 mg, 183 μmol, 37.1% yield) as a light yellow gum which crystallized later to an off-white solid (faster eluting diastereomer) and the [(3RS,4aSR)-3-(2-fluoro-phenyl)-3-methyl-4a-oxo-3,4,6,7,8,9-hexahydro-4aλ⁶-thia-2,5,9a-triaza-benzocyclohepten-1-yl]-carbamic acid tert-butyl ester (71 mg, 173 μmol, 35.1% yield) as a light yellow gum (slower eluting diastereomer). MS (ISP) for A19a1: m/z=411.3 [M+H]⁺. MS (ISP) for A19a2: m/z=411.3 [M+H]⁺.

A19b1: [(3R,4aR)-3-(2-Fluoro-phenyl)-3-methyl-4a-oxo-3,4,6,7,8,9-hexahydro-4aλ⁶-thia-2,5,9a-triaza-benzocyclohepten-1-yl]-carbamic acid tert-butyl ester

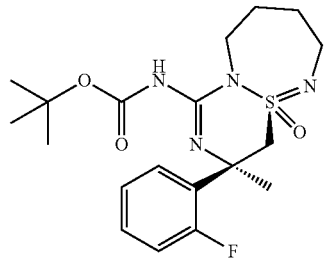 [SMILES: CC(C)(C)OC(=O)NC1=N[C@](C)(c2ccccc2F)C[S@]2(=O)=NCCCCN12]

To a solution of N-[(3R,4aR)-3-(2-fluoro-phenyl)-3-methyl-4a-oxo-3,4,6,7,8,9-hexahydro-4aλ⁶-thia-2,5,9a-triaza-benzocyclohepten-1-yl]-benzamide (948 mg, 2.29 mmol, Eq: 1.00), triethylamine (255 mg, 351 μl, 2.52 mmol, Eq: 1.10) and DMAP (55.9 mg, 457 μmol, Eq: 0.20) in tetrahydrofuran (9.1 ml) at 23° C. was added di-tert-butyl dicarbonate (Boc₂O) (549 mg, 584 μl, 2.52 mmol, Eq: 1.10) and the mixture was stirred at 23° C. for 1 h, added again triethylamine (255 mg, 351 μl, 2.52 mmol, Eq: 1.10) and di-tert-butyl dicarbonate (549 mg, 584 μl, 2.52 mmol, Eq: 1.10) and continued stirring at 23° C. for 20 h. Evaporated all volatiles and to give a yellow oil which was quickly purified by flash chromatography (silica gel, 50 g, 0% to 50% EtOAc in heptane) to give the intermediate A18b1 as a yellow foam (~1.5 g). Dissolved in methanol (10 ml), added ammonia (7 M in MeOH) (8.17 ml, 57.2 mmol, Eq: 25) and continued stirring at 23° C. for 75 min. Evaporated all volatiles to give a yellow oil which was purified by flash chromatography (silica gel, 70 g, 0% to 50% EtOAc in heptane) to give the [(3R,4aR)-3-(2-fluoro-phenyl)-3-methyl-4a-oxo-3,4,6,7,8,9-hexahydro-4aλ⁶-thia-2,5,9a-triaza-benzocyclohepten-1-yl]-carbamic acid tert-butyl ester (766 mg, 1.87 mmol, 81.6% yield) as an off-white solid. MS (ISP): m/z=411.3 [M+H]⁺.

A19b2: [(3R,4aS)-3-(2-fluoro-phenyl)-3-methyl-4a-oxo-3,4,6,7,8,9-hexahydro-4aλ⁶-thia-2,5,9a-triaza-benzocyclohepten-1-yl]-carbamic acid tert-butyl ester

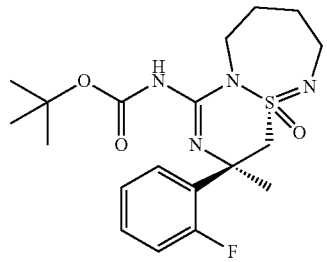 [SMILES: CC(C)(C)OC(=O)NC1=N[C@](C)(c2ccccc2F)C[S@@]2(=O)=NCCCCN12]

To a solution of N-[(3R,4aS)-3-(2-fluoro-phenyl)-3-methyl-4a-oxo-3,4,6,7,8,9-hexahydro-4aλ⁶-thia-2,5,9a-triaza-benzocyclohepten-1-yl]-benzamide (684 mg, 1.65 mmol, Eq: 1.00), triethylamine (367 mg, 506 μl, 3.63 mmol, Eq: 2.20) and DMAP (40.3 mg, 330 μmol, Eq: 0.20) in tetrahydrofuran (10 ml) at 23° C. was added di-tert-butyl dicarbonate (Boc₂O) (792 mg, 843 μl, 3.63 mmol, Eq: 2.20) and the mixture was stirred at 23° C. for 18 h. Evaporated all volatiles to give the intermediate A18b2, added methanol (5 ml) and ammonia (7 M in MeOH) (5.89 ml, 41.3 mmol, Eq: 25) and continued stirring at 23° C. for 35 min. Evaporated all volatiles to give a yellow oil which was purified by flash chromatography (silica gel, 50 g, 0% to 60% EtOAc in heptane) to give the [(3R,4aS)-3-(2-fluoro-phenyl)-3-methyl-4a-oxo-3,4,6,7,8,9-hexahydro-4aλ⁶-thia-2,5,9a-triaza-benzocyclohepten-1-yl]-carbamic acid tert-butyl ester (418 mg, 1.02 mmol, 61.7% yield) as a light yellow foam. MS (ISP): m/z=411.2 [M+H]⁺.

A19c: tert-Butyl ((2S,9R)-9-(2-fluorophenyl)-9-methyl-11-oxido-2-(trifluoromethyl)-2,3,4,5,9,10-hexahydro-[1,2,4]thiadiazino[1,2-a][1,2,7]thiadiazepin-7-yl)carbamate

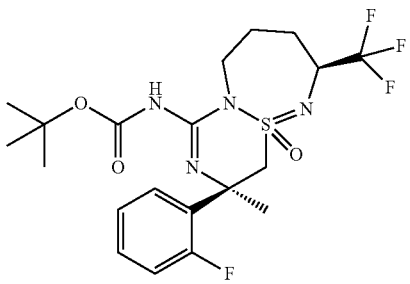 [SMILES: CC(C)(C)OC(=O)NC1=N[C@](C)(c2ccccc2F)CS2(=O)=N[C@H](C(F)(F)F)CCCN12]

To a solution of N-((2S,9R)-9-(2-fluorophenyl)-9-methyl-11-oxido-2-(trifluoromethyl)-2,3,4,5,9,10-hexahydro-[1,2,4]thiadiazino[1,2-a][1,2,7]thiadiazepin-7-yl)benzamide (500 mg, 1.04 mmol, Eq: 1), triethylamine (115 mg, 159 μl, 1.14 mmol, Eq: 1.1) and DMAP (127 mg, 1.04 mmol, Eq: 1) in tetrahydrofuran (7 ml) at 23° C. was added di-tert-butyl dicarbonate (Boc₂O) (452 mg, 481 μl, 2.07 mmol, Eq: 2) and the mixture was stirred at 23° C. for 18 h. Poured onto sat. NaHCO₃-sol., extracted with ethyl acetate, dried the organic layer over Na₂SO₄. Filtration and removal of the solvent in vacuum left the crude material which was purified by flash chromatography (silica gel, 20 g, 0% to 50% EtOAc in heptane) to give the tert-butyl benzoyl((2S,9R)-9-(2-fluorophenyl)-9-methyl-11-oxido-2-(trifluoromethyl)-2,3,4,5,9,10-hexahydro-[1,2,4]thiadiazino[1,2-a][1,2,7]thiadiazepin-7-yl)carbamate (mixture of isomers) (510 mg, 875 μmol, 84.5% yield) as a white solid. This material was dissolved in methanol (25 ml) and ammonia (7 M in MeOH) (3.13 ml, 21.9 mmol, Eq: 25) was added and stirring was continued at 23° C. for 30 min. Evaporated all volatiles to give the crude tert-butyl ((2S,9R)-9-(2-fluorophenyl)-9-methyl-11-oxido-2-(trifluoromethyl)-2,3,4,5,9,10-hexahydro-[1,2,4]thiadiazino[1,2-a][1,2,7]thiadiazepin-7-yl)carbamate (mixture of isomers) as a yellow oil which was used in the next step without further purification. MS (ISP): m/z=479.2 [M+H]⁺.

A19d: tert-Butyl ((8R)-3,3-difluoro-8-(2-fluorophenyl)-8-methyl-10-oxido-3,4,8,9-tetrahydro-2H-[1,2,6]thiadiazino[1,2-a][1,2,4]thiadiazin-6-yl)carbamate

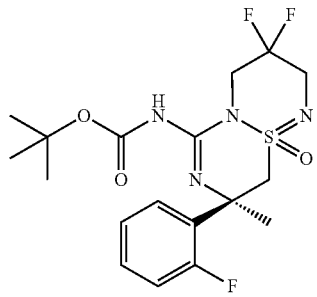 [SMILES: CC(C)(C)OC(=O)NC1=N[C@](C)(c2ccccc2F)CS2(=O)=NCC(F)(F)CN12]

To a solution of N-((8R)-3,3-difluoro-8-(2-fluorophenyl)-8-methyl-10-oxido-3,4,8,9-tetrahydro-2H-[1,2,6]thiadiazino[1,2-a][1,2,4]thiadiazin-6-yl)benzamide (200 mg, 458

µmol, Eq: 1), triethylamine (51 mg, 70.3 µl, 504 µmol, Eq: 1.1) and DMAP (56 mg, 458 µmol, Eq: 1) in tetrahydrofuran (3 ml) at 23° C. was added di-tert-butyl dicarbonate (Boc₂O) (200 mg, 213 µl, 916 µmol, Eq: 2) and the mixture was stirred at 23° C. for 18 h. Poured onto sat. NaHCO₃-sol., extracted with ethyl acetate, dried the organic layer over Na₂SO₄. Filtration and removal of the solvent in vacuum left the crude material which was purified by flash chromatography (silica gel, 20 g, 0% to 50% EtOAc in heptane) to give the tert-butyl benzoyl((8R)-3,3-difluoro-8-(2-fluorophenyl)-8-methyl-10-oxido-3,4,8,9-tetrahydro-2H-[1,2,6]thiadiazino [1,2-a][1,2,4]thiadiazin-6-yl)carbamate (mixture of isomers) (200 mg, 371 µmol, 81% yield) as a white solid. This material was dissolved in methanol (10 ml) and ammonia (7 M in MeOH) (1.33 ml, 9.32 mmol, Eq: 25) was added and stirring was continued at 23° C. for 30 min. Evaporated all volatiles to give the crude tert-butyl ((8R)-3,3-difluoro-8-(2-fluorophenyl)-8-methyl-10-oxido-3,4,8,9-tetrahydro-2H-[1,2,6]thiadiazino[1,2-a][1,2,4]thiadiazin-6-yl)carbamate (mixture of isomers) as a yellow oil which was used in the next step without further purification. MS (ISP): m/z=433.2 [M+H]⁺.

Synthesis of Intermediates A20

A20a1: (3RS,4aRS)-3-(2-Fluoro-phenyl)-3-methyl-4a-oxo-3,4,6,7,8,9-hexahydro-4aλ⁶-thia-2,5,9a-tri-aza-benzocyclohepten-1-ylamine

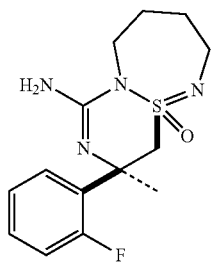

To a solution of [(3RS,4aRS)-3-(2-fluoro-phenyl)-3-methyl-4a-oxo-3,4,6,7,8,9-hexahydro-4aλ⁶-thia-2,5,9a-triaza-benzocyclohepten-1-yl]-carbamic acid tert-butyl ester (75 mg, 183 µmol, Eq: 1.00) in dichloromethane (dry) (3 ml) at 23° C. was added TFA (1.49 g, 1.00 ml, 13.0 mmol, Eq: 71.3) and the mixture was stirred at 23° C. for 1 h. Evaporated all volatiles, added DCM and 25% NH₄OH-sol., separated phases, the organic layer was dried over Na₂SO₄. Removal of the solvent in vacuum left the pure (3RS,4aRS)-3-(2-fluoro-phenyl)-3-methyl-4a-oxo-3,4,6,7,8,9-hexahydro-4aλ⁶-thia-2,5,9a-triaza-benzocyclohepten-1-ylamine (50 mg, 161 µmol, 88.2% yield) as a light yellow foam. MS (ISP): m/z=311.2 [M+H]⁺.

A20a2: (3RS,4aSR)-3-(2-Fluoro-phenyl)-3-methyl-4a-oxo-3,4,6,7,8,9-hexahydro-4aλ⁶-thia-2,5,9a-tri-aza-benzocyclohepten-1-ylamine

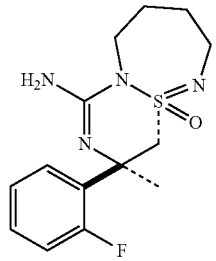

To a solution of [(3RS,4aSR)-3-(2-fluoro-phenyl)-3-methyl-4a-oxo-3,4,6,7,8,9-hexahydro-4aλ⁶-thia-2,5,9a-triaza-benzocyclohepten-1-yl]-carbamic acid tert-butyl ester (71 mg, 173 µmol, Eq: 1.00) in dichloromethane (dry) (3 ml) at 23° C. was added TFA (1.48 g, 1.00 ml, 13.0 mmol, Eq: 75.1) and the mixture was stirred at 23° C. for 1 h. Evaporated all volatiles, added DCM and 25% NH₄OH-sol., separated phases, the organic layer was dried over Na₂SO₄. Removal of the solvent in vacuum left the pure (3RS,4aSR)-3-(2-fluoro-phenyl)-3-methyl-4a-oxo-3,4,6,7,8,9-hexahydro-4aλ⁶-thia-2,5,9a-triaza-benzocyclohepten-1-ylamine (48 mg, 155 µmol, 89.4% yield) as an off-white solid. MS (ISP): m/z=311.2 [M+H]⁺.

A20b1: (3R,4aR)-3-(2-Fluoro-phenyl)-3-methyl-4a-oxo-3,4,6,7,8,9-hexahydro-4aλ⁶-thia-2,5,9a-triaza-benzocyclohepten-1-ylamine

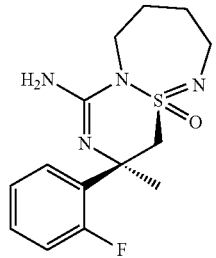 [SMILES: C[C@@]1(c2ccccc2F)C[S@]2(=O)=NCCCCN2C(N)=N1]

To a solution of [(3R,4aR)-3-(2-fluoro-phenyl)-3-methyl-4a-oxo-3,4,6,7,8,9-hexahydro-4aλ⁶-thia-2,5,9a-triaza-benzocyclohepten-1-yl]-carbamic acid tert-butyl ester (760 mg, 1.85 mmol, Eq: 1.00) in dichloromethane (dry) (5.2 ml) at 23° C. was added trifluoroacetic acid (TFA) (3.8 g, 2.57 ml, 33.3 mmol, Eq: 18) and the mixture was stirred at 23° C. for 1.25 h. Evaporated all volatiles, partitioned between ethyl acetate and sat. NaHCO₃-sol. plus brine, the organic layer was dried over Na₂SO₄. Filtration and removal of the solvent in vacuum left a colorless oil which was purified by flash chromatography (silica gel, 50 g, 0% to 100% EtOAc in heptane) to give the (3R,4aR)-3-(2-fluoro-phenyl)-3-methyl-4a-oxo-3,4,6,7,8,9-hexahydro-4aλ⁶-thia-2,5,9a-triaza-benzocyclohepten-1-ylamine (535 mg, 1.72 mmol, 93.1% yield) as a white foam. MS (ISP): m/z=311.1 [M+H]⁺.

A20b2: (3R,4aS)-3-(2-Fluoro-phenyl)-3-methyl-4a-oxo-3,4,6,7,8,9-hexahydro-4aλ⁶-thia-2,5,9a-triaza-benzocyclohepten-1-ylamine

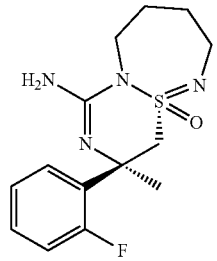 [SMILES: C[C@@]1(c2ccccc2F)C[S@@]2(=O)=NCCCCN2C(N)=N1]

To a solution of [(3R,4aS)-3-(2-fluoro-phenyl)-3-methyl-4a-oxo-3,4,6,7,8,9-hexahydro-4aλ⁶-thia-2,5,9a-triaza-benzocyclohepten-1-yl]-carbamic acid tert-butyl ester (415 mg, 1.01 mmol, Eq: 1.00) in dichloromethane (dry) (6 ml) at 23° C. was added trifluoroacetic acid (TFA) (2.96 g, 2.00 ml, 25.9 mmol, Eq: 25.65) and the mixture was stirred at 23° C. for 2 h. Evaporated all volatiles, partitioned between ethyl acetate and sat. NaHCO₃-sol. plus brine, the organic layer was dried over Na₂SO₄. Filtration and removal of the solvent in vacuum left the (3R,4aS)-3-(2-fluoro-phenyl)-3-methyl-4a-oxo-3,4,6,7,8,9-hexahydro-4aλ⁶-thia-2,5,9a-triaza-benzocyclohepten-1-ylamine (379 mg, 1.01 mmol, 100% yield; 83% purity) as a light yellow solid which was used without further purification. MS (ISP): m/z=311.1 [M+H]⁺.

A20c: (3R,4aS)-3-(2-Fluoro-phenyl)-3-methyl-4a-oxo-3,4,6,7,8,9-hexahydro-4aλ⁶-thia-2,5,9a-triaza-benzocyclohepten-1-ylamine

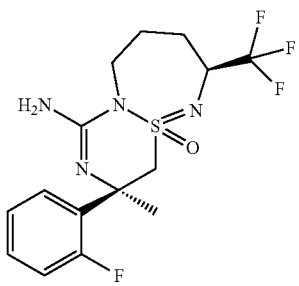 [SMILES: C[C@@]1(c2ccccc2F)CS2(=O)=N[C@H](C(F)(F)F)CCCN2C(N)=N1]

To a solution of crude tert-butyl ((2S,9R)-9-(2-fluorophenyl)-9-methyl-11-oxido-2-(trifluoromethyl)-2,3,4,5,9,10-hexahydro-[1,2,4]thiadiazino [1,2-a][1,2,7]thiadiazepin-7-yl)carbamate in dichloromethane (dry) (25 ml) at 23° C. was added trifluoroacetic acid (TFA) (2.5 g, 1.69 ml, 21.9 mmol, Eq: 25) and the mixture was stirred at 23° C. for 16 h. Poured cautiously onto sat. NaHCO₃-sol. plus brine, extracted with DCM, the organic layer was dried over Na₂SO₄. Filtration and removal of the solvent in vacuum left the crude material which was purified by chromatography (silica gel, 20 g, 0 to 100% EtOAc in heptane) to give the (2S,9R)-7-amino-9-(2-fluorophenyl)-9-methyl-2-(trifluoromethyl)-2,3,4,5,9,10-hexahydro-[1,2,4]thiadiazino[1,2-a][1,2,7]thiadiazepine 11-oxide (mixture of isomers) (273 mg, 721 µmol, 82.4% yield) as a white solid. MS (ISP): m/z=379.1 [M+H]⁺.

A20d: (8R)-6-Amino-3,3-difluoro-8-(2-fluorophenyl)-8-methyl-3,4,8,9-tetrahydro-2H-[1,2,6]thiadiazino[1,2-a][1,2,4]thiadiazine 10-oxide

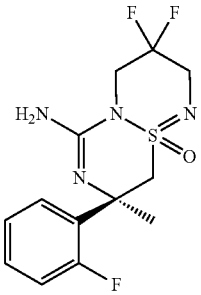 [SMILES: C[C@@]1(c2ccccc2F)CS2(=O)=NCC(F)(F)CN2C(N)=N1]

To a solution of crude tert-butyl ((8R)-3,3-difluoro-8-(2-fluorophenyl)-8-methyl-10-oxido-3,4,8,9-tetrahydro-2H-[1,2,6]thiadiazino [1,2-a][1,2,4]thiadiazin-6-yl)carbamate in dichloromethane (dry) (10 ml) at 23° C. was added trifluoroacetic acid (TFA) (1.06 g, 718 µl, 9.32 mmol, Eq: 25) and the mixture was stirred at 23° C. for 1 h. Poured cautiously onto sat. NaHCO₃-sol. plus brine, extracted with DCM, the organic layer was dried over Na₂SO₄. Filtration and removal of the solvent in vacuum left the crude material which was purified by chromatography (silica gel, 10 g, 0 to 100% EtOAc in heptane) to give the (8R)-6-amino-3,3-difluoro-8-(2-fluorophenyl)-8-methyl-3,4,8,9-tetrahydro-2H-[1,2,6]thiadiazino [1,2-a][1,2,4]thiadiazine 10-oxide (mixture of isomers) (58 mg, 175 µmol, 46.8% yield) as a light yellow foam. MS (ISP): m/z=333.2 [M+H]+.

Synthesis of Intermediates A21

A21a1: (3RS,4aRS)-3-(2-Fluoro-5-nitro-phenyl)-3-methyl-4a-oxo-3,4,6,7,8,9-hexahydro-4aλ⁶-thia-2,5,9a-triaza-benzocyclohepten-1-ylamine

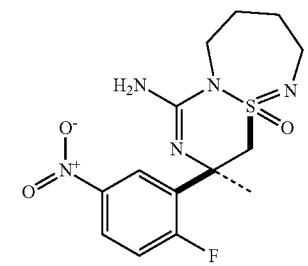

To a solution of (3RS,4aRS)-3-(2-fluoro-phenyl)-3-methyl-4a-oxo-3,4,6,7,8,9-hexahydro-4aλ⁶-thia-2,5,9a-triaza-benzocyclohepten-1-ylamine (39 mg, 126 µmol, Eq: 1.00) in conc. sulfuric acid (986 mg, 536 µl, 10.1 mmol, Eq: 80) at 0° C. was dropwise added fuming nitric acid (11.9 mg, 8.42 µl, 188 µmol, Eq: 1.50) and the mixture was stirred at 0° C. for 1.5 h. The reaction mixture was poured onto ice and basified with 3 M NaOH-sol. followed by extraction with dichloromethane. The organic layer was separated, dried over Na₂SO₄, filtered and evaporated to dryness to give the crude and pure (3RS,4aRS)-3-(2-fluoro-5-nitro-phenyl)-3-methyl-4a-oxo-3,4,6,7,8,9-hexahydro-4aλ⁶-thia-2,5,9a-triaza-benzocyclohepten-1-ylamine (34 mg, 95.7 µmol, 76.1% yield) as a light yellow oil. MS (ISP): m/z=356.2 [M+H]⁺.

A21a2: (3RS,4aSR)-3-(2-Fluoro-5-nitro-phenyl)-3-methyl-4a-oxo-3,4,6,7,8,9-hexahydro-4aλ⁶-thia-2,5,9a-triaza-benzocyclohepten-1-ylamine

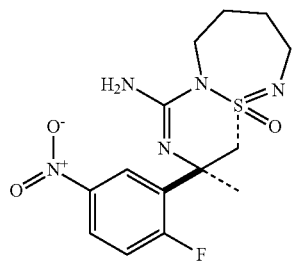

To a solution of (3RS,4aSR)-3-(2-fluoro-phenyl)-3-methyl-4a-oxo-3,4,6,7,8,9-hexahydro-4aλ⁶-thia-2,5,9a-triaza-benzocyclohepten-1-ylamine (34 mg, 110 µmol, Eq: 1.00) in conc. sulfuric acid (859 mg, 467 µl, 8.76 mmol, Eq: 80) at 0° C. was dropwise added fuming nitric acid (10.4 mg, 7.34 µl, 164 µmol, Eq: 1.50) and the mixture was stirred at 0° C. for 1.5 h. The reaction mixture was poured onto ice and basified with 3 M NaOH-sol. followed by extraction with dichloromethane. The organic layer was separated, dried over Na₂SO₄, filtered and evaporated to dryness to give the crude and pure (3RS,4aSR)-3-(2-fluoro-5-nitro-phenyl)-3-methyl-4a-oxo-3,4,6,7,8,9-hexahydro-4aλ⁶-thia-2,5,9a-triaza-benzocyclohepten-1-ylamine (28 mg, 78.8 µmol, 71.9% yield) as a white foam. MS (ISP): m/z=356.2 [M+H]+.

A21b1: (3R,4aR)-3-(2-Fluoro-5-nitro-phenyl)-3-methyl-4a-oxo-3,4,6,7,8,9-hexahydro-4aλ⁶-thia-2,5,9a-triaza-benzocyclohepten-1-ylamine

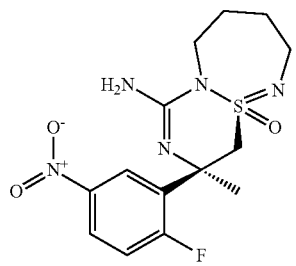 [SMILES: C[C@@]1(c2cc([N+](=O)[O-])ccc2F)C[S@]2(=O)=NCCCCN2C(N)=N1]

To a solution of (3R,4aR)-3-(2-fluoro-phenyl)-3-methyl-4a-oxo-3,4,6,7,8,9-hexahydro-4aλ⁶-thia-2,5,9a-triaza-benzocyclohepten-1-ylamine (203 mg, 654 µmol, Eq: 1.00) in conc. sulfuric acid (5.13 g, 2.79 ml, 52.3 mmol, Eq: 80) at 0° C. was dropwise added fuming nitric acid (61.8 mg, 43.8 µl, 981 µmol, Eq: 1.50) and the mixture was stirred at 0° C. for 1.5 h. The reaction mixture was poured onto ice and basified with 3 M NaOH-sol. followed by extraction with dichloromethane. The organic layer was separated, dried over Na₂SO₄, filtered and evaporated to dryness to give the crude and pure (3R,4aR)-3-(2-fluoro-5-nitro-phenyl)-3-methyl-4a-oxo-3,4,6,7,8,9-hexahydro-4aλ⁶-thia-2,5,9a-triaza-benzocyclohepten-1-ylamine (232 mg, 653 µmol, 99.8% yield) as a white solid. MS (ISP): m/z=356.2 [M+H]⁺.

A21b2: (3R,4aS)-3-(2-Fluoro-5-nitro-phenyl)-3-methyl-4a-oxo-3,4,6,7,8,9-hexahydro-4aλ⁶-thia-2,5,9a-triaza-benzocyclohepten-1-ylamine

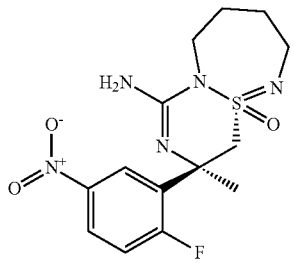 [SMILES: C[C@@]1(c2cc([N+](=O)[O-])ccc2F)C[S@@]2(=O)=NCCCCN2C(N)=N1]

To a solution of (3R,4aS)-3-(2-fluoro-phenyl)-3-methyl-4a-oxo-3,4,6,7,8,9-hexahydro-4aλ⁶-thia-2,5,9a-triaza-benzocyclohepten-1-ylamine (610 mg, 1.97 mmol, Eq: 1.00) in conc. sulfuric acid (15.4 g, 8.38 ml, 157 mmol, Eq: 80) at 0° C. was dropwise added fuming nitric acid (186 mg, 132 µl, 2.95 mol, Eq: 1.50) and the mixture was stirred at 0° C. for 1.5 h. The reaction mixture was poured onto ice and basified with 3 M NaOH-sol. followed by extraction with dichloromethane. The organic layer was separated, dried over Na₂SO₄, filtered and evaporated to dryness to give the crude and pure (3R,4aS)-3-(2-fluoro-5-nitro-phenyl)-3-methyl-4a-oxo-3,4,6,7,8,9-hexahydro-4aλ⁶-thia-2,5,9a-triaza-benzocyclohepten-1-ylamine (550 mg, 1.55 mmol, 78.7% yield) as a white solid. MS (ISP): m/z=356.2 [M+H]+.

A21c: (2S,9R)-7-Amino-9-(2-fluoro-5-nitrophenyl)-9-methyl-2-(trifluoromethyl)-2,3,4,5,9,10-hexahydro-[1,2,4]thiadiazino[1,2-a][1,2,7]thiadiazepine 11-oxide

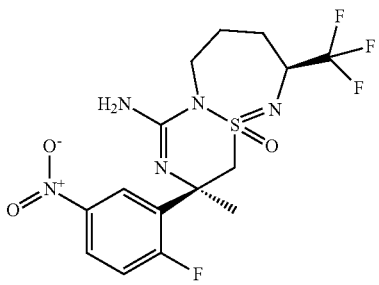 [SMILES: C[C@@]1(c2cc([N+](=O)[O-])ccc2F)CS2(=O)=N[C@H](C(F)(F)F)CCCN2C(N)=N1]

To a solution of (2S,9R)-7-amino-9-(2-fluorophenyl)-9-methyl-2-(trifluoromethyl)-2,3,4,5,9,10-hexahydro-[1,2,4]thiadiazino[1,2-a][1,2,7]thiadiazepine 11-oxide (273 mg, 721 µmol, Eq: 1) in conc. sulfuric acid (5.66 g, 3.08 ml, 57.7 mmol, Eq: 80) at 0° C. was dropwise added fuming nitric acid (68.2 mg, 48.4 µl, 1.08 mmol, Eq: 1.5) and the mixture was stirred at 0° C. for 20 min. The reaction mixture was poured onto ice and cautiously neutralized with sat. NaHCO₃-sol. and solid NaHCO₃, followed by extraction with ethyl acetate. The organic layer was separated, dried over Na₂SO₄, filtered and evaporated to dryness to give the crude material which was purified by chromatography (silica gel, 10 g, 0% to 100% EtOAc in heptane) to give the (2S,9R)-7-amino-9-(2-fluoro-5-nitrophenyl)-9-methyl-2-(trifluoromethyl)-2,3,4,5,9,10-hexahydro-[1,2,4]thiadiazino

[1,2-a][1,2,7]thiadiazepine 11-oxide (mixture of isomers) (260 mg, 614 μmol, 85.1% yield) as a yellow solid. MS (ISP): m/z=424.2 [M+H]$^+$.

A21d: (8R)-6-Amino-3,3-difluoro-8-(2-fluoro-5-nitrophenyl)-8-methyl-3,4,8,9-tetrahydro-2H-[1,2,6]thiadiazino[1,2-a][1,2,4]thiadiazine 10-oxide

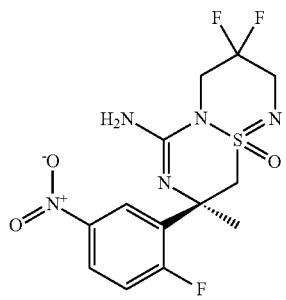

To a solution of (8R)-6-amino-3,3-difluoro-8-(2-fluorophenyl)-8-methyl-3,4,8,9-tetrahydro-2H-[1,2,6]thiadiazino[1,2-a][1,2,4]thiadiazine 10-oxide (53 mg, 159 μmol, Eq: 1) in conc. sulfuric acid (1.25 g, 680 μl, 12.8 mmol, Eq: 80) at 0° C. was dropwise added fuming nitric acid (15.1 mg, 10.7 μl, 239 μmol, Eq: 1.5) and the mixture was stirred at 0° C. for 1 h. The reaction mixture was poured onto ice and cautiously neutralized with sat. NaHCO$_3$-sol. and solid NaHCO$_3$, followed by extraction with DCM. The organic layer was separated, dried over Na$_2$SO$_4$, filtered and evaporated to dryness to give the crude (8R)-6-amino-3,3-difluoro-8-(2-fluoro-5-nitrophenyl)-8-methyl-3,4,8,9-tetrahydro-2H-[1,2,6]thiadiazino[1,2-a][1,2,4]thiadiazine 10-oxide (46 mg, 122 μmol, 76.4% yield) as a light yellow oil which was used without further purification. MS (ISP): m/z=378.1 [M+H]$^+$.

Synthesis of Intermediates A22

A22a1: (3RS,4aRS)-3-(5-amino-2-fluoro-phenyl)-3-methyl-4a-oxo-3,4,6,7,8,9-hexahydro-4aλ$^6$-thia-2,5,9a-triaza-benzocyclohepten-1-ylamine

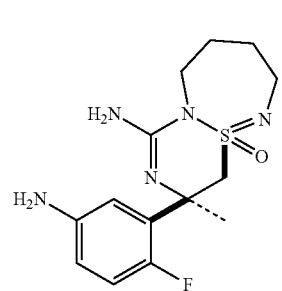

A mixture of (3RS,4aRS)-3-(2-fluoro-5-nitro-phenyl)-3-methyl-4a-oxo-3,4,6,7,8,9-hexahydro-4aλ$^6$-thia-2,5,9a-triaza-benzocyclohepten-1-ylamine (34 mg, 95.7 μmol, Eq: 1.00), triethylamine (9.68 mg, 13.3 μl, 95.7 μmol, Eq: 1.00) and palladium on carbon (10% Pd/C) (10.2 mg, 9.57 μmol, Eq: 0.1) in ethanol (3 ml) was hydrogenated (balloon pressure) at 23° C. for 1 h. Filtered the catalyst off, washed with ethanol and evaporated all volatiles to give the crude (3RS,4aRS)-3-(5-amino-2-fluoro-phenyl)-3-methyl-4a-oxo-3,4,6,7,8,9-hexahydro-4aλ$^6$-thia-2,5,9a-triaza-benzocyclohepten-1-ylamine (34 mg, 94.0 μmol, 98.3% yield) as a yellow foam which was used without further purification. MS (ISP): m/z=326.2 [M+H]$^+$.

A22a2: (3RS,4aSR)-3-(5-amino-2-fluoro-phenyl)-3-methyl-4a-oxo-3,4,6,7,8,9-hexahydro-4aλ$^6$-thia-2,5,9a-triaza-benzocyclohepten-1-ylamine

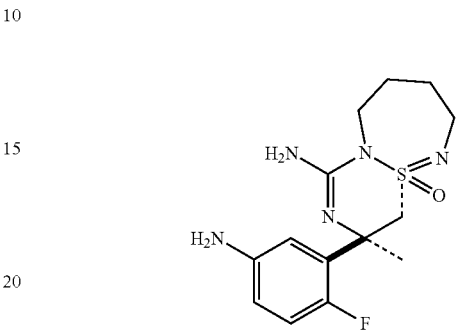

A mixture of (3RS,4aSR)-3-(2-fluoro-5-nitro-phenyl)-3-methyl-4a-oxo-3,4,6,7,8,9-hexahydro-4aλ$^6$-thia-2,5,9a-triaza-benzocyclohepten-1-ylamine (28 mg, 78.8 μmol, Eq: 1.00), triethylamine (7.97 mg, 11.0 μl, 78.8 μmol, Eq: 1.00) and palladium on carbon (10% Pd/C) (8.38 mg, 7.88 μmol, Eq: 0.1) in ethanol (3.00 ml) was hydrogenated (balloon pressure) at 23° C. for 1 h, appears to be not complete, added palladium on carbon (10% Pd/C) (8.38 mg, 7.88 μmol, Eq: 0.1) and continued hydrogenation at 23° C. for 1.5 h. Filtered the catalyst off, washed with ethanol and evaporated all volatiles to give the crude (3RS,4aSR)-3-(5-amino-2-fluoro-phenyl)-3-methyl-4a-oxo-3,4,6,7,8,9-hexahydro-4aλ$^6$-thia-2,5,9a-triaza-benzocyclohepten-1-ylamine (21 mg, 64.5 μmol, 81.9% yield) as a yellow foam which was used without further purification. MS (ISP): m/z=326.2 [M+H]$^+$.

A22b1: (3R,4aR)-3-(5-amino-2-fluoro-phenyl)-3-methyl-4a-oxo-3,4,6,7,8,9-hexahydro-4aλ$^6$-thia-2,5,9a-triaza-benzocyclohepten-1-ylamine

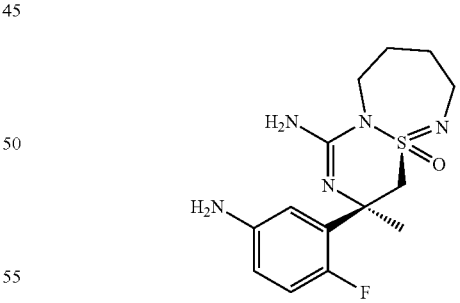

A mixture of (3R,4aR)-3-(2-fluoro-5-nitro-phenyl)-3-methyl-4a-oxo-3,4,6,7,8,9-hexahydro-4aλ$^6$-thia-2,5,9a-triaza-benzocyclohepten-1-ylamine (232 mg, 653 μmol, Eq: 1.00), triethylamine (66.1 mg, 90.1 μl, 653 μmol, Eq: 1.00) and palladium on carbon (10% Pd/C) (69.5 mg, 65.3 μmol, Eq: 0.1) in ethanol (20.4 ml) was hydrogenated (balloon pressure) at 23° C. for 2 h. Filtered the catalyst off, washed with ethanol and evaporated all volatiles to give the crude (3R,4aR)-3-(5-amino-2-fluoro-phenyl)-3-methyl-4a-oxo-3,4,6,7,8,9-hexahydro-4aλ$^6$-thia-2,5,9a-triaza-benzocyclohepten-1-ylamine (212 mg, 651 µmol, 99.8% yield) as a yellow foam which was used without further purification. MS (ISP): m/z=326.1 [M+H]+.

A22b2: (3R,4aS)-3-(5-amino-2-fluoro-phenyl)-3-methyl-4a-oxo-3,4,6,7,8,9-hexahydro-4a$\lambda^6$-thia-2,5,9a-triaza-benzocyclohepten-1-ylamine

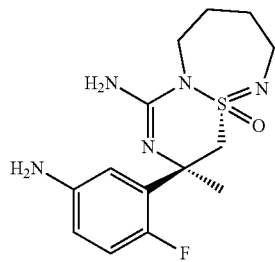 [SMILES: C[C@@]1(c2cc(N)ccc2F)C[S@@]2(=O)=NCCCCN2C(N)=N1]

A mixture of (3R,4aS)-3-(2-fluoro-5-nitro-phenyl)-3-methyl-4a-oxo-3,4,6,7,8,9-hexahydro-4a$\lambda^6$-thia-2,5,9a-triaza-benzocyclohepten-1-ylamine (550 mg, 1.55 mol, Eq: 1.00), triethylamine (157 mg, 216 µl, 1.55 mmol, Eq: 1.00) and palladium on carbon (10% Pd/C) (165 mg, 155 µmol, Eq: 0.1) in ethanol (48.4 ml) was hydrogenated (balloon pressure) at 23° C. for 2 h. Filtered the catalyst off, washed with ethanol and evaporated all volatiles to give the crude (3R,4aS)-3-(5-amino-2-fluoro-phenyl)-3-methyl-4a-oxo-3,4,6,7,8,9-hexahydro-4a$\lambda^6$-thia-2,5,9a-triaza-benzocyclohepten-1-ylamine (504 mg, 1.55 µmol, 100% yield) as a yellow foam which was used without further purification. MS (ISP): m/z=326.2 [M+H]+.

A22c: (2S,9R)-7-Amino-9-(5-amino-2-fluorophenyl)-9-methyl-2-(trifluoromethyl)-2,3,4,5,9,10-hexahydro-[1,2,4]thiadiazino[1,2-a][1,2,7]thiadiazepine 11-oxide

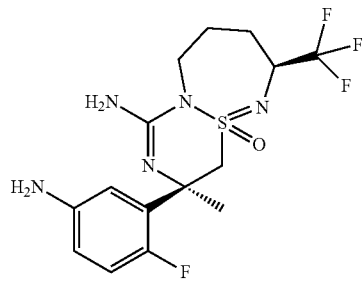 [SMILES: C[C@@]1(c2cc(N)ccc2F)CS2(=O)=N[C@H](C(F)(F)F)CCCN2C(N)=N1]

A mixture of (2S,9R)-7-amino-9-(2-fluoro-5-nitrophenyl)-9-methyl-2-(trifluoromethyl)-2,3,4,5,9,10-hexahydro-[1,2,4]thiadiazino[1,2-a][1,2,7]thiadiazepine 11-oxide (260 mg, 614 µmol, Eq: 1), triethylamine (62.1 mg, 85.6 µl, 614 µmol, Eq: 1.00) and palladium on carbon (10% Pd/C) (65.4 mg, 61.4 µmol, Eq: 0.1) in ethanol (40 ml) was hydrogenated (balloon pressure) at 23° C. for 2 h. Filtered the catalyst off, washed with ethanol and evaporated all volatiles to give the crude (2S,9R)-7-amino-9-(5-amino-2-fluorophenyl)-9-methyl-2-(trifluoromethyl)-2,3,4,5,9,10-hexahydro-[1,2,4]thiadiazino[1,2-a][1,2,7]thiadiazepine 11-oxide (242 mg, 615 µmol, 100% yield) as a yellow foam which was used without further purification. MS (ISP): m/z=394.2 [M+H]+.

A22d: (8R)-6-Amino-8-(5-amino-2-fluorophenyl)-3,3-difluoro-8-methyl-3,4,8,9-tetrahydro-2H-[1,2,6]thiadiazino[1,2-a][1,2,4]thiadiazine 10-oxide

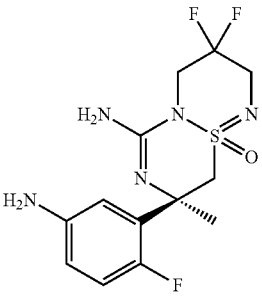 [SMILES: C[C@@]1(c2cc(N)ccc2F)CS2(=O)=NCC(F)(F)CN2C(N)=N1]

A mixture of (8R)-6-amino-3,3-difluoro-8-(2-fluoro-5-nitrophenyl)-8-methyl-3,4,8,9-tetrahydro-2H-[1,2,6]thiadiazino[1,2-a][1,2,4]thiadiazine 10-oxide (46 mg, 122 µmol, Eq: 1), triethylamine (12.3 mg, 17 µl, 122 µmol, Eq: 1) and palladium on carbon (10% Pd/C) (13 mg, 12.2 µmol, Eq: 0.1) in ethanol (10 ml) was hydrogenated (balloon pressure) at 23° C. for 4 h. Filtered the catalyst off, washed with ethanol and evaporated all volatiles to give the crude (8R)-6-amino-8-(5-amino-2-fluorophenyl)-3,3-difluoro-8-methyl-3,4,8,9-tetrahydro-2H-[1,2,6]thiadiazino[1,2-a][1,2,4]thiadiazine 10-oxide (16 mg, 46.1 µmol, 37.8% yield) as a light yellow oil which was used without further purification. MS (ISP): m/z=348.1 [M+H]+.

Synthesis of Intermediates A23

A23a1: (3R,4aR)-3-(2-Fluoro-5-iodo-phenyl)-3-methyl-4a-oxo-3,4,6,7,8,9-hexahydro-4a$\lambda^6$-thia-2,5,9a-triaza-benzocyclohepten-1-ylamine

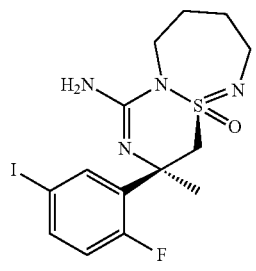 [SMILES: C[C@@]1(c2cc(I)ccc2F)C[S@]2(=O)=NCCCCN2C(N)=N1]

To a solution of (3R,4aR)-3-(2-fluoro-phenyl)-3-methyl-4a-oxo-3,4,6,7,8,9-hexahydro-4a$\lambda^6$-thia-2,5,9a-triaza-benzocyclohepten-1-ylamine (300 mg, 967 µmol, Eq: 1.00) in dichloromethane (5.5 ml) at 0° C. was dropwise added trifluoromethanesulfonic acid (2.9 g, 1.72 ml, 19.3 mmol, Eq: 20) and the mixture was allowed to warm to room temperature. N-iodosuccinimide (261 mg, 1.16 mmol, Eq: 1.2) was added in one portion and the mixture was stirred for 30 minutes. The mixture was added dropwise to sat. NaHCO3 solution (10 ml), extracted with DCM, the organic layer was dried over Na2SO4. Filtration and removal of the solvent in vacuum left a brown oil which was purified by flash chromatography (silica gel, 20 g, 0% to 50% EtOAc in heptane to remove all the unpolar impurity), then washed the column with AcOEt-MeOH—NH4OH 100:10:1, to give the (3R,4aR)-3-(2-fluoro-5-iodo-phenyl)-3-methyl-4a-oxo-3,4, 6,7,8,9-hexahydro-4a$\lambda^6$-thia-2,5,9a-triaza-benzocyclohepten-1-ylamine (412 mg, 944 μmol, 97.7% yield) as a light brown foam. MS (ISP): m/z=437.1 [M+H]$^+$.

A23a2: (3R,4aS)-3-(2-Fluoro-5-iodo-phenyl)-3-methyl-4a-oxo-3,4,6,7,8,9-hexahydro-4a$\lambda^6$-thia-2,5, 9a-triaza-benzocyclohepten-1-ylamine

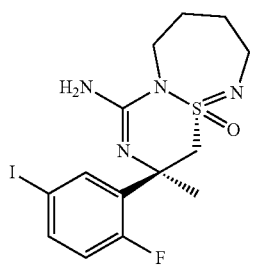 [SMILES: C[C@@]1(c2cc(I)ccc2F)C[S@@]2(=O)=NCCCCN2C(N)=N1]

To a solution of (3R,4aS)-3-(2-fluoro-phenyl)-3-methyl-4a-oxo-3,4,6,7,8,9-hexahydro-4a$\lambda^6$-thia-2,5,9a-triaza-benzocyclohepten-1-ylamine (379 mg, 1.01 mmol, Eq: 1.00) in dichloromethane (7 ml) at 0° C. was dropwise added trifluoromethanesulfonic acid (3.04 g, 1.8 ml, 20.3 mmol, Eq: 20) and the mixture was allowed to warm to room temperature. N-iodosuccinimide (274 mg, 1.22 mmol, Eq: 1.2) was added in one portion and the mixture was stirred for 30 minutes. The mixture was added dropwise to sat. NaHCO$_3$ solution (10 ml), extracted with DCM, the organic layer was dried over Na$_2$SO$_4$. Filtration and removal of the solvent in vacuum left a brown oil which was purified by flash chromatography (silica gel, 20 g, 0% to 50% EtOAc in heptane to remove all the unpolar impurity), then washed the column with AcOEt-MeOH—NH$_4$OH 100:10:1, to give the (3R, 4aS)-3-(2-fluoro-5-iodo-phenyl)-3-methyl-4a-oxo-3,4,6,7, 8,9-hexahydro-4a$\lambda^6$-thia-2,5,9a-triaza-benzocyclohepten-1-ylamine (390 mg, 894 μmol, 88.2% yield) as a light brown foam. MS (ISP): m/z=437.1 [M+H]$^+$.

Synthesis of Intermediates A27

A27a: (R,E)-N-(1-(5-bromo-2-fluorophenyl)ethylidene)-2-methylpropane-2-sulfinamide

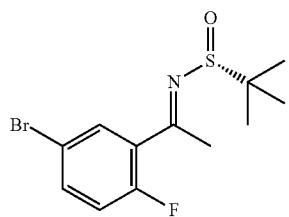 [SMILES: C/C(=N\[S@](=O)C(C)(C)C)c1cc(Br)ccc1F]

Commercially available 1-(5-bromo-2-fluorophenyl)ethanone (140 g, 645 mmol, Eq: 1.0) [CAS No. 477-89-3], (R)-2-methylpropane-2-sulfinamide (78.2, 645 mmol, Eq: 1.0) and titanium(IV) ethoxide (221 g, 204 ml, 968 mmol, Eq: 1.5) were dissolved in tetrahydrofuran (1.19 l) and the mixture heated to 75° C. and stirred at this temperature overnight. The mixture was cooled to 50° C., sat. potassium sodium tartrate solution (1.17 l, 2.58 mol, Eq: 4) was added and the mixture stirred at this temperature for 1.5 hours. The mixture was diluted with TBME, the layers separated, the organic layer washed with sulfuric acid (0.05 M, 2.36 l, 118 mmol, Eq: 0.183), sat. Na$_2$CO$_3$-solution (645 ml, 645 mmol, Eq: 1.00) and brine, dried over Na$_2$SO$_4$ and the solvent evaporated leaving an dark orange solid, which was purified by trituration with n-heptane to give the first batch Synthesis of Intermediates A28

A32a: (R)-N-((R)-1-(5-bromo-2-fluorophenyl)-1-cyanoethyl)-2-methylpropane-2-sulfinamide

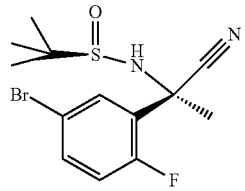 [SMILES: CC(C)(C)[S@@](=O)N[C@@](C)(C#N)c1cc(Br)ccc1F]

To a solution of diethylaluminum cyanide (1 M in toluene, 45.25 ml, 45.25 mmol) was added at 23° C. isopropanol (2.314 ml, 30.17 mmol) and the mixture was stirred at 23° C. for 30 min. The obtained solution was added dropwise within 15 min to a solution of (R,E)-N-(1-(5-bromo-2-fluorophenyl)ethylidene)-2-methylpropane-2-sulfinamide (9.66 g, 30.17 mmol) in tetrahydrofuran (452 ml) at −78° C., stiffing was continued for 5 min, then slowly warmed up to 10° C. and stirred at 10° C. for 5.5 h. Poured into sat. NaHCO$_3$-sol., filtered the precipitate off, washed with ethyl acetate, washed the organic layer with brine and dried over Na$_2$SO$_4$. Removal of the solvent in vacuum left a yellow oil (11.38 g, d.r. 9.9:1) which was purified by crystallization from 2-methyltetrahydrofuran and n-heptane to give the first batch (4.80 g) and the second batch was obtained from the mother liquor by silica gel column chromatography with dichloromethane/TBME 95:5 (2.24 g). Total yield of (R)-N-((R)-1-(5-bromo-2-fluorophenyl)-1-cyanoethyl)-2-methylpropane-2-sulfinamide (7.04 g, 67%) as an off-white solid. MS (ISP): m/z=347.1 [M+H]$^+$ and 349.0 [M+2+H]$^+$.

Synthesis of Intermediates A30

A30a: tert-Butyl ((9R,11S)-9-(2-fluoro-5-iodophenyl)-9-methyl-11-oxido-2,3,4,5,9,10-hexahydro-[1,2,4]thiadiazino[1,2-a][1,2,7]thiadiazepin-7-yl)carbamate

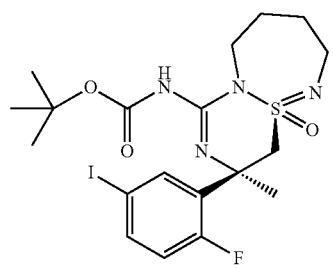 [SMILES: CC(C)(C)OC(=O)NC1=N[C@](C)(c2cc(I)ccc2F)C[S@]2(=O)=NCCCCN12]

Step 1: N-((9R,11S)-9-(2-fluorophenyl)-9-methyl-11-oxido-2,3,4,5,9,10-hexahydro-[1,2,4]thiadiazino[1,2-a][1,2,7]

thiadiazepin-7-yl)benzamide (542 mg) was dissolved in dichloromethane (18 ml) and cooled to 0° C. After addition of trifluoromethanesulfonic acid (3.92 g) the reaction mixture was warmed up to rt and N-iodosuccinimide (206 mg) was added. After 1 h another portion of N-iodosuccinimide (206 mg) was added and the mixture was stirred for 18 h. A third portion of N-iodosuccinimide (206 mg) was added and the mixture was stirred for 2 h. The dark purple mixture was poured on sat. aqueous NaHCO₃ solution. The layers were separated and the aqueous layer was extracted once more with dichloromethane. The org. layers were washed with 0.1M sodiumthiosulphate solution, dried over sodium sulphate and concentrated in vacuo. The mixture (765 mg, mono- and diiodo cpd ~1:2) was submitted to the next step without further purification.

Step 2: The product of step 1 (765 mg) was dissolved in THF (16.9 ml). After addition of Boc-Anhydride (371 mg), 4-dimethylaminopyridine (34.6 mg) and triethylamine (172 mg) the mixture was stirred 18 h at room temperature followed by concentration to dryness. The residual gum was dissolved in MeOH (10.2 ml). After addition of ammonia (10.2 ml, 7M in MeOH) the mixture was stirred for 30 min. The solvent was evaporated and the product was purified by chromatography (silica gel, 0% to 70% EtOAc in n-heptane) to give tert-butyl ((9R,11S)-9-(2-fluoro-5-iodophenyl)-9-methyl-11-oxido-2,3,4,5,9,10-hexahydro-[1,2,4]thiadiazino[1,2-a][1,2,7]thiadiazepin-7-yl)carbamate (289 mg) as a colorless foam. MS: m/z=535.4 [M–H]⁻.

A30 b: tert-Butyl ((9R,11R)-9-(2-fluoro-5-iodophenyl)-9-methyl-11-oxido-2,3,4,5,9,10-hexahydro-[1,2,4]thiadiazino[1,2-a][1,2,7]thiadiazepin-7-yl)carbamate

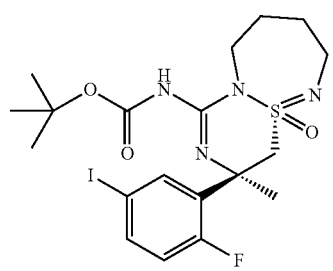 [SMILES: CC(C)(C)OC(=O)NC1=N[C@](C)(c2cc(I)ccc2F)C[S@@]2(=O)=NCCCCN12]

In analogy to the synthesis of Intermediate A30a, N-((9R,11R)-9-(2-fluorophenyl)-9-methyl-11-oxido-2,3,4,5,9,10-hexahydro-[1,2,4]thiadiazino[1,2-a][1,2,7]thiadiazepin-7-yl)benzamide was converted to tert-butyl ((9R,11R)-9-(2-fluoro-5-iodophenyl)-9-methyl-11-oxido-2,3,4,5,9,10-hexahydro-[1,2,4]thiadiazino[1,2-a][1,2,7]thiadiazepin-7-yl)carbamate. Off-white solid. MS: m/z=535.4 [M–H]⁻.

Synthesis of Intermediates A31

A31a: tert-Butyl ((9R,11S)-9-(5-ethynyl-2-fluorophenyl)-9-methyl-11-oxido-2,3,4,5,9,10-hexahydro-[1,2,4]thiadiazino[1,2-a][1,2,7]thiadiazepin-7-yl)carbamate

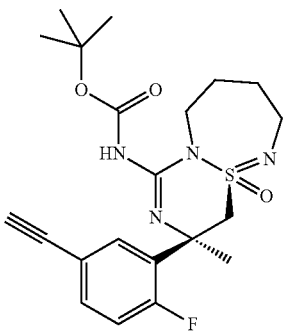 [SMILES: C#Cc1ccc(F)c([C@]2(C)C[S@]3(=O)=NCCCCN3C(NC(=O)OC(C)(C)C)=N2)c1]

Step 1: tert-Butyl ((9R,11S)-9-(2-fluoro-5-iodophenyl)-9-methyl-11-oxido-2,3,4,5,9,10-hexahydro-[1,2,4]thiadiazino[1,2-a][1,2,7]thiadiazepin-7-yl)carbamate (288 mg), ethynyltrimethylsilane (105 mg), bis(triphenylphosphine) palladium (II) chloride (26.4 mg), copper (I) iodide (4.09 mg) and triethylamine (163 mg) were mixed under argon with THF (5 ml) and stirred 30 min at 60° C. in a sealed tube. The mixture was diluted with ethyl acetate and filtered through a glass fibre filter. The filtrate was evaporated and purified by chromatography (silica gel, 0% to 70% EtOAc in n-heptane) to give tert-butyl ((9R,11S)-9-(2-fluoro-5-((trimethylsilyl)ethynyl)phenyl)-9-methyl-11-oxido-2,3,4,5,9,10-hexahydro-[1,2,4]thiadiazino[1,2-a][1,2,7]thiadiazepin-7-yl)carbamate (189 mg) as a light brown foam. MS: m/z=505.4 [M–H]⁻.

Step 2: tert-butyl ((9R,11S)-9-(2-fluoro-5-((trimethylsilyl)ethynyl)phenyl)-9-methyl-11-oxido-2,3,4,5,9,10-hexahydro-[1,2,4]thiadiazino[1,2-a][1,2,7]thiadiazepin-7-yl)carbamate (185 mg) was dissolved in dichloromethane (5 ml). After addition of 3-mercaptopropyl ethyl sulfide silica (scavenger to remove traces of Cu and Pd, 149 mg) the mixture was stirred 4 h at rt. The scavenger was filtered off and washed well with ethyl acetate. The almost colorless sln was evaporated, re-dissolved in dichloromethane (5 ml) and cooled to 0° C. After addition of Tetrabutylammonium fluoride (1M in THF, 402 μl) the mixture was stirred for 30 min at 0° C. The mixture was diluted with dichloromethane and twice washed with water, backextracted with dichloromethane. The combined org. layers were dried over sodium sulphate, evaporated and dried to give almost pure tert-butyl ((9R,11S)-9-(5-ethynyl-2-fluorophenyl)-9-methyl-11-oxido-2,3,4,5,9,10-hexahydro-[1,2,4]thiadiazino[1,2-a][1,2,7]thiadiazepin-7-yl)carbamate (162 mg) as a colorless foam which was used in the next steps without further purification. MS: m/z=433.4 [M–H]⁻.

A31 b: tert-Butyl ((9R,11R)-9-(5-ethynyl-2-fluoro-phenyl)-9-methyl-11-oxido-2,3,4,5,9,10-hexahydro-[1,2,4]thiadiazino[1,2-a][1,2,7]thiadiazepin-7-yl) carbamate

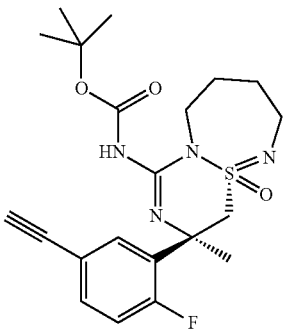 [SMILES: C#Cc1ccc(F)c([C@]2(C)C[S@@]3(=O)=NCCCCN3C(NC(=O)OC(C)(C)C)=N2)c1]

In analogy to the synthesis of Intermediate A31a, tert-butyl ((9R,11R)-9-(2-fluoro-5-iodophenyl)-9-methyl-11-oxido-2,3,4,5,9,10-hexahydro-[1,2,4]thiadiazino[1,2-a][1,2,7]thiadiazepin-7-yl)carbamate was converted to tert-butyl ((9R,11R)-9-(5-ethynyl-2-fluorophenyl)-9-methyl-11-oxido-2,3,4,5,9,10-hexahydro-[1,2,4]thiadiazino[1,2-a][1,2,7] thiadiazepin-7-yl)carbamate. Light yellow solid. MS: m/z=433.5 [M–H]⁻.

Example 1

5-cyano-pyridine-2-carboxylic acid [3-((3RS,4aRS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide To a solution of 5-cyanopyridine-2-carboxylic acid (16.7 mg, 113 µmol, Eq: 1.2) in methanol (2.5 ml) was added at 0° C. 4-(4,6-dimethoxy-1,3,5-triazin-2-yl)-4-methylmorpholinium chloride (DMTMM) (36.4 mg, 132 µmol, Eq: 1.4), the colorless solution was stirred at 0° C. for 30 min, then a solution of (3RS,4aRS)-3-(5-amino-2-fluoro-phenyl)-3-methyl-4a-oxo-3,4,6,7,8,9-hexahydro-4a$\lambda^6$-thia-2,5,9a-triaza-benzocyclohepten-1-ylamine (34 mg, 94.0 µmol, Eq: 1.00) in methanol (1.5 ml) was added dropwise via syringe and the reaction mixture was stirred at 23° C. for 4 h. Extracted with ethyl acetate and sat. NaHCO₃-sol. plus brine, dried organic layer over Na₂SO₄. Filtration and removal of the solvent in vacuum left an orange foam (47 mg) which was purified by flash chromatography (silica gel, 12 g, 100% to 100% EtOAc in heptane, then EtOAc-MeOH—NH₄OH 50:1:0.1) to give the 5-cyano-pyridine-2-carboxylic acid [3-((3RS,4aRS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide (20 mg, 43.9 µmol, 46.7% yield) as a yellow solid. MS (ISP): m/z=456.3 [(M+H)⁺].

Example 2

5-cyano-pyridine-2-carboxylic acid [3-((3RS,4aSR)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide To a solution of 5-cyanopyridine-2-carboxylic acid (16 mg, 108 µmol, Eq: 1.67) in methanol (2.28 ml) was added at 0° C. 4-(4,6-dimethoxy-1,3,5-triazin-2-yl)-4-methylmorpholinium chloride (DMTMM) (30 mg, 108 µmol, Eq: 1.68), the colorless solution was stirred at 0° C. for 30 min, then a solution of (3RS,4aSR)-3-(5-amino-2-fluoro-phenyl)-3-methyl-4a-oxo-3,4,6,7,8,9-hexahydro-4a$\lambda^6$-thia-2,5,9a-triaza-benzocyclohepten-1-ylamine (21 mg, 64.5 µmol, Eq: 1.00) in methanol (1.37 ml) was added dropwise via syringe and the reaction mixture was stirred at 23° C. for 16 h. Extracted with ethyl acetate and sat. NaHCO₃-sol. plus brine, dried organic layer over Na₂SO₄. Filtration and removal of the solvent in vacuum left an orange foam which was purified by flash chromatography (silica gel, 12 g, 100% to 100% EtOAc in heptane, then EtOAc-MeOH—NH₄OH 50:1:0.1) to give the 5-cyano-pyridine-2-carboxylic acid [3-((3RS,4aSR)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide (10 mg, 22.0 µmol, 34.0% yield) as a yellow solid. MS (ISP): m/z=456.3 [(M+H)⁺].

Example 3

5-cyano-pyridine-2-carboxylic acid [3-((3R,4aR)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide To a solution of 5-cyanopyridine-2-carboxylic acid (38.2 mg, 258 µmol, Eq: 1.2) in methanol (3 ml) was added at 0° C. 4-(4,6-dimethoxy-1,3,5-triazin-2-yl)-4-methylmorpholinium chloride (DMTMM) (83.3 mg, 301 µmol, Eq: 1.4), the colorless solution was stirred at 0° C. for 30 min, then a solution of (3R,4aR)-3-(5-amino-2-fluoro-phenyl)-3-methyl-4a-oxo-3,4,6,7,8,9-hexahydro-4a$\lambda^6$-thia-2,5,9a-triaza-benzocyclohepten-1-ylamine (70 mg, 215 µmol, Eq: 1.00) in methanol (5 ml) was added dropwise via syringe and the reaction mixture was stirred at 23° C. for 3 h. Extracted with ethyl acetate and sat. NaHCO₃-sol. plus brine, dried organic layer over Na₂SO₄. Filtration and removal of the solvent in vacuum left a brown foam which was purified by flash chromatography (NH₂-silica gel, 20 g, 0% to 100% EtOAc in heptane) to give the 5-cyano-pyridine-2-carboxylic acid [3-((3R,4aR)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide (62 mg, 136 µmol, 63.3% yield) as an off-white foam. MS (ISP): m/z=456.2 [(M+H)⁺].

Example 4

5-cyano-pyridine-2-carboxylic acid [3-((3R,4aS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide To a solution of 5-cyanopyridine-2-carboxylic acid (38.2 mg, 258 µmol, Eq: 1.2) in methanol (3 ml) was added at 0° C. 4-(4,6-dimethoxy-1,3,5-triazin-2-yl)-4-methylmorpholinium chloride (DMTMM) (83.3 mg, 301 µmol, Eq: 1.4), the colorless solution was stirred at 0° C. for 30 min, then a solution of (3R,4aS)-3-(5-amino-2-fluoro-phenyl)-3-methyl-4a-oxo-3,4,6,7,8,9-hexahydro-4a$\lambda^6$-thia-2,5,9a-triaza-benzocyclohepten-1-ylamine (70 mg, 215 µmol, Eq: 1.00) in methanol (5 ml) was added dropwise via syringe and the reaction mixture was stirred at 23° C. for 3 h. Extracted with ethyl acetate and sat. NaHCO₃-sol. plus brine, dried organic layer over Na₂SO₄. Filtration and removal of the solvent in vacuum left a brown foam which was purified by flash chromatography (NH$_2$-silica gel, 20 g, 0% to 100% EtOAc in heptane) to give the 5-cyano-pyridine-2-carboxylic acid [3-((3R,4aS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide (69 mg, 151 µmol, 70.4% yield) as an off-white foam. MS (ISP): m/z=456.2 [(M+H)$^+$].

Example 5

5-[3-((3R,4aR)-1-Amino-3-methyl-4a-oxo-3,4,6,7,8,9-hexahydro-4a$\lambda^6$-thia2,5,9a-triaza-benzocyclohepten-3-yl)-4-fluoro-phenyl]-nicotinonitrile To a solution of (3R,4aR)-3-(2-fluoro-5-iodo-phenyl)-3-methyl-4a-oxo-3,4,6,7,8,9-hexahydro-4a$\lambda^6$-thia-2,5,9a-triaza-benzocyclohepten-1-ylamine (135 mg, 309 µmol, Eq: 1.00) in tetrahydrofuran (5 ml) and water (2.5 ml) at room temperature was added 5-cyano-3-pyridinyl boronic acid (54.9 mg, 371 µmol, Eq: 1.2), cesium carbonate (403 mg, 1.24 mmol, Eq: 4) and under argon 1,1'-bis(diphenylphosphino)ferrocene-palladium(II)dichloride dichloromethane complex (PdCl$_2$(dppf)-CH$_2$Cl$_2$) (25.3 mg, 30.9 µmol, Eq: 0.1) the mixture was stirred in a sealed tube at 80° C. for 16 hours. Poured into sat. NaHCO$_3$-sol., extracted with ethyl acetate, the organic layer was dried over Na$_2$SO$_4$. Removal of the solvent in vacuum left a black oil which was purified by flash chromatography (first: NH$_2$-silica gel, 20 g, 0% to 100% EtOAc in heptane; second: silica gel, 20 g, CH$_2$Cl$_2$-MeOH—NH$_4$OH 100:5:0.5) to give the 5-[3-((3R,4aR)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-nicotinonitrile (27 mg, 65.5 µmol, 21.2% yield) as a white solid. MS (ISP): m/z=413.2 [(M+H)$^+$].

Example 6

(3R,4aR)-3-(2-Fluoro-5-pyrimidin-5-yl-phenyl)-3-methyl-4a-oxo-3,4,6,7,8,9hexahydro-4a$\lambda^6$-thia-2,5,9a-triaza-benzocyclohepten-1-ylamine To a solution of (3R,4aR)-3-(2-fluoro-5-iodo-phenyl)-3-methyl-4a-oxo-3,4,6,7,8,9-hexahydro-4a$\lambda^6$-thia-2,5,9a-triaza-benzocyclohepten-1-ylamine (135 mg, 309 µmol, Eq: 1.00) in tetrahydrofuran (5 ml) and water (2.5 ml) at room temperature was added pyrimidin-5-ylboronic acid (46.0 mg, 371 µmol, Eq: 1.2), cesium carbonate (403 mg, 1.24 mmol, Eq: 4) and under argon 1,1'-bis(diphenylphosphino)ferrocene-palladium(II)dichloride dichloromethane complex (PdCl$_2$(dppf)-CH$_2$Cl$_2$) (25.3 mg, 30.9 µmol, Eq: 0.1) the mixture was stirred in a sealed tube at 80° C. for 16 hours. Poured into sat. NaHCO3-sol., extracted with ethyl acetate, the organic layer was dried over Na$_2$SO$_4$. Removal of the solvent in vacuum left a black oil which was purified by flash chromatography (first: NH$_2$-silica gel, 20 g, 0% to 100% EtOAc in heptane; second: silica gel, 20 g, CH$_2$Cl$_2$-MeOH—NH$_4$OH 100:5:0.5) to give the (3R,4aR)-3-(2-fluoro-5-pyrimidin-5-yl-phenyl)-3-methyl-4a-oxo-3,4,6,7,8,9hexahydro-4a$\lambda^6$-thia-2,5,9a-triaza-benzocyclohepten-1-ylamine (20 mg, 51.5 µmol, 16.6% yield) as a white solid. MS (ISP): m/z=389.2 [(M+H)$^+$].

Example 7

5-Chloro-pyridine-2-carboxylic acid [3-((3R,4aR)-1-amino-3-methyl-4a-oxo-3,4,6,7,8,9-hexahydro-4$\lambda^6$-thia-2,5,9a-triaza-benzocyclohepten-3-yl)-4-fluoro-phenyl]-amide

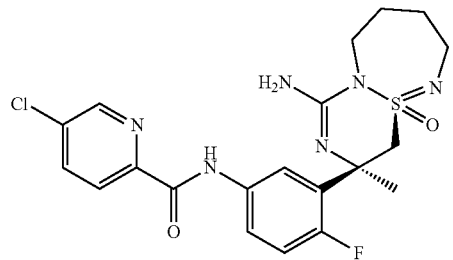 [SMILES: C[C@@]1(c2cc(NC(=O)c3ccc(Cl)cn3)ccc2F)C[S@]2(=O)=NCCCCN2C(N)=N1]

To a solution of 5-chloropicolinic acid (33.9 mg, 215 µmol, Eq: 1.2) in methanol (3 ml) was added at 0° C. 4-(4,6-dimethoxy-1,3,5-triazin-2-yl)-4-methylmorpholinium chloride (DMTMM) (83.3 mg, 301 µmol, Eq: 1.4), the colorless solution was stirred at 0° C. for 30 min, then a solution of (3R,4aR)-3-(5-amino-2-fluoro-phenyl)-3-methyl-4a-oxo-3,4,6,7,8,9-hexahydro-4a$\lambda^6$-thia-2,5,9a-triaza-benzocyclohepten-1-ylamine (70 mg, 215 µmol, Eq: 1.00) in methanol (5 ml) was added dropwise via syringe and the reaction mixture was stirred at 23° C. for 3 h. Extracted with ethyl acetate and sat. NaHCO$_3$-sol. plus brine, dried organic layer over Na$_2$SO$_4$. Filtration and removal of the solvent in vacuum left a brown foam which was purified by flash chromatography (NH$_2$-silica gel, 20 g, 0% to 100% EtOAc in heptane) to give the 5-chloro-pyridine-2-carboxylic acid [3-((3R,4aR)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide (62 mg, 133 µmol, 62.0% yield) as an off-white foam. MS (ISP): m/z=465.2 [(M+H)$^+$].

Example 8

5-[3-((3R,4aS)-1-Amino-3-methyl-4a-oxo-3,4,6,7,8,9-hexahydro-4a$\lambda^6$-thia2,5,9a-triaza-benzocyclohepten-3-yl)-4-fluoro-phenyl]-nicotinonitrile To a solution of (3R,4aS)-3-(2-fluoro-5-iodo-phenyl)-3-methyl-4a-oxo-3,4,6,7,8,9-hexahydro-4a$\lambda^6$-thia-2,5,9a-triaza-benzocyclohepten-1-ylamine (130 mg, 298 µmol, Eq: 1.00) in tetrahydrofuran (5 ml) and water (2.5 ml) at room temperature was added 5-cyano-3-pyridinyl boronic acid (52.9 mg, 358 µmol, Eq: 1.2), cesium carbonate (388 mg, 1.19 mmol, Eq: 4) and under argon 1,1'-bis(diphenylphosphino)ferrocene-palladium(II)dichloride dichloromethane complex (PdCl$_2$(dppf)-CH$_2$Cl$_2$) (24.3 mg, 29.8 µmol, Eq: 0.1) the mixture was stirred in a sealed tube at 80° C. for 16 hours. Poured into sat. NaHCO$_3$-sol., extracted with ethyl acetate, the organic layer was dried over Na$_2$SO$_4$. Removal of the solvent in vacuum left a brown oil which was purified by flash chromatography (first: NH$_2$-silica gel, 20 g, 0% to 100% EtOAc in heptane; second: silica gel, 20 g, CH$_2$Cl$_2$-MeOH—NH$_4$OH 100:5:0.5) to give the 5-[3-((3R,4aS)-1-amino-3-methyl-4a-oxo-3,4,6,7,8,9-hexahydro-4a$\lambda^6$-thia2,5,9a-triaza-benzocyclohepten-3-yl)-4-fluoro-phenyl]- nicotinonitrile (41 mg, 99.4 μmol, 33.4% yield) as a white solid. MS (ISP): m/z=413.2 [(M+H)±].

Example 9

(3R,4aS)-3-(2-Fluoro-5-pyrimidin-5-yl-phenyl)-3-methyl-4a-oxo-3,4,6,7,8,9hexahydro-4a$\lambda^6$-thia-2,5,9a-triaza-benzocyclohepten-1-ylamine To a solution of (3R,4aS)-3-(2-fluoro-5-iodo-phenyl)-3-methyl-4a-oxo-3,4,6,7,8,9-hexahydro-4a$\lambda^6$-thia-2,5,9a-triaza-benzocyclohepten-1-ylamine (130 mg, 298 μmol, Eq: 1.00) in tetrahydrofuran (5 ml) and water (2.5 ml) at room temperature was added pyrimidin-5-ylboronic acid (44.3 mg, 358 μmol, Eq: 1.2), cesium carbonate (388 mg, 1.19 mmol, Eq: 4) and under argon 1,1'-bis(diphenylphosphino)ferrocene-palladium(II)dichloride dichloromethane complex (PdCl$_2$(dppf)-CH$_2$Cl$_2$) (24.3 mg, 29.8 μmol, Eq: 0.1) the mixture was stirred in a sealed tube at 80° C. for 16 hours. Poured into sat. NaHCO3-sol., extracted with ethyl acetate, the organic layer was dried over Na$_2$SO$_4$. Removal of the solvent in vacuum left a brown oil which was purified by flash chromatography (first: NH$_2$-silica gel, 20 g, 0% to 100% EtOAc in heptane; second: silica gel, 20 g, CH$_2$Cl$_2$-MeOH—NH$_4$OH 100:5:0.5) to give the (3R,4aS)-3-(2-fluoro-5-pyrimidin-5-yl-phenyl)-3-methyl-4a-oxo-3,4,6,7,8,9hexahydro-4a$\lambda^6$-thia-2,5,9a-triaza-benzocyclohepten-1-ylamine (22 mg, 56.6 μmol, 19.0% yield) as a white solid. MS (ISP): m/z=389.2 [(M+H)$^+$].

Example 10

5-Cyano-3-methyl-pyridine-2-carboxylic acid [3-((3R,4aR)-1-amino-3-methyl-4a-oxo-3,4,6,7,8,9-hexahydro-4$\lambda^6$-thia-2,5,9a-triaza-benzocyclohepten-3-yl)-4-fluoro-phenyl]-amide

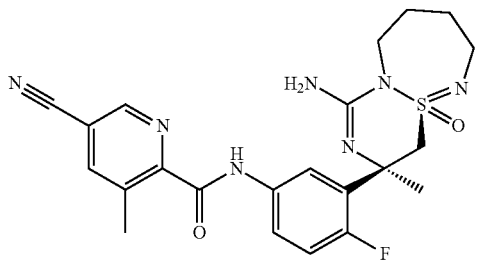 [SMILES: Cc1cc(C#N)cnc1C(=O)Nc1ccc(F)c([C@]2(C)C[S@]3(=O)=NCCCCN3C(N)=N2)c1]

To a solution of 5-cyano-3-methylpicolinic acid (41.9 mg, 258 μmol, Eq: 1.2) in methanol (3 ml) was added at 0° C. 4-(4,6-dimethoxy-1,3,5-triazin-2-yl)-4-methylmorpholinium chloride (DMTMM) (83.3 mg, 301 μmol, Eq: 1.4), the colorless solution was stirred at 0° C. for 30 min, then a solution of (3R,4aR)-3-(5-amino-2-fluoro-phenyl)-3-methyl-4a-oxo-3,4,6,7,8,9-hexahydro-4a$\lambda^6$-thia-2,5,9a-triaza-benzocyclohepten-1-ylamine (70 mg, 215 μmol, Eq: 1.00) in methanol (5 ml) was added dropwise via syringe and the reaction mixture was stirred at 23° C. for 3 h. Extracted with ethyl acetate and sat. NaHCO$_3$-sol. plus brine, dried organic layer over Na$_2$SO$_4$. Filtration and removal of the solvent in vacuum left a brown foam which was purified by flash chromatography (NH$_2$-silica gel, 20 g, 0% to 100% EtOAc in heptane) to give the 5-cyano-3-methyl-pyridine-2-carboxylic acid [3-((3R,4aR)-1-amino-3-methyl-4a-oxo-3,4,6,7,8,9-hexahydro-4$\lambda^6$-thia-2,5,9a-triaza-benzocyclohepten-3-yl)-4-fluoro-phenyl]-amide (60 mg, 128 μmol, 59.4% yield) as an off-white foam. MS (ISP): m/z=470.2 [(M+H)±].

Example 11

5-Chloro-pyridine-2-carboxylic acid [3-((3R,4aS)-1-amino-3-methyl-4a-oxo-3,4,6,7,8,9-hexahydro-4$\lambda^6$-thia-2,5,9a-triaza-benzocyclohepten-3-yl)-4-fluoro-phenyl]-amide

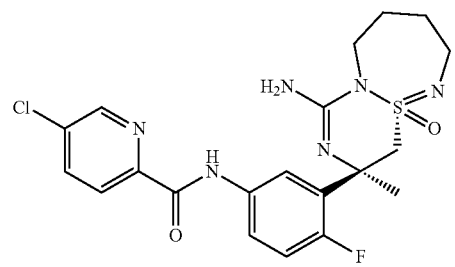 [SMILES: C[C@@]1(c2cc(NC(=O)c3ccc(Cl)cn3)ccc2F)C[S@@]2(=O)=NCCCCN2C(N)=N1]

To a solution of 5-chloropicolinic acid (40.7 mg, 258 μmol, Eq: 1.2) in methanol (3 ml) was added at 0° C. 4-(4,6-dimethoxy-1,3,5-triazin-2-yl)-4-methylmorpholinium chloride (DMTMM) (83.3 mg, 301 μmol, Eq: 1.4), the colorless solution was stirred at 0° C. for 30 min, then a solution of (3R,4aS)-3-(5-amino-2-fluoro-phenyl)-3-methyl-4a-oxo-3,4,6,7,8,9-hexahydro-4a$\lambda^6$-thia-2,5,9a-triaza-benzocyclohepten-1-ylamine (70 mg, 215 μmol, Eq: 1.00) in methanol (5 ml) was added dropwise via syringe and the reaction mixture was stirred at 23° C. for 3 h. Extracted with ethyl acetate and sat. NaHCO$_3$-sol. plus brine, dried organic layer over Na$_2$SO$_4$. Filtration and removal of the solvent in vacuum left a brown foam which was purified by flash chromatography (NH$_2$-silica gel, 20 g, 0% to 100% EtOAc in heptane) to give the 5-chloro-pyridine-2-carboxylic acid [3-((3R,4aS)-1-amino-3-methyl-4a-oxo-3,4,6,7,8,9-hexahydro-4$\lambda^6$-thia-2,5,9a-triaza-benzo-cyclohepten-3-yl)-4-fluoro-phenyl]-amide (63 mg, 136 μmol, 63.0% yield) as an off-white foam. MS (ISP): m/z=465.2 [(M+H)$^+$].

Example 12

5-Cyano-3-methyl-pyridine-2-carboxylic acid [3-((3R,4aS)-1-amino-3-methyl-4a-oxo-3,4,6,7,8,9-hexahydro-4$\lambda^6$-thia-2,5,9a-triaza-benzocyclohepten-3-yl)-4-fluoro-phenyl]-amide

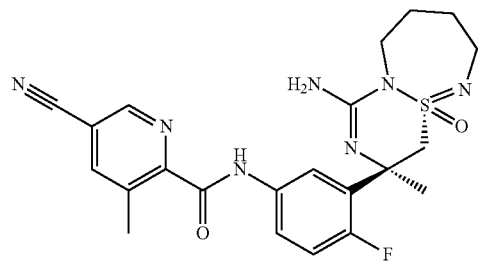

To a solution of 5-cyano-3-methylpicolinic acid (41.9 mg, 258 µmol, Eq: 1.2) in methanol (3 ml) was added at 0° C. 4-(4,6-dimethoxy-1,3,5-triazin-2-yl)-4-methylmorpholinium chloride (DMTMM) (83.3 mg, 301 µmol, Eq: 1.4), the colorless solution was stirred at 0° C. for 30 min, then a solution of (3R,4aS)-3-(5-amino-2-fluoro-phenyl)-3-methyl-4a-oxo-3,4,6,7,8,9-hexahydro-4a$\lambda^6$-thia-2,5,9a-triaza-benzocyclohepten-1-ylamine (70 mg, 215 µmol, Eq: 1.00) in methanol (5 ml) was added dropwise via syringe and the reaction mixture was stirred at 23° C. for 3 h. Extracted with ethyl acetate and sat. NaHCO$_3$-sol. plus brine, dried organic layer over Na$_2$SO$_4$. Filtration and removal of the solvent in vacuum left a brown foam which was purified by flash chromatography (NH$_2$-silica gel, 20 g, 0% to 100% EtOAc in heptane) to give the 5-cyano-3-methyl-pyridine-2-carboxylic acid [3-((3R,4aS)-1-amino-3-methyl-4a-oxo-3,4,6,7,8,9-hexahydro-4$\lambda^6$-thia-2,5,9a-triaza-benzocyclohepten-3-yl)-4-fluoro-phenyl]-amide (69 mg, 147 µmol, 68.3% yield) as an off-white foam. MS (ISP): m/z=470.2 [(M+H)$^+$].

Example 13

(9R,11R)-7-Amino-9-(5-(3-(5-chloropyrimidin-2-yl)isoxazol-5-yl)-2-fluorophenyl)-9-methyl-2,3,4,5,9,10-hexahydro-[1,2,4]thiadiazino[1,2-a][1,2,7]thiadiazepine 11-oxide 2,2,2-trifluoroacetate

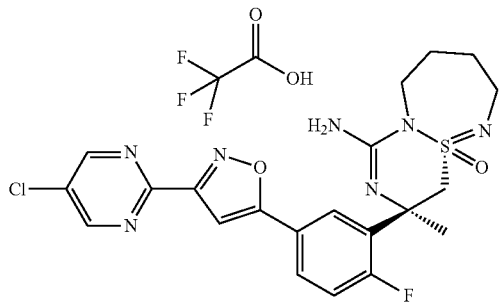

Step 1: To a stirred suspension of 5-chloropyrimidine-2-carbonitrile (CAS#38275-56-8, 1 g) in ethanol (10.7 ml) hydroxylamine hydrochloride (523 mg) and 1 M sodium hydroxide solution (7.24 ml) were added. The reaction mixture was stirred at r.t. over night.
The suspension was filtered through sintered glass, washed with cold water and dried to give 5-chloro-N'-hydroxypyrimidine-2-carboximidamide (1.08 g) as a colorless solid. MS: m/z=173.0 [M+H]$^+$.
Step 2: To a suspension of 5-chloro-N'-hydroxypyrimidine-2-carboximidamide (1.08 g) in 3.7 M aqueous hydrochloric acid (17.6 ml), a solution of sodium nitrite (535 mg) in water (2.83 ml) was dropwise added while stiffing at 0° C. under argon. The reaction mixture was stirred at 0° C. for 1 h 30 min. About 8 mL NaHCO3 sat. sol. in water were slowly added while stirring at 0° C. under argon (pH-value still in the acidic range). The suspension was filtered through sintered glass, the residue was washed with cold water and dried to give 5-chloro-N-hydroxypyrimidine-2-carbimidoyl chloride (1.019 g). Off-white solid. MS: m/z=192.0 [M+H]$^+$.
Step 3: tert-butyl ((9R,11R)-9-(5-ethynyl-2-fluorophenyl)-9-methyl-11-oxido-2,3,4,5,9,10-hexahydro-[1,2,4]thiadiazino[1,2-a][1,2,7]thiadiazepin-7-yl)carbamate (58 mg) was dissolved in THF (3 ml). After addition of 5-chloro-N-hydroxypyrimidine-2-carbimidoyl chloride (51.3 mg) and sodium bicarbonate (22.4 mg) the mixture was stirred for 4 days at rt. After addition of ethyl acetate the mixture was filtered, evaporated and purified by chromatography (silica gel, 0% to 80% EtOAc in n-heptane) to give tert-butyl ((9R,11R)-9-(5-(3-(5-chloropyrimidin-2-yl)isoxazol-5-yl)-2-fluorophenyl)-9-methyl-11-oxido-2,3,4,5,9,10-hexahydro-[1,2,4]thiadiazino [1,2-a][1,2,7]thiadiazepin-7-yl)carbamate (37 mg) as colorless solid. MS: m/z=588.5 [M−H]$^-$.
Step 4: tert-Butyl ((9R,11R)-9-(5-(3-(5-chloropyrimidin-2-yl)isoxazol-5-yl)-2-fluorophenyl)-9-methyl-11-oxido-2,3,4,5,9,10-hexahydro-[1,2,4]thiadiazino [1,2-a][1,2,7]thiadiazepin-7-yl)carbamate (36.5 mg) was dissolved in dichloromethane (1 ml). After addition of trifluoroacetic acid (444 mg) the mixture was stirred for 30 min at rt. The solvent was evaporated, the colorless gum was co-evaporated twice with dichloromethane-heptane and dried to give (9R,11R)-7-amino-9-(5-(3-(5-chloropyrimidin-2-yl)isoxazol-5-yl)-2-fluorophenyl)-9-methyl-2,3,4,5,9,10-hexahydro-[1,2,4]thiadiazino [1,2-a][1,2,7]thiadiazepine 11-oxide 2,2,2-trifluoroacetate (38 mg) as white solid. MS: m/z=490.3 [M+H]$^+$.

Example 14

(9R,11S)-7-Amino-9-(5-(3-(5-chloropyrimidin-2-yl)isoxazol-5-yl)-2-fluorophenyl)-9-methyl-2,3,4,5,9,10-hexahydro-[1,2,4]thiadiazino[1,2-a][1,2,7]thiadiazepine 11-oxide 2,2,2-trifluoroacetate

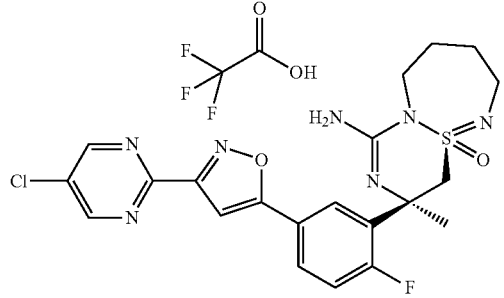

Step 1: In analogy to Example 13, step 3, tert-butyl ((9R,11S)-9-(5-ethynyl-2-fluorophenyl)-9-methyl-11-oxido-2,3,4,5,9,10-hexahydro-[1,2,4]thiadiazino [1,2-a][1,2,7]thiadiazepin-7-yl)carbamate was converted to tert-butyl ((9R,11S)-9-(5-(3-(5-chloropyrimidin-2-yl)isoxazol-5-yl)-2-fluorophenyl)-9-methyl-11-oxido-2,3,4,5,9,10-hexahydro-[1,2,4]thiadiazino [1,2-a][1,2,7]thiadiazepin-7-yl)carbamate by treatment with 5-chloro-N-hydroxypyrimidine-2-carbimidoyl chloride in the presence of sodium bicarbonate. Colorless solid. MS: m/z=590.6 [M+H]$^+$.
Step 2: In analogy to Example 13, step 4, tert-butyl ((9R,11S)-9-(5-(3-(5-chloropyrimidin-2-yl)isoxazol-5-yl)-2-fluorophenyl)-9-methyl-11-oxido-2,3,4,5,9,10-hexahydro-[1,2,4]thiadiazino[1,2-a][1,2,7]thiadiazepin-7-yl)carbamate was converted to (9R,11S)-7-amino-9-(5-(3-(5-chloropyrimidin-2-yl)isoxazol-5-yl)-2-fluorophenyl)-9-methyl-2,3,4,5,9,10-hexahydro-[1,2,4]thiadiazino [1,2-a][1,2,7]thiadiazepine 11-oxide 2,2,2-trifluoroacetate by treatment with trifluoroacetic acid in dichloromethane. Colorless solid. MS: m/z=490.3 [M+H]$^+$.

Example 15

6-(4-(3-((9R,11S)-7-Amino-9-methyl-11-oxido-2,3,4,5,9,10-hexahydro-[1,2,4]thiadiazino[1,2-a][1,2,7]thiadiazepin-9-yl)-4-fluorophenyl)-1H-1,2,3-triazol-1-yl)nicotinonitrile 2,2,2-trifluoroacetate

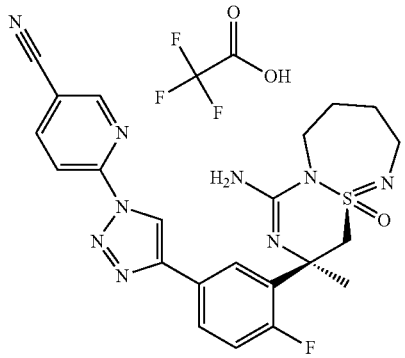

Step 1: tert-butyl ((9R,11S)-9-(5-ethynyl-2-fluorophenyl)-9-methyl-11-oxido-2,3,4,5,9,10-hexahydro-[1,2,4]thiadiazino [1,2-a][1,2,7]thiadiazepin-7-yl)carbamate (50 mg) and 6-azidonicotinonitrile (16.7 mg) were mixed under argon with toluene (1.5 ml). After addition of copper(I) trifluoromethanesulfonate benzene complex (5.79 mg) the mixture was stirred for 10 days at rt in a sealed tube. The mixture was diluted with ethyl acetate, filtered through a glass fibre filter, evaporated and purified by chromatography (silica gel, 0% to 80% EtOAc in n-heptane) to give tert-butyl ((9R,11S)-9-(5-(1-(5-cyanopyridin-2-yl)-1H-1,2,3-triazol-4-yl)-2-fluorophenyl)-9-methyl-11-oxido-2,3,4,5,9,10-hexahydro-[1,2,4]thiadiazino [1,2-a][1,2,7]thiadiazepin-7-yl)carbamate (41 mg) as colorless solid. MS: m/z=580.4 [M+H]$^+$.

Step 2: In analogy to Example 13, step 4, tert-butyl ((9R,11S)-9-(5-(1-(5-cyanopyridin-2-yl)-1H-1,2,3-triaz ol-4-yl)-2-fluorophenyl)-9-methyl-11-oxido-2,3,4,5,9,10-hexahydro-[1,2,4]thiadiazino[1,2-a][1,2,7]thiadiazepin-7-yl)carbamate was converted to 6-(4-(3-((9R,11S)-7-amino-9-methyl-11-oxido-2,3,4,5,9,10-hexahydro-[1,2,4]thiadiazino [1,2-a][1,2,7]thiadiazepin-9-yl)-4-fluorophenyl)-1H-1,2,3-triazol-1-yl)nicotinonitrile 2,2,2-trifluoroacetate by treatment with trifluoroacetic acid in dichloromethane. Colorless solid. MS: m/z=480.3 [M+H]+.

Example 16

4-43-49R,11R)-7-Amino-9-methyl-11-oxido-2,3,4,5,9,10-hexahydro-[1,2,4]thiadiazino[1,2-a][1,2,7]thiadiazepin-9-yl)-4-fluorophenyl)ethynyl)benzonitrile 2,2,2-trifluoroacetate

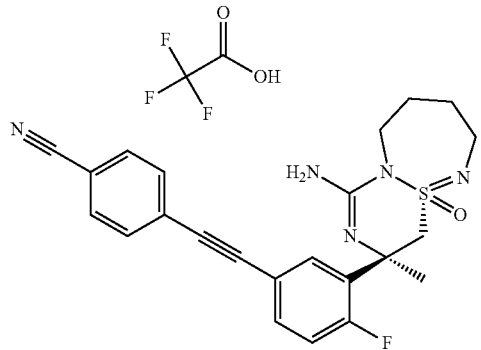

Step 1: tert-Butyl ((9R,11R)-9-(2-fluoro-5-iodophenyl)-9-methyl-11-oxido-2,3,4,5,9,10-hexahydro-[1,2,4]thiadiazino[1,2-a][1,2,7]thiadiazepin-7-yl)carbamate (66 mg), 4-((trimethylsilyl)ethynyl)benzonitrile (29.4 mg), tetramethylammonium fluoride (13.8 mg), bis(triphenylphosphine)palladium (II) chloride (6.05 mg), copper (I) iodide (937 µg) and triethylamine (62.3 mg) were mixed under argon and stirred 1 h at 50° C. in a sealed tube. The mixture was diluted with ethyl acetate, filtered through a glass fibre filter, evaporated and purified by chromatography (silica gel, 0% to 80% EtOAc in n-heptane). The product-containing fractions were collected, decolorized with charcoal, evaporated and dried to give tert-butyl ((9R,11R)-9-(5-((4-cyanophenyl)ethynyl)-2-fluorophenyl)-9-methyl-11-oxido-2,3,4,5,9,10-hexahydro-[1,2,4]thiadiazino[1,2-a][1,2,7]thiadiazepin-7-yl)carbamate (50 mg) as colorless solid. MS: m/z=536.4 [M+H]+.

Step 2: In analogy to Example 13, step 4, tert-butyl ((9R,11R)-9-(5-((4-cyanophenyl)ethynyl)-2-fluorophenyl)-9-methyl-11-oxido-2,3,4,5,9,10-hexahydro-[1,2,4]thiadiazino [1,2-a][1,2,7]thiadiazepin-7-yl)carbamate was converted to 4-((3-((9R,11R)-7-amino-9-methyl-11-oxido-2,3,4,5,9,10-hexahydro-[1,2,4]thiadiazino [1,2-a][1,2,7]thiadiazepin-9-yl)-4-fluorophenyl)ethynyl)benzonitrile 2,2,2-trifluoroacetate by treatment with trifluoroacetic acid in dichloromethane. Light yellow solid. MS: m/z=436.4 [M+H]+.

Example 17

(9R,11R)-7-Amino-9-(2-fluoro-5-(3-(5-methoxypyrazin-2-yl)isoxazol-5-yl)phenyl)-9-methyl-2,3,4,5,9,10-hexahydro-[1,2,4]thiadiazino[1,2-a][1,2,7]thiadiazepine 11-oxide 2,2,2-trifluoroacetate

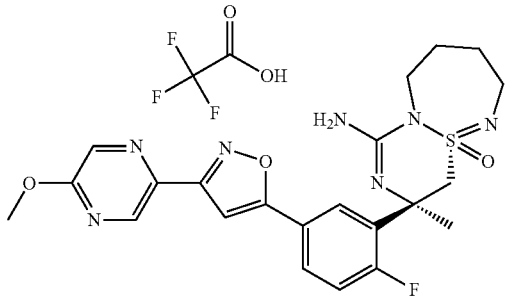

Step 1: In analogy to Example 13, step 2, N'-hydroxy-5-methoxypyrazine-2-carboximidamide (CAS#1344885-60-4) was converted to N-hydroxy-5-methoxypyrazine-2-carbimidoyl chloride by treatment with sodium nitrite in water/HCl at 0° C. Off-white solid. MS: m/z=188.3 [M+H]+.

Step 2: In analogy to Example 13, step 3, tert-butyl ((9R,11R)-9-(5-ethynyl-2-fluorophenyl)-9-methyl-11-oxido-2,3,4,5,9,10-hexahydro-[1,2,4]thiadiazino [1,2-a][1,2,7]thiadiazepin-7-yl)carbamate was converted to tert-butyl ((9R,11R)-9-(2-fluoro-5-(3-(5-methoxypyrazin-2-yl)isoxazol-5-yl)phenyl)-9-methyl-11-oxido-2,3,4,5,9,10-hexahydro-[1,2,4]thiadiazino[1,2-a][1,2,7]thiadiazepin-7-yl)carbamate by treatment with N-hydroxy-5-methoxypyrazine-2-carbimidoyl chloride in the presence of sodium bicarbonate. Colorless solid. MS: m/z=486.3 [M-BOC+H]+.

Step 3: In analogy to Example 13, step 4, tert-butyl ((9R,11R)-9-(2-fluoro-5-(3-(5-methoxypyrazin-2-yl)isoxazol-5-yl)phenyl)-9-methyl-11-oxido-2,3,4,5,9,10-hexahydro-[1,2,4]thiadiazino[1,2-a][1,2,7]thiadiazepin-7-yl) carbamate was converted to (9R,11R)-7-amino-9-(2-fluoro-5-(3-(5-methoxypyrazin-2-yl)isoxazol-5-yl)phenyl)-9-methyl-2,3,4,5,9,10-hexahydro-[1,2,4]thiadiazino[1,2-a][1,2,7]thiadiazepine 11-oxide 2,2,2-trifluoroacetate by treatment with trifluoroacetic acid in dichloromethane. Colorless solid. MS: m/z=486.3 [M+H]+.

Example 18

(9R,11S)-7-Amino-9-(2-fluoro-5-(3-(5-methoxy-pyrazin-2-yl)isoxazol-5-yl)phenyl)-9-methyl-2,3,4,5,9,10-hexahydro-[1,2,4]thiadiazino[1,2-a][1,2,7]thia-diazepine 11-oxide 2,2,2-trifluoroacetate

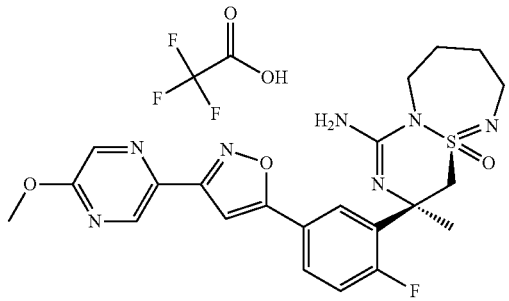

Step 1: In analogy to Example 13, step 3, tert-butyl ((9R,11S)-9-(5-ethynyl-2-fluorophenyl)-9-methyl-11-oxido-2,3,4,5,9,10-hexahydro-[1,2,4]thiadiazino [1,2-a][1,2,7]thiadiazepin-7-yl)carbamate was converted to tert-butyl ((9R,11S)-9-(2-fluoro-5-(3-(5-methoxypyrazin-2-yl)isoxazol-5-yl)phenyl)-9-methyl-11-oxido-2,3,4,5,9,10-hexahydro-[1,2,4]thiadiazino [1,2-a][1,2,7]thiadiazepin-7-yl) carbamate by treatment with N-hydroxy-5-methoxypyrazine-2-carbimidoyl chloride in the presence of sodium bicarbonate. Colorless solid. MS: m/z=586.4 [M+H]+.

Step 2: In analogy to Example 13, step 4, tert-butyl ((9R,11S)-9-(2-fluoro-5-(3-(5-methoxypyrazin-2-yl)isoxazol-5-yl)phenyl)-9-methyl-11-oxido-2,3,4,5,9,10-hexahydro-[1,2,4]thiadiazino[1,2-a][1,2,7]thiadiazepin-7-yl) carbamate was converted to (9R,11S)-7-amino-9-(2-fluoro-5-(3-(5-methoxypyrazin-2-yl)isoxazol-5-yl)phenyl)-9-methyl-2,3,4,5,9,10-hexahydro-[1,2,4]thiadiazino[1,2-a][1,2,7]thiadiazepine 11-oxide 2,2,2-trifluoroacetate by treatment with trifluoroacetic acid in dichloromethane. Off-white solid. MS: m/z=486.4 [M+H]+.

Example 19

(9R,11R)-7-Amino-9-(5-(3-(5-(2,2-difluoroethoxy)pyrazin-2-yl)isoxazol-5-yl)-2-fluorophenyl)-9-methyl-2,3,4,5,9,10-hexahydro-[1,2,4]thiadiazino[1,2-a][1,2,7]thiadiazepine 11-oxide 2,2,2-trifluoroacetate

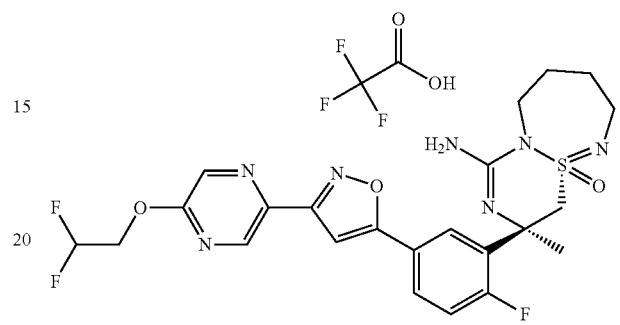

Step 1: In analogy to Example 13, step 1, 5-(2,2-difluoroethoxy)pyrazine-2-carbonitrile (CAS#1544861-08-6) was converted to 5-(2,2-difluoroethoxy)-N'-hydroxypyrazine-2-carboximidamide by treatment with hydroxylamine hydrochloride in the presence of aqueous sodium hydroxide. Off-white solid. MS: m/z=219.1 [M+H]+.

Step 2: In analogy to Example 13, step 2, 5-(2,2-difluoroethoxy)-N'-hydroxypyrazine-2-carboximidamide was converted to 5-(2,2-difluoroethoxy)-N-hydroxypyrazine-2-carbimidoyl chloride by treatment with sodium nitrite in water/HCl at 0° C. Yellow solid.

Step 3: In analogy to Example 13, step 3, tert-butyl ((9R,11R)-9-(5-ethynyl-2-fluorophenyl)-9-methyl-11-oxido-2,3,4,5,9,10-hexahydro-[1,2,4]thiadiazino [1,2-a][1,2,7]thiadiazepin-7-yl)carbamate was converted to tert-butyl ((9R,11R)-9-(5-(3-(5-(2,2-difluoroethoxy)pyrazin-2-yl)isoxazol-5-yl)-2-fluorophenyl)-9-methyl-11-oxido-2,3,4,5,9,10-hexahydro-[1,2,4]thiadiazino[1,2-a][1,2,7]thiadiazepin-7-yl)carbamate by treatment with 5-(2,2-difluoroethoxy)-N-hydroxypyrazine-2-carbimidoyl chloride in the presence of sodium bicarbonate. Off-white solid. MS: m/z=536.3[M-BOC+H]+.

Step 4: In analogy to Example 13, step 4, tert-butyl ((9R,11R)-9-(5-(3-(5-(2,2-difluoroethoxy)pyrazin-2-yl)isoxazol-5-yl)-2-fluorophenyl)-9-methyl-11-oxido-2,3,4,5,9,10-hexahydro-[1,2,4]thiadiazino[1,2-a][1,2,7]thiadiazepin-7-yl)carbamate was converted to (9R,11R)-7-amino-9-(5-(3-(5-(2,2-difluoroethoxy)pyrazin-2-yl)isoxazol-5-yl)-2-fluorophenyl)-9-methyl-2,3,4,5,9,10-hexahydro-[1,2,4]thiadiazino [1,2-a][1,2,7]thiadiazepine 11-oxide 2,2,2-trifluoroacetate by treatment with trifluoroacetic acid in dichloromethane. Light brown solid. MS: m/z=536.3 [M+H]+.

Example 20

3-Chloro-5-cyano-pyridine-2-carboxylic acid [3-((3R,4aS)-1-amino-3-methyl-4a-oxo-3,4,6,7,8,9-hexahydro-4aλ⁶-thia-2,5,9a-triaza-benzocyclohepten-3-yl)-4-fluoro-phenyl]-amide

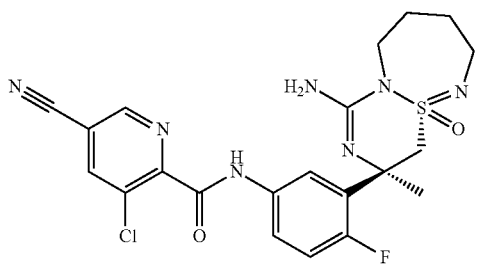 [SMILES: C[C@@]1(c2cc(NC(=O)c3ncc(C#N)cc3Cl)ccc2F)C[S@@]2(=O)=NCCCCN2C(N)=N1]

To a solution of 3-chloro-5-cyanopicolinic acid (39.3 mg, 215 μmol, Eq: 1.00) in methanol (3.00 ml) was added at 0° C. 4-(4,6-dimethoxy-1,3,5-triazin-2-yl)-4-methylmorpholinium chloride (DMTMM) (83.3 mg, 301 μmol, Eq: 1.4), the colorless solution was stirred at 0° C. for 30 min, then a solution of (3R,4aS)-3-(5-amino-2-fluoro-phenyl)-3-methyl-4a-oxo-3,4,6,7,8,9-hexahydro-4aλ⁶-thia-2,5,9a-triaza-benzocyclohepten-1-ylamine (70 mg, 215 μmol, Eq: 1.00) in methanol (5.00 ml) was added dropwise via syringe and the reaction mixture was stirred at 23° C. for 4 h. Extracted with ethyl acetate and sat. NaHCO₃-sol. plus brine, dried organic layer over Na₂SO₄. Filtration and removal of the solvent in vacuum left a brown foam which was purified by flash chromatography (NH₂-silica gel, 20 g, 0% to 100% EtOAc in heptane) to give the 3-chloro-5-cyano-pyridine-2-carboxylic acid [3-((3R,4aS)-1-amino-3-methyl-4a-oxo-3,4,6,7,8,9-hexahydro-4aλ⁶-thia-2,5,9a-triaza-benzocyclohepten-3-yl)-4-fluoro-phenyl]-amide (28 mg, 57.1 μmol, 26.6% yield) as a light yellow solid. MS (ISP): m/z=490.1 [(M+H)⁺], 492.1 [(M+2+H)⁺].

Example 21

5-(2,2,2-Trifluoro-ethoxy)-pyridine-2-carboxylic acid [3-((3R,4aS)-1-amino-3-methyl-4a-oxo-3,4,6,7,8,9-hexahydro-4aλ⁶-thia-2,5,9a-triaza-benzocyclohepten-3-yl)-4-fluoro-phenyl]-amide

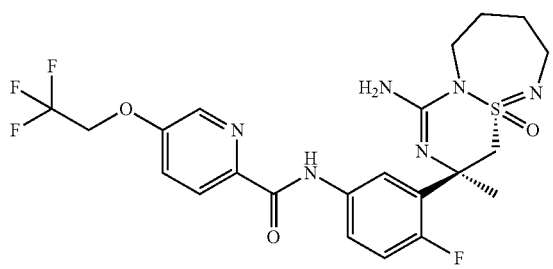 [SMILES: C[C@@]1(c2cc(NC(=O)c3ccc(OCC(F)(F)F)cn3)ccc2F)C[S@@]2(=O)=NCCCCN2C(N)=N1]

To a solution of 5-(2,2,2-trifluoroethoxy)picolinic acid [CAS-no. 881409-53-6](37.4 mg, 169 μmol, Eq: 1.1) in methanol (3.00 ml) was added at 0° C. 4-(4,6-dimethoxy-1,3,5-triazin-2-yl)-4-methylmorpholinium chloride (DMTMM) (59.5 mg, 215 μmol, Eq: 1.4), the colorless solution was stirred at 0° C. for 30 min, then a solution of (3R,4aS)-3-(5-amino-2-fluoro-phenyl)-3-methyl-4a-oxo-3,4,6,7,8,9-hexahydro-4aλ⁶-thia-2,5,9a-triaza-benzocyclohepten-1-ylamine (50 mg, 154 μmol, Eq: 1.00) in methanol (5.00 ml) was added dropwise via syringe and the reaction mixture was stirred at 23° C. for 4 h. Extracted with ethyl acetate and sat. NaHCO₃-sol. plus brine, dried organic layer over Na₂SO₄. Filtration and removal of the solvent in vacuum left a brown foam which was purified by flash chromatography (NH₂-silica gel, 20 g, 0% to 100% EtOAc in heptane) to give the 5-(2,2,2-trifluoro-ethoxy)-pyridine-2-carboxylic acid [3-((3R,4aS)-1-amino-3-methyl-4a-oxo-3,4,6,7,8,9-hexahydro-4aλ⁶-thia-2,5,9a-triaza-benzocyclohepten-3-yl)-4-fluoro-phenyl]-amide (35 mg, 66.2 μmol, 43.1% yield) as a white solid. MS (ISP): m/z=529.2 [(M+H)⁺].

Example 22

5-But-2-ynyloxy-pyrazine-2-carboxylic acid [3-((3R,4aS)-1-amino-3-methyl-4a-oxo-3,4,6,7,8,9-hexahydro-4aλ⁶-thia-2,5,9a-triaza-benzocyclohepten-3-yl)-4-fluoro-phenyl]-amide

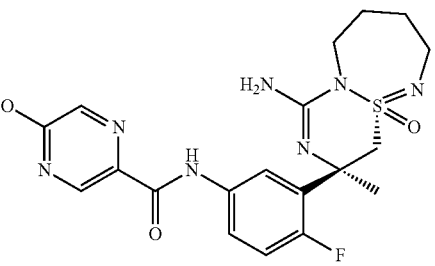

To a solution of 5-(but-2-ynyloxy)pyrazine-2-carboxylic acid [CAS-no. 1221447-98-8](32.5 mg, 169 μmol, Eq: 1.1) in methanol (3.00 ml) was added at 0° C. 4-(4,6-dimethoxy-1,3,5-triazin-2-yl)-4-methylmorpholinium chloride (DMTMM) (59.5 mg, 215 μmol, Eq: 1.4), the colorless solution was stirred at 0° C. for 30 min, then a solution of (3R,4aS)-3-(5-amino-2-fluoro-phenyl)-3-methyl-4a-oxo-3,4,6,7,8,9-hexahydro-4aλ⁶-thia-2,5,9a-triaza-benzocyclohepten-1-ylamine (50 mg, 154 μmol, Eq: 1.00) in methanol (5.00 ml) was added dropwise via syringe and the reaction mixture was stirred at 23° C. for 4 h. Extracted with ethyl acetate and sat. NaHCO₃-sol. plus brine, dried organic layer over Na₂SO₄. Filtration and removal of the solvent in vacuum left a brown foam which was purified by flash chromatography (NH₂-silica gel, 20 g, 0% to 100% EtOAc in heptane) to give the 5-but-2-ynyloxy-pyrazine-2-carboxylic acid [3-((3R,4aS)-1-amino-3-methyl-4a-oxo-3,4,6,7,8,9-hexahydro-4aλ⁶-thia-2,5,9a-triaza-benzocyclohepten-3-yl)-4-fluoro-phenyl]-amide (35 mg, 70.1 μmol, 45.6% yield) as a white solid. MS (ISP): m/z=500.3 [(M+H)⁺].

Example 23

5-Fluoro-3-methyl-pyridine-2-carboxylic acid [3-((3R,4aS)-1-amino-3-methyl-4a-oxo-3,4,6,7,8,9-hexahydro-4aλ⁶-thia-2,5,9a-triaza-benzocyclohepten-3-yl)-4-fluoro-phenyl]-amide

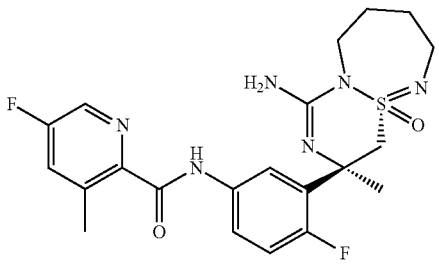 [SMILES: Cc1cc(F)cnc1C(=O)Nc1ccc(F)c([C@]2(C)C[S@@]3(=O)=NCCCCN3C(N)=N2)c1]

To a solution of 5-fluoro-3-methylpicolinic acid (40.0 mg, 258 µmol, Eq: 1.2) in methanol (3.00 ml) was added at 0° C. 4-(4,6-dimethoxy-1,3,5-triazin-2-yl)-4-methylmorpholinium chloride (DMTMM) (83.3 mg, 301 µmol, Eq: 1.4), the colorless solution was stirred at 0° C. for 30 min, then a solution of (3R,4aS)-3-(5-amino-2-fluoro-phenyl)-3-methyl-4a-oxo-3,4,6,7,8,9-hexahydro-4aλ⁶-thia-2,5,9a-triaza-benzocyclohepten-1-ylamine (70 mg, 215 µmol, Eq: 1.00) in methanol (5.00 ml) was added dropwise via syringe and the reaction mixture was stirred at 23° C. for 4 h. Extracted with ethyl acetate and sat. NaHCO₃-sol. plus brine, dried organic layer over Na₂SO₄. Filtration and removal of the solvent in vacuum left a brown foam which was purified by flash chromatography (NH₂-silica gel, 20 g, 0% to 100% EtOAc in heptane) to give the 5-fluoro-3-methyl-pyridine-2-carboxylic acid [3-((3R,4aS)-1-amino-3-methyl-4a-oxo-3,4,6,7,8,9-hexahydro-4aλ⁶-thia-2,5,9a-triaza-benzocyclohepten-3-yl)-4-fluoro-phenyl]-amide (29 mg, 62.7 µmol, 29.1% yield) as a white solid. MS (ISP): m/z=463.2 [(M+H)⁺].

Example 24

N-(3-((2S,9R)-7-amino-9-methyl-11-oxido-2-(trifluoromethyl)-2,3,4,5,9,10-hexahydro-[1,2,4]thiadiazino[1,2-a][1,2,7]thiadiazepin-9-yl)-4-fluorophenyl)-5-cyano-3-methylpicolinamide

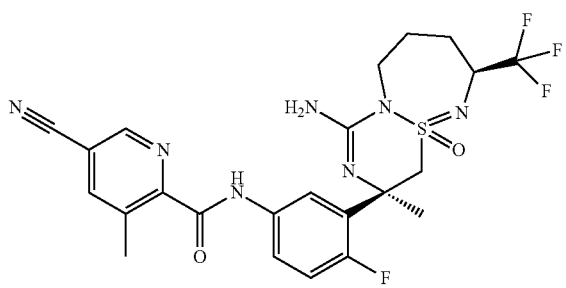 [SMILES: Cc1cc(C#N)cnc1C(=O)Nc1ccc(F)c([C@]2(C)CS3(=O)=N[C@H](C(F)(F)F)CCCN3C(N)=N2)c1]

To a solution of 5-cyano-3-methylpicolinic acid (20.2 mg, 125 µmol, Eq: 1) in methanol (6.25 ml) was added at 0° C. 4-(4,6-dimethoxy-1,3,5-triazin-2-yl)-4-methylmorpholinium chloride (DMTMM) (48.3 mg, 174 µmol, Eq: 1.4), the colorless solution was stirred at 0° C. for min, then a solution of (2S,9R)-7-amino-9-(5-amino-2-fluorophenyl)-9-methyl-2-(trifluoromethyl)-2,3,4,5,9,10-hexahydro-[1,2,4]thiadiazino [1,2-a][1,2,7]thiadiazepine 11-oxide (49 mg, 125 µmol, Eq: 1) in methanol (6.25 ml) was added dropwise via syringe and the reaction mixture was stirred at 23° C. for 18 h. Extracted with ethyl acetate and sat. NaHCO₃-sol. plus brine, dried organic layer over Na₂SO₄. Filtration and removal of the solvent in vacuum left a brown foam which was purified by flash chromatography (silica gel, 10 g, 0% to 100% EtOAc in heptane) to give the N-(3-((2S,9R)-7-amino-9-methyl-11-oxido-2-(trifluoromethyl)-2,3,4,5,9,10-hexahydro-[1,2,4]thiadiazino [1,2-a][1,2,7]thiadiazepin-9-yl)-4-fluorophenyl)-5-cyano-3-methylpicolinamide (51 mg, 94.9 µmol, 76.2% yield) as light yellow foam. MS (ISP): m/z=538.2 [(M+H)⁺].

Example 25

N-(3-((8R)-6-amino-3,3-difluoro-8-methyl-10-oxido-3,4,8,9-tetrahydro-2H-[1,2,6]thiadiazino[1,2-a][1,2,4]thiadiazin-8-yl)-4-fluorophenyl)-5-cyano-3-methylpicolinamide

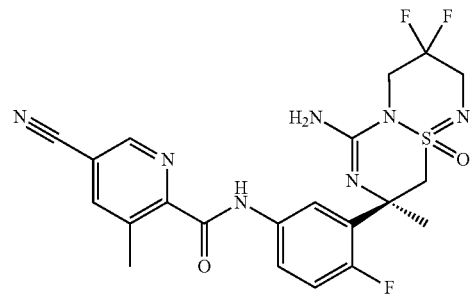 [SMILES: Cc1cc(C#N)cnc1C(=O)Nc1ccc(F)c([C@]2(C)CS3(=O)=NCC(F)(F)CN3C(N)=N2)c1]

To a solution of 5-cyano-3-methylpicolinic acid (8.96 mg, 55.3 µmol, Eq: 1.2) in methanol (2 ml) was added at 0° C. 4-(4,6-dimethoxy-1,3,5-triazin-2-yl)-4-methylmorpholinium chloride (DMTMM) (17.8 mg, 64.5 µmol, Eq: 1.4), the colorless solution was stirred at 0° C. for 30 min, then a solution of (8R)-6-amino-8-(5-amino-2-fluorophenyl)-3,3-difluoro-8-methyl-3,4,8,9-tetrahydro-2H-[1,2,6]thiadiazino [1,2-a][1,2,4]thiadiazine 10-oxide (16 mg, 46.1 µmol, Eq: 1) in methanol (2 ml) was added dropwise via syringe and the reaction mixture was stirred at 23° C. for 18 h. Extracted with ethyl acetate and sat. NaHCO₃-sol. plus brine, dried organic layer over Na₂SO₄. Filtration and removal of the solvent in vacuum left a brown foam which was purified by flash chromatography (silica gel, 10 g, 0% to 100% EtOAc in heptane) to give a partially purified product which was triturated with diethyl ether to give the N-(3-((8R)-6-amino-3,3-difluoro-8-methyl-10-oxido-3,4,8,9-tetrahydro-2H-[1,2,6]thiadiazino[1,2-a][1,2,4]thiadiazin-8-yl)-4-fluorophenyl)-5-cyano-3-methylpicolinamide (7 mg, 14.2 µmol, 30.9% yield) as light brown solid. MS (ISP): m/z=492.2 [(M+H)⁺].

The invention claimed is:

1. A compound of formula I',

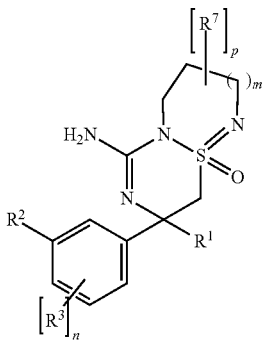

wherein
R¹ is selected from the group consisting of
  i) $C_{1-6}$-alkyl, and
  ii) halogen-$C_{1-6}$-alkyl;
R² is selected from the group consisting of
  i) hydrogen,
  ii) halogen;
  iii) —NH—C(=O)—R⁴,
  iv) aryl,
  v) aryl, substituted by 1-3 substituents individually selected from cyano, $C_{1-6}$-alkyl, halogen-$C_{1-6}$-alkyl and halogen
  vi) heteroaryl,
  vii) heteroaryl, substituted by 1-3 substituents individually selected from R⁶, and
  viii) —C≡C—R⁵;
R³ is halogen;
R⁴ is selected from the group consisting of
  i) heteroaryl, and
  ii) heteroaryl, optionally substituted by 1-3 substituents individually selected from R⁶,
R⁵ is selected from the group consisting of
  i) aryl,
  ii) aryl, optionally substituted by 1-3 substituents individually selected from cyano, $C_{1-6}$-alkyl, halogen-$C_{1-6}$-alkyl and halogen
  iii) heteroaryl, and
  iv) heteroaryl, optionally substituted by 1-3 substituents individually selected from cyano, $C_{1-6}$-alkyl, halogen-$C_{1-6}$-alkyl and halogen;
R⁶ is selected from the group consisting of
  i) cyano,
  ii) halogen;
  iii) $C_{1-6}$-alkyl,
  iv) halogen-$C_{1-6}$-alkyl,
  v) $C_{2-6}$-alkynyl-O—,
  vi) heteroaryl, and
  vii) heteroaryl, optionally substituted by 1-3 substituents individually selected from cyano, $C_{1-6}$-alkyl, $C_{1-6}$-alkoxy, halogen-$C_{1-6}$-alkyl, halogen-$C_{1-6}$-alkoxy and halogen;
R⁷ is selected from the group consisting of
  i) halogen, and
  ii) halogen-$C_{1-6}$-alkyl;
m is 1 or 2;
n is 0 or 1; and
p is 0, 1 or 2;
or pharmaceutically acceptable salts thereof.

2. The compound of formula I' according to claim 1, wherein p is 0.

3. The compound of formula I' according to claim 1, that is of formula I,

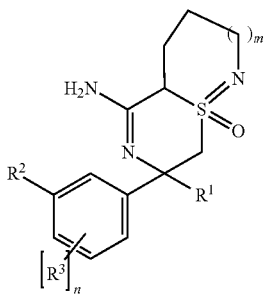

wherein
R¹ is selected from the group consisting of
  i) $C_{1-6}$-alkyl, and
  ii) halogen-$C_{1-6}$-alkyl;
R² is selected from the group consisting of
  i) hydrogen,
  ii) halogen;
  iii) —NH—C(=O)—R⁴,
  iv) aryl,
  v) aryl, substituted by 1-3 substituents individually selected from cyano, $C_{1-6}$-alkyl, halogen-$C_{1-6}$-alkyl and halogen
  vi) heteroaryl,
  vii) heteroaryl, substituted by 1-3 substituents individually selected from cyano, $C_{1-6}$-alkyl, halogen-$C_{1-6}$-alkyl and halogen, and
  viii) —C≡C—R⁵;
R³ is halogen;
R⁴ is selected from the group consisting of
  i) heteroaryl, and
  ii) heteroaryl, optionally substituted by 1-3 substituents individually selected from cyano, $C_{1-6}$-alkyl, halogen-$C_{1-6}$-alkyl and halogen;
R⁵ is selected from the group consisting of
  i) heteroaryl, and
  ii) heteroaryl, optionally substituted by 1-3 substituents individually selected from cyano, $C_{1-6}$-alkyl, halogen-$C_{1-6}$-alkyl and halogen;
m is 1 or 2; and
n is 0 or 1;
or pharmaceutically acceptable salts thereof.

4. The compound of formula I according to claim 1, which is of formula Ia, wherein R¹, R² and m are as described in claim 1

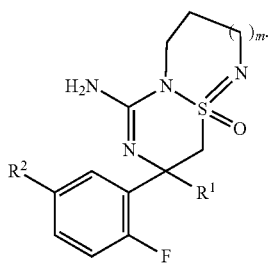

5. The compound of formula I' according to claim 1, wherein m is 2.

6. The compound of formula I' according to claim 1, wherein $R^1$ is methyl.

7. The compound of formula I' according to claim 1, wherein $R^2$ is —NH—C(=O)—$R^4$.

8. The compound of formula I' according to claim 1, wherein $R^4$ is heteroaryl, optionally substituted by cyano.

9. The compound of formula I' according to claim 1, wherein $R^2$ is heteroaryl, optionally substituted by cyano.

10. The compound of formula I' according to claim 1, wherein $R^2$ is —C≡C—$R^5$.

11. The compound of formula I' according to claim 1, wherein $R^5$ is heteroaryl, optionally substituted by halogen and halogen-$C_{1-6}$-alkyl.

12. The compound of formula I' according to claim 1, that is selected from the group consisting of:
- (3RS,4aRS)-3-(2-fluoro-phenyl)-3-methyl-4a-oxo-3,4,6,7,8,9-hexahydro-4a$\lambda^6$-thia-2,5,9a-triaza-benzocyclohepten-1-ylamine,
- (3RS,4aSR)-3-(2-fluoro-phenyl)-3-methyl-4a-oxo-3,4,6,7,8,9-hexahydro-4a$\lambda^6$-thia-2,5,9a-triaza-benzocyclohepten-1-ylamine,
- (3R,4aR)-3-(2-fluoro-phenyl)-3-methyl-4a-oxo-3,4,6,7,8,9-hexahydro-4a$\lambda^6$-thia-2,5,9a-triaza-benzocyclohepten-1-ylamine,
- (3R,4aS)-3-(2-fluoro-phenyl)-3-methyl-4a-oxo-3,4,6,7,8,9-hexahydro-4a$\lambda^6$-thia-2,5,9a-triaza-benzocyclohepten-1-ylamine,
- (3R,4aR)-3-(2-Fluoro-5-iodo-phenyl)-3-methyl-4a-oxo-3,4,6,7,8,9-hexahydro-4a$\lambda^6$-thia-2,5,9a-triaza-benzocyclohepten-1-ylamine,
- (3R,4aS)-3-(2-Fluoro-5-iodo-phenyl)-3-methyl-4a-oxo-3,4,6,7,8,9-hexahydro-4a$\lambda^6$-thia-2,5,9a-triaza-benzocyclohepten-1-ylamine,
- 5-cyano-pyridine-2-carboxylic acid [3-((3RS,4aRS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide,
- 5-cyano-pyridine-2-carboxylic acid [3-((3RS,4aSR)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide,
- 5-cyano-pyridine-2-carboxylic acid [3-((3R,4aR)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide,
- 5-cyano-pyridine-2-carboxylic acid [3-((3R,4aS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide,
- 5-[3-((3R,4aR)-1-amino-3-methyl-4a-oxo-3,4,6,7,8,9-hexahydro-4a$\lambda^6$-thia2,5,9a-triaza-benzocyclohepten-3-yl)-4-fluoro-phenyl]-nicotinonitrile,
- (3R,4aR)-3-(2-Fluoro-5-pyrimidin-5-yl-phenyl)-3-methyl-4a-oxo-3,4,6,7,8,9hexahydro-4a$\lambda^6$-thia-2,5,9a-triaza-benzocyclohepten-1-ylamine,
- 5-Chloro-pyridine-2-carboxylic acid [3-((3R,4aR)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide,
- 5-[3-((3R,4aS)-1-amino-3-methyl-4a-oxo-3,4,6,7,8,9-hexahydro-4a$\lambda$6-thia-2,5,9a-triaza-benzocyclohepten-3-yl)-4-fluoro-phenyl]-nicotinonitrile,
- (3R,4aS)-3-(2-Fluoro-5-pyrimidin-5-yl-phenyl)-3-methyl-4a-oxo-3,4,6,7,8,9hexahydro-4a$\lambda^6$-thia-2,5,9a-triaza-benzocyclohepten-1-ylamine,
- 5-Cyano-3-methyl-pyridine-2-carboxylic acid [3-((3R,4aR)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide,
- 5-Chloro-pyridine-2-carboxylic acid [3-((3R,4aS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide,
- 5-Cyano-3-methyl-pyridine-2-carboxylic acid [3-((3R,4aS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide,
- (9R,11R)-7-amino-9-(5-(3-(5-chloropyrimidin-2-yl)isoxazol-5-yl)-2-fluorophenyl)-9-methyl-2,3,4,5,9,10-hexahydro-[1,2,4]thiadiazino[1,2-a][1,2,7]thiadiazepine 11-oxide 2,2,2-trifluoroacetate,
- (9R,11S)-7-amino-9-(5-(3-(5-chloropyrimidin-2-yl)isoxazol-5-yl)-2-fluorophenyl)-9-methyl-2,3,4,5,9,10-hexahydro-[1,2,4]thiadiazino[1,2-a][1,2,7]thiadiazepine 11-oxide 2,2,2-trifluoroacetate,
- 6-(4-(3-((9R, 11 S)-7-amino-9-methyl-11-oxido-2,3,4,5,9,10-hexahydro-[1,2,4]thiadiazino[1,2-a][1,2,7]thiadiazepin-9-yl)-4-fluorophenyl)-1H-1,2,3-triazol-1-yl)nicotinonitrile 2,2,2-trifluoroacetate,
- 4-((3-((9R,11R)-7-amino-9-methyl-11-oxido-2,3,4,5,9,10-hexahydro-[1,2,4]thiadiazino[1,2-a][1,2,7]thiadiazepin-9-yl)-4-fluorophenyl)ethynyl)benzonitrile 2,2,2-trifluoroacetate,
- (9R,11R)-7-amino-9-(2-fluoro-5-(3-(5-methoxypyrazin-2-yl)isoxazol-5-yl)phenyl)-9-methyl-2,3,4,5,9,10-hexahydro-[1,2,4]thiadiazino[1,2-a][1,2,7]thiadiazepine 11-oxide 2,2,2-trifluoroacetate,
- (9R,11S)-7-amino-9-(2-fluoro-5-(3-(5-methoxypyrazin-2-yl)isoxazol-5-yl)phenyl)-9-methyl-2,3,4,5,9,10-hexahydro-[1,2,4]thiadiazino[1,2-a][1,2,7]thiadiazepine 11-oxide 2,2,2-trifluoroacetate,
- (9R,11R)-7-amino-9-(5-(3-(5-(2,2-difluoroethoxy)pyrazin-2-yl)isoxazol-5-yl)-2-fluorophenyl)-9-methyl-2,3,4,5,9,10-hexahydro-[1,2,4]thiadiazino[1,2-a][1,2,7]thiadiazepine 11-oxide 2,2,2-trifluoroacetate,
- 3-Chloro-5-cyano-pyridine-2-carboxylic acid [3-((3R,4aS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide,
- 5-(2,2,2-Trifluoro-ethoxy)-pyridine-2-carboxylic acid[3-((3R,4aS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide,
- 5-But-2-ynyloxy-pyrazine-2-carboxylic acid [3-((3R,4aS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]-amide,
- 5-Fluoro-3-methyl-pyridine-2-carboxylic acid [3-((3R,4aS)-1-amino-3-methyl-4a-oxo-3,4,6,7,8,9-hexahydro-4a$\lambda^6$-thia-2,5,9a-triaza-benzocyclohepten-3-yl)-4-fluoro-phenyl]amide,
- N-(3-((2S,9R)-7-amino-9-methyl-11-oxido-2-(trifluoromethyl)-2,3,4,5,9,10-hexahydro-[1,2,4]thiadiazino[1,2-a][1,2,7]thiadiazepin-9-yl)-4-fluorophenyl)-5-cyano-3-methylpicolinamide, and
- N-(3-((8R)-6-amino-3,3-difluoro-8-methyl-10-oxido-3,4,8,9-tetrahydro-2H-[1,2,6]thiadiazino[1,2-a][1,2,4]thiadiazin-8-yl)-4-fluorophenyl)-5-cyano-3-methylpicolinamide, or pharmaceutically acceptable salts thereof.

13. The compound of formula I according to claim 3, selected from the group consisting of:

(3R,4aR)-3-(2-Fluoro-5-iodo-phenyl)-3-methyl-4a-oxo-3,4,6,7,8,9-hexahydro-4aλ⁶-thia-2,5,9a-triaza-benzocyclohepten-1-ylamine, (3R,4aR)-3-(2-Fluoro-5-pyrimidin-5-yl-phenyl)-3-methyl-4a-oxo-3,4,6,7,8,9hexahydro-4aλ⁶-thia-2,5,9a-triaza-benzocyclohepten-1-ylamine, (3R,4aR)-3-(2-fluoro-phenyl)-3-methyl-4a-oxo-3,4,6,7,8,9-hexahydro-4aλ⁶-thia-2,5,9a-triaza-benzocyclohepten-1-ylamine, (3R,4aR)-3-[5-(4-Chloro-1-difluoromethyl-1H-pyrazol-3-ylethynyl)-2-fluoro-phenyl]-3-methyl-4a-oxo-3,4,6,7,8,9-hexahydro-4aλ6-thia-2,5,9a-triaza-benzocyclohepten-1-ylamine, (3R,4aS)-3-(2-Fluoro-5-iodo-phenyl)-3-methyl-4a-oxo-3,4,6,7,8,9-hexahydro-4aλ⁶-thia-2,5,9a-triaza-benzocyclohepten-1-ylamine, (3R,4aS)-3-(2-Fluoro-5-pyrimidin-5-yl-phenyl)-3-methyl-4a-oxo-3,4,6,7,8,9hexahydro-4aλ⁶-thia-2,5,9a-triaza-benzocyclohepten-1-ylamine, (3R,4aS)-3-(2-fluoro-phenyl)-3-methyl-4a-oxo-3,4,6,7,8,9-hexahydro-4aλ⁶-thia-2,5,9a-triaza-benzocyclohepten-1-ylamine, (3R,4aS)-3-[5-(4-Chloro-1-difluoromethyl-1H-pyrazol-3-ylethynyl)-2-fluoro-phenyl]-3-methyl-4a-oxo-3,4,6,7,8,9-hexahydro-4aλ⁶-thia-2,5,9a-triaza-benzocyclohepten-1-ylamine, (3RS,4aRS)-3-(2-fluoro-phenyl)-3-methyl-4a-oxo-3,4,6,7,8,9-hexahydro-4aλ⁶-thia-2,5,9a-triaza-benzocyclohepten-1-ylamine, (3RS,4aSR)-3-(2-fluoro-phenyl)-3-methyl-4a-oxo-3,4,6,7,8,9-hexahydro-4aλ⁶-thia-2,5,9a-triaza-benzocyclohepten-1-ylamine, 5-[3-((3R,4aR)-1-amino-3-methyl-4a-oxo-3,4,6,7,8,9-hexahydro-4aλ⁶-thia2,5,9a-triaza-benzocyclohepten-3-yl)-4-fluoro-phenyl]-nicotinonitrile, 5-[3-((3R,4aS)-1-amino-3-methyl-4a-oxo-3,4,6,7,8,9-hexahydro-4aλ⁶-thia2,5,9a-triaza-benzocyclohepten-3-yl)-4-fluoro-phenyl]-nicotinonitrile, 5-cyano-pyridine-2-carboxylic acid [3-((3R,4aR)-1-amino-3-methyl-4a-oxo-3,4,6,7,8,9hexahydro-4aλ⁶-thia-2,5,9a-triaza-benzocyclohepten-3-yl)-4-fluoro-phenyl]-amide, 5-cyano-pyridine-2-carboxylic acid [3-((3R,4aS)-1-amino-3-methyl-4a-oxo-3,4,6,7,8,9-hexahydro-4aλ⁶-thia-2,5,9a-triaza-benzocyclohepten-3-yl)-4-fluoro-phenyl]-amide, 5-cyano-pyridine-2-carboxylic acid [3-((3RS,4aRS)-1-amino-3-methyl-4a-oxo-3,4,6,7,8,9-hexahydro-4aλ⁶-thia-2,5,9a-triaza-benzocyclohepten-3-yl)-4-fluoro-phenyl]-amide, and 5-cyano-pyridine-2-carboxylic acid [3-((3RS,4aSR)-1-amino-3-methyl-4a-oxo-3,4,6,7,8,9-hexahydro-4aλ6-thia-2,5,9a-triaza-benzocyclohepten-3-yl)-4-fluoro-phenyl]-amide.

14. A pharmaceutical composition, comprising a compound of formula I' according to claim 1 and a pharmaceutically acceptable carrier and/or a pharmaceutically acceptable auxiliary substance.

15. A method for the therapeutic treatment of Alzheimer's disease, comprising the step of administering a compound of formula I' according to claim 1 to a human being or animal in need thereof.

* * * * *